(12) United States Patent
Chen et al.

(10) Patent No.: US 9,138,421 B2
(45) Date of Patent: Sep. 22, 2015

(54) PLATINUM COMPOUNDS FOR TREATING CELL PROLIFERATIVE DISEASES, PREPARATION METHOD AND USE THEREOF

(75) Inventors: Xiaoping Chen, Beijing (CN); Yashi Yan, Beijing (CN); Xiaoping Meng, Beijing (CN); Feng Zhao, Beijing (CN); Zejun Gao, Beijing (CN); Shouming Wen, Beijing (CN)

(73) Assignee: Beijing FSWelcome Technology Development Co., Ltd., Beijing (CN)

( * ) Notice: Subject to any disclaimer, the term of this patent is extended or adjusted under 35 U.S.C. 154(b) by 0 days.

(21) Appl. No.: 14/131,902

(22) PCT Filed: Jul. 6, 2012

(86) PCT No.: PCT/CN2012/078302
§ 371 (c)(1),
(2), (4) Date: Jan. 9, 2014

(87) PCT Pub. No.: WO2013/007172
PCT Pub. Date: Jan. 17, 2013

(65) Prior Publication Data
US 2014/0142079 A1    May 22, 2014

(30) Foreign Application Priority Data
Jul. 9, 2011   (CN) .......................... 2011 1 0192289

(51) Int. Cl.
*C07F 15/00*   (2006.01)
*A61K 31/282*  (2006.01)
*A61K 31/351*  (2006.01)

(52) U.S. Cl.
CPC .............. *A61K 31/351* (2013.01); *A61K 31/282* (2013.01); *C07F 15/0093* (2013.01)

(58) Field of Classification Search
CPC . C07F 15/0093; A61K 31/282; A61K 31/351
USPC ...................... 556/40; 549/210; 514/184, 492
See application file for complete search history.

(56) References Cited

U.S. PATENT DOCUMENTS

| 4,322,362 | A | 3/1982 | Kaplan et al. |
| 6,262,094 | B1 | 7/2001 | Hoefle et al. |
| 2004/0162342 | A1 | 8/2004 | Sohn et al. |
| 2006/0205677 | A1 | 9/2006 | Gao et al. |
| 2010/0197890 | A1 | 8/2010 | McTavish |

FOREIGN PATENT DOCUMENTS

| CN | 88101195 A | 9/1988 |
| CN | 1698903 | 11/2005 |
| CN | 101475600 A | 7/2009 |
| CN | 102276657 A | 12/2011 |
| CN | 102276674 A | 12/2011 |
| CN | 102286050 A | 12/2011 |
| DE | 4138042 A1 | 5/1993 |
| JP | 6137794 | 2/1986 |
| JP | S61249993 A | 11/1986 |
| WO | 9008157 A1 | 7/1990 |
| WO | 9719086 A1 | 5/1997 |
| WO | 9730992 A1 | 8/1997 |
| WO | 9822461 A1 | 5/1998 |
| WO | 9825929 A1 | 6/1998 |
| WO | 9838192 A1 | 9/1998 |
| WO | 9854966 A1 | 12/1998 |
| WO | 9901124 A1 | 1/1999 |
| WO | 9902224 A1 | 1/1999 |
| WO | 9902514 A2 | 1/1999 |
| WO | 9903848 A1 | 1/1999 |
| WO | 9907692 A2 | 2/1999 |
| WO | 9924416 A1 | 5/1999 |
| WO | 9927890 A2 | 6/1999 |
| WO | 9928324 A1 | 6/1999 |
| WO | 9943653 A1 | 9/1999 |
| WO | 9954318 A1 | 10/1999 |
| WO | 9954319 A1 | 10/1999 |
| WO | 9954330 A1 | 10/1999 |
| WO | 9965913 A2 | 12/1999 |
| WO | 9967252 A2 | 12/1999 |
| WO | 9967253 A2 | 12/1999 |
| WO | 0000485 A1 | 1/2000 |
| WO | 2006091790 A1 | 8/2006 |

OTHER PUBLICATIONS

Caron, G. et al., "The Relevance of Polar Surface Area (PSA) in Rationalizing Biological Properties of Several Cis-Diam-mineralonatoplatinum(II) Derivatives," ChemNedChem, vol. 4, No. 10, Jul. 27, 2009, pp. 1677-1685.

D. Gibson et al., "Anthraquinone Intercalators as Carrier Molecules for Second-Generation Platinum Anticancer Drugs," Eur. J. Med. Chem., vol. 32, No. 10, 1997, pp. 823-831.

Jakupec et al., "Tumor-inhibiting platinum complexes-state of art and future perspectives," Rev. Physiol Biochem Pharmacol., 2003, 146, pp. 1-53.

Supplementary European Search Report dated Jan. 29, 2015 for Application No. 12811424.6.

Notification of Reason for Refusal issued by the Japanese Patent Office for Application No. 2014-519389, dated Jan. 21, 2015, and English language summary.

(Continued)

*Primary Examiner* — Porfirio Nazario Gonzalez
(74) *Attorney, Agent, or Firm* — Lando & Anastasi, LLP

(57) ABSTRACT

Disclosed are a class of platinum compounds with a leaving group of malonic acid derivatives containing amino and alkylamino, their pharmaceutically acceptable salts, their preparation methods and pharmaceutical composites comprising them. Disclosed also are for the uses of the compounds in the treatment of cell proliferative diseases, particularly for the treatment of cancers. The present platinum compounds have high water solubility and low toxicity.

33 Claims, No Drawings

(56) References Cited

OTHER PUBLICATIONS

SG Bagrova, Vopr Onkol, 2001, 47(6): 752-756.
US Bioscience. Pharma Projects, 1998: a1744-a1745.
International Preliminary Report on Patentability and Written Opinion dated Jan. 14, 2014 for Application No. PCT/CN2012/078302.
International Search Report dated Oct. 25, 2012 for Application No. PCT/CN2012/078302.
Chinese Search Report dated Mar. 23, 2015 for Application No. 2012800231240 (English translation not available).
Wang et al., "Antitumor Platinum Drugs in accord with Classical Structure-Activity Relationships," Chemistry Online (http://hxtb.org) Dec. 2003, pp. 828-836.
Wang et al., "Synthesis, Characterization and Anti-tumor Activities of a Series of Platinum (II) Complexes with 1R,3S-1,2,2-Trimethylcyclopentanediamine," Chinese Journal of Inorganic Chemistry, vol. 20, No. 7, Jul. 2004, pp. 775-780.
Zhang et al., "Design and synthesis of highly water-soluble platinum antineoplastic drugs," China Medical Herald, 2012, pp. 120-122.

PLATINUM COMPOUNDS FOR TREATING CELL PROLIFERATIVE DISEASES, PREPARATION METHOD AND USE THEREOF

FIELD OF THE INVENTION

The invention relates a category of platinum containing compounds for treating cell proliferative diseases in particular, relates a serises of platinum containing compounds with the leaving group of malonic acid derivatives containing amino and alkyl amino radical, preparation methods and uses thereof.

BACKGROUND OF THE INVENTION

Cancers (malignant tumor) are among the leading diseases threatening the human life today. The morbidity and mortality of cancers have increased sharply in recent years. The tumor development trend revealed by the World Health Organization indicates that, the annual global newly confirmed tumor patients are more than 10,000,000 since 1996. As in the end of 1996, the global total tumor patients have exceeded 40,000,000. Approximately 7,000,000 persons die of various cancers all around the world each year. In 2001, the world morbidity and mortality of tumor have increased by 22% from 1990. Cancer has become the second main cause of death just next to cardiovascular and cerebrovascular diseases. The most common cancers are lung cancer, breast cancer, colorectal cancer, gastric cancer, liver cancer, cervical cancer, esophageal cancer, and bladder cancer. The authoritative survey data on the morbidity and mortality of cancers in China in 2006 published on the tenth National Clinical Oncology Conference show that, the cancer deaths are 3,000,000 in China in 2006. There are approximately 2,120,000 newly confirmed cancer patients each year. In the mortality of malignant tumor, lung cancer ranks the first of malignant tumor. Experts estimated that, by 2020, the death toll will exceed 4,000,000; by 2025, tumor will become the first major cause for global death toll.

There are three means for clinically treating cancers: operation, radiotherapy and chemotherapy. Antitumor drugs are the most commonly used way of the treatment. In 2008, the global market sale of antitumor drugs is US$ 48 billion. At present, clinical antitumor drugs are mainly classified into alkylating agent, antimetabolites, metal platinum, plant alkaloids and other crude drugs, cytotoxic antibiotics, etc. Platinum antitumor drugs are sort of principal antitumor drugs and cisplatin was firstly developed in 1960s. The important difference from traditional cytotoxic antitumor drugs is their unique mechanism of action and excellent selectivity. The major target is DNA, which is cross-linked inter and intra DNAs and forms platinum complex–DNA complex, to disturb DNA replication or combine with nucleoprotein and plasmosin, belonging to cell cycle nonspecific agent (CCNSA). Cis-dichlorodiamminoplatinum i.e., Cisplatin, cis-1,1-cyclobutanedicarboxylate platinum, i.e., Carboplatin, cis-glycolic acid-diammineplatinum i.e., Nedaplatin, oxalate-(trans-L-1, 2-cyclohexanediamine) platinum i.e., Oxaliplatin, cis-[(4R, 5R)-4,5-bi-(aminomethyl)-2-isopropyl 1, 3-dioxane](bidentate) platinum, i.e., Sunpla, and 1,2 diaminomethyl-cyclobutane-lactate platinum i.e., Lobaplatin etc. have been successfully developed in succession. Platinum antitumor drugs are characterized by wide antitumor spectrum, good effect, etc. Moreover, they are well collaborated with other antitumor drugs. This not only improves the inhabitation ratio of the existed tumor, but also expands antitumor spectrum, thus consolidating the position of platinum antitumor drugs in clinical treatment. In the ranking among hundreds of antitumor drugs conducted by WHO in 1995, cisplatin ranks the second in the comprehensive evaluation on curative effect and market. Statistical data indicate that, among all chemotherapy regimens in China, more than 70%~80% are dominated by platinum or compatible with platinum drugs.

Platinum antitumor drugs, however, now with high toxicity, has many defects, including bone marrow suppression, nephrotoxicity, nerve injury, etc., poor solubility, comparatively narrow anticancer spectrum, drug resistance, etc. Therefore, designing and synthesizing new platinum antitumor drugs remains one of the leading directions for the present antitumor drug research (M. A. Jakuper, M. Galanski, B. K. Keppler. Tumor-inhibiting platinum complexes-state of art and future perspectives, Rev. Physiol Biochem Pharmacol, 2003, 146, 1-53).

Substantive studies have been conducted in recent two years to reduce the toxic and side effects of platinum chemotherapy drug, improve curative effect, reduce tumor recurrence and avoid drug resistance, and improve the water solubility of platinum compound. For example, the solubility of cisplatin is 2.65 mg/ml. Later the solubility of Oxaliplatin is 7.9 mg/ml; the solubility of Carboplatin is 17.8 mg/ml; that of Minoplatin is 27 mg/ml. Comparing with cisplatin, the toxic and side effects of Oxaliplatin and Carboplatin are reduced. The deficiency is that the solubility of above socalled water-soluble platinum compounds remain slight soluble or sparingly soluble. Murray A. Plan et al prepared the sodium alcoholate salt for platinum compound, effectively improved the solubility externally (U.S. Pat. No. 4,322,362A), but the compound must be dissolved under the condition above pH10 and the toxicity has still not been effectively solved. Giulia C et al also prepared series of platinum compounds. However, the solubility of those compounds was still not remarkably improved (Chem Med Chem, 2009, 4(10), 1677-1685). WO2006091790A1 also made public a series of platinum compounds with specific structure, but similarly, the solubility was still not distinctively improved.

SUMMARY OF THE INVENTION

The present invention provides a class of platinum compounds used for the treatment of proliferating diseases, in particular platinum compounds with the leaving group of malonic acid derivative containing amino and alkylamino radical, their pharmaceutical acceptable salts, solvates, stereoisomers or their prodrugs. Comparing with the existing platinum antitumor drugs, the aqueous solubility of the compounds in the invention has been greatly improved, and the toxicility and side effects have been significantly reduced, and unexpected technical effects have been produced. The compounds is showed in formula A:

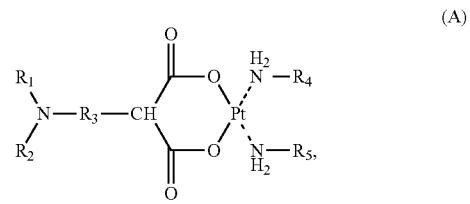

(A)

Wherein:

$R_1$ and $R_2$ may be the same or different, including but not limited to hydrogen, alkyl, naphthenic base, alkoxy alkyl, alkyl amino alkyl, heterocycle, alkenyl, alkynyl; wherein hydrocarbyl, alkoxy alkyl, alkyl amino alkyl and heterocycle may be unsubstituted or optionally substituted, preferably substituted by halogen, hydroxyl, alkoxy, alkyl, alkoxy alkyl, naphthenic base, heterocycle, provided that $R_1$ or $R_2$ contains unsaturated bond, the atom of the unsaturated bond cannot be directly connected with nitrogen atom.

$R_3$ may be but not limited to alkyl, naphthenic base, $—R_{31}—O—R_{32}—$; $R_{31}$ and $R_{32}$ are independently selected from bond or alkyl; $R_{31}$ is connected with nitrogen atom, provided that $R_{31}$ contains unsaturated bond, the atom of the unsaturated bond cannot be directly connected with above nitrogen atom; the alkyl or naphthenic base described above may be unsubstituted or optionally substituted, preferably substituted by halogen, hydroxyl, alkoxy, alkyl, alkoxy alkyl, naphthenic base, heterocycle;

$R_4$ and $R_5$ may be the same or different, may be but not limited to hydrogen, hydroxyl, alkyl, naphthenic base, alkoxy, alkoxy alkyl, heterocycle, alkenyl, chain alkynyl; wherein alkyl, alkenyl, chain alkynyl naphthenic base, alkoxy alkyl, alkyl amino alkyl and heterocycle may be unsubstituted or optionally substituted, preferably substituted by halogen, hydroxyl, alkoxy, straight chain or branched-chain alkyl, alkoxy alkyl, naphthenic base, heterocycle;

$R_4$, $R_5$ and the atoms connected with them may form a closed ring. For example, the closed ring may be quaternary, pentabasic, hexabasic, heptabasic or octatomic ring; the above rings may be optionally condensed with other rings and may be optionally substituted.

Preferably, $R_1$ and $R_2$ are selected from hydrogen, $C_{1-8}$ alkyl, naphthenic base, alkoxy alkyl, alkyl amino alkyl, or heterocycle; $R_3$ may be but not limited to $C_{2-10}$ alkyl, naphthenic base; $R_4$ and $R_5$ are selected from hydrogen, hydroxyl, $C_{1-8}$ alkyl, naphthenic base, alkoxy, alkoxy alkyl, or heterocycle.

More preferably, the present invention provides compounds of formula B and their pharmaceutically acceptable salts:

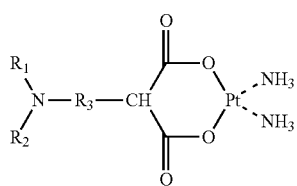

(B)

Wherein $R_1$, $R_2$, $R_3$ are as described above.

Most preferably, $R_1$ and $R_2$ are hydrogen, methyl, ethyl or propyl; $R_3$ is ethyl or propyl.

The present invention further provides compounds of formula C and their pharmaceutically acceptable salts, i.e. The compounds obtained when $R_4$, $R_5$ and their connected atoms form a closed ring together. The structural of formula C is as follows:

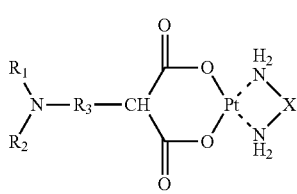

(C)

Wherein, the group where $R_1$, $R_2$, $R_3$ are selected as described above,

is but not limited to the groups below:

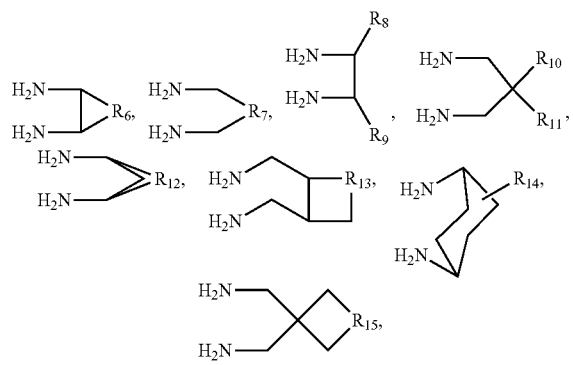

and the groups above may also be optionally connected with various appropriate substituted groups.

The platinum complex in formula C, wherein $R_6$ may be but not limited to $(CH_2)_n$; wherein n=1-6, preferably 3-5, the most preferably 4; wherein some $—CH_2—$ may be substituted by $—O—$. One or more hydrogens of $(CH_2)_n$ may be substituted by halogen, alkyl, hydroxyl or alkoxy, etc., preferably compound is selected from (±) trans-1,2-cyclohexane diamine platinum (II), (±) trans-1,2-cyclopentamethylene diamine platinum (II), (f) trans-1,2-cyclobutanediamine platinum (II) and (±) trans-1,2-cyclopropane diamine platinum (II). $R_7$ may be but not limited to $(CH_2)_n$, wherein n=0-3, preferably n=0-2; wherein some $—CH_2—$ may be substituted by $—O—$, and one or more hydrogen of $(CH_2)_n$ may be substituted by halogen, alkyl, hydroxyl, hydroxyalkyl or alkoxy, etc. $R_8$ and $R_9$ may be but not limited to hydrogen, halogen, hydroxyl, hydroxyalkyl, alkyl, alkoxy, heterocycle, etc. $R_5$ and $R_9$ may be the same or different, preferably hydroxymethyl (F). $R_{10}$ and $R_{11}$ may be but not limited to hydrogen, halogen, hydroxyalkyl, alkyl, alkoxy, heterocycle, etc. $R_1$ and $R_2$ may be the same or different, preferably hydroxymethyl. $R_{12}$ may be but not limited to $(CH_2)_n$, wherein n=2-4, wherein some $—CH_2—$ may be substituted by $—O—$. One or more hydrogen of $(CH_2)_n$ may be substituted by halogen, alkyl, hydroxyl or alkoxy, etc. $R_{13}$ may be $—CH_2—$ or $—O—$, preferably $—CH_2—$. $R_{14}$ may be hydrogen, halogen, alkyl, alkoxy, hydroxyalkyl or hydroxyl. $R_{14}$ is preferably hydrogen. $R_{15}$ may be but not limited to $—CH_2—O—$, $—O—$ or $(CH_2)_n$, wherein n=1-3; one or more hydrogen of $(CH_2)$ may be substituted by alkyl, alkoxy, hydroxyl, or hydroxyalkyl, etc. $R_{15}$ is preferably $—CH_2—O—CH_2—$.

Preferably, the structure of compounds is as follows:

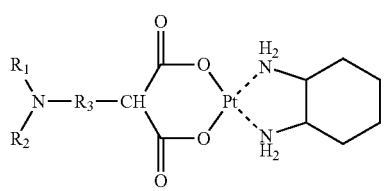

(D1)

-continued

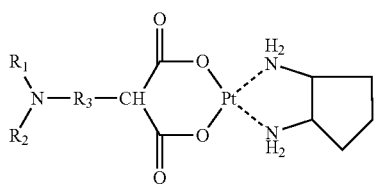
(D2)

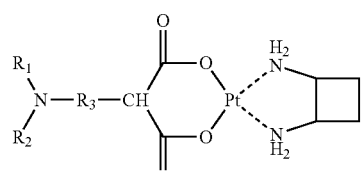
(D3)

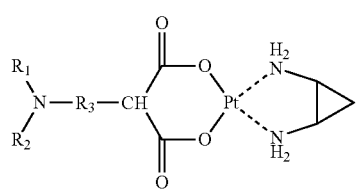
(D4)

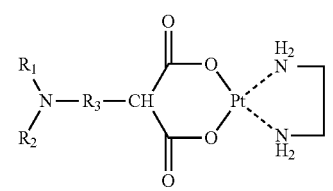
(E1)

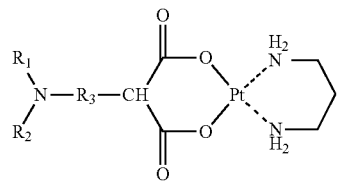
(E2)

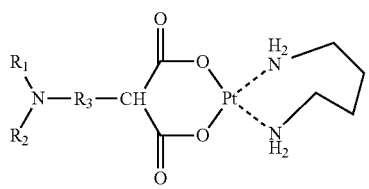
(E3)

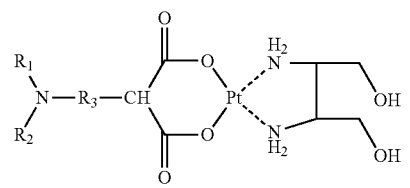
(F)

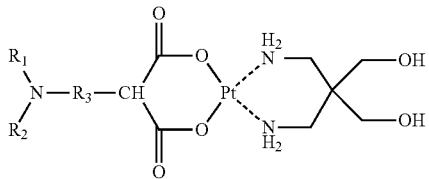
(G)

-continued

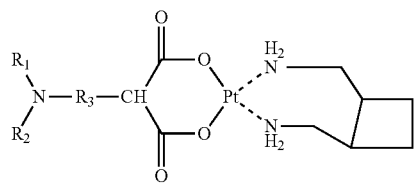
(H)

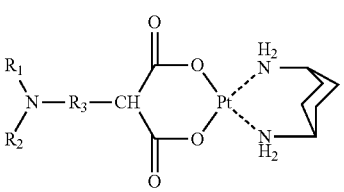
(I)

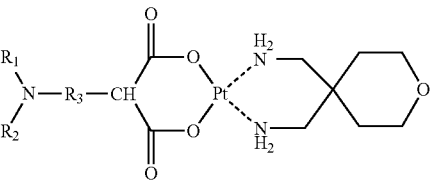
(J)

The most preferred compounds of the present invention include the following compounds.

Compound 1: [2-(2-methylamino ethyl)-malonato].[Cis-diamine] platinum (II);
Compound 2: [2-(2-dimethylamino ethyl)-malonato].[Cis-diamine] platinum (II);
Compound 3: [2-(3-dimethylamino propyl)-malonato].[Cis-diamine] platinum (II);
Compound 4: [2-(3-amino propyl)-malonato].[Cis-diamine] platinum (II);
Compound 5: [2-(2-diethylamino ethyl)-malonato].[Cis-diamine] platinum (II);
Compound 6: [2-(3-diethylamino propyl)-malonato].[Cis-diamine] platinum (II);
Compound 7: [2-(2-di-n-propylamino ethyl)-malonato].[Cis-diamine] platinum (II);
Compound 8 [2-(3-di-n-propylamino propyl)-malonato].[Cis-diamine] platinum (II);
Compound 9: [2-(2-amino ethyl)-malonato].[cis-(1, 2-trans-cyclohexane diamine)] platinum (II);
Compound 10: [2-(2-dimethylamino ethyl)-malonato].[cis-(1,2-trans-cyclohexane diamine)] platinum (II);
Compound 11: [2-(3-dimethylamino propyl)-malonato].[cis-(1,2-trans-cyclohexane diamine) ]platinum (II);
Compound 12: [2-(2-ethylamino ethyl)-malonato].[cis-(1,2-trans-cyclohexane diamine) ]platinum (II);
Compound 13: [2-(2-diethylamino ethyl)-malonato].[cis-(1, 2-trans-cyclohexane diamine)] platinum (II);
Compound 14: [2-(3-diethylamino propyl)-malonato].[cis-(1,2-trans-cyclohexane diamine)] platinum (II);
Compound 15: [2-(2-di-n-propylamino ethyl)-malonato].[cis-(1,2-trans-cyclohexane diamine)] platinum (II);
Compound 16: [2-(3-di-n-propylamino propyl)-malonato].[cis-(1,2-trans-cyclohexane diamine)] platinum (II);
Compound 17: [2-(3-diethylamino propyl)-malonato].[cis-(1, 2-trans-dicyclopentyl amine) ]platinum (II);
Compound 18: [2-(3-diethylamino propyl)-malonato].[cis-(1, 2-trans-cyclobutyl diamine) ]platinum (II);
Compound 19: [2-(3-diethylamino propyl)-malonato].[cis-(1, 2-trans-cyclopropyl diamine)] platinum (II);

Compound 20: [2-(2-dimethylamino ethyl)-malonato].[cis-1, 2-ethyldiamine] platinum (II);

Compound 21: [2-(2-diethylamino ethyl)-malonato].[cis-1, 3-propyl diamine] platinum (II);

Compound 22: [2-(2-di-n-propylamino ethyl)-malonato].[cis-1,4-butyldiamine] platinum (II);

Compound 23: [2-(2-diethylamino ethyl)-malonato].[cis-1, 2-(1,2-dihydroxymethylene)-ethyldiamine] platinum (II);

Compound 24: [2-(2-dimethylamino ethyl)-malonato].[cis-1, 3-(2, 2-hydroxymethyl)-propyl diamine] platinum (II);

Compound 25: [2-(2-dimethylamino ethyl)-malonato].[cis-1,4-(trans-2,3-cyclobutyl)-butanediamine platinum (II);

Compound 26: [2-(2-diethylamino ethyl)-malonato].[cis-1, 4-(trans-2,3-cyclobutyl)-butanediamine] platinum (II);

Compound 27: [2-(2-diethylamino ethyl)-malonato].[cis-1, 4-cyclohexyane diamine] platinum (II);

Compound 28: [2-(2-diethylamino ethyl)-malonato].[cis-1, 3-(2, 2-(4-oxacyclohexyl))-propyl diamine] platinum (II);

Compound 29: [2-(3-(1-piperidyl)-propyl)-malonato].[cis-diamine] platinum (II);

Compound 30: [2-(3-(1-pyrrolidyl)-propyl)-malonato].[cis-diamine] platinum (II).

The following are the definitions of various terms used in the description of the present invention. Unless limited in special case, the following terms are applicable to the entire description and claims (independently or as a part of larger group).

The term "alkyl" refers to 1-20 unsubstituted saturated carbon atoms of straight chain or branched-chain, preferably alkyl groups containing 1-7 carbon atoms, most preferably, unsubstituted alkyl groups containing 1-4 carbon atoms.

The term "substituted alkyl" refers to, for example, the alkyl substituted by 1-4 of the following substituent groups: such as halogen, trifluoromethyl, trifluoromethoxyl, hydroxyl, alkoxy, cycloalkyloxy, heterocyclic oxygroup, oxo, alkane acyl, aryloxy, alkane acyl oxygen radical, amino, alkylamino, arylamine, aralkyl amido, naphthene amido, heterocyclic amido, substituent tertiary amine (wherein 2 nitrogen substituent groups are selected from alkyl, aryl or aralkyl); alkane acyl amido, aroyl amino, aryl alkane acyl amido, substituent alkane acyl amido, substituent aromatic amino, substituent aryl alkane acyl, thiodiglycolic, alkyl sulfonium, aryl sulfonium, aralkyl sulfonium, naphthenic sulfonium, heterocyclic sulfonium, alkyl carbonyl sulfur, aryl carbonyl sulfur, aromatic alkyl carbonyl sulfur, alkyl sulfonyl, aryl sulfonyl, aromatic alkyl sulfonyl, sulfonamido, such as $SO_2NH_2$, substituted sulfonamide, nitryl, cyano, carboxyl, carbamyl, such as $CONH_2$, substituted carbamyl such as $CONH$ alkyl, $CONH$ aryl, $CONH$ aralkyl or when two substituent groups exist on nitrogen, selected from alkyl, aryl or aralkyl; alkoxy carbonyl, aryl, substituent aryl, guanidyl and heterocyclic radical, such as indolyl, imidazolyl, furyl, thienyl, thiazolyl, pyrrolidyl, pyridyl, pyrimidyl, etc. The above substituted groups may be further substituted by halogen, alkyl, alkoxy, aryl or aralkyl.

The term "halogen" or "halogenate" refers to fluorine, chlorine, bromine, and iodine.

The term "aryl" refers to monocyclic or dicyclic aromatics containing 6-12 carbon atoms in ring, such as phenyl, naphthyl, biphenyl and diphenyl. The above "aryl" may be substituted.

The term "aralkyl" refers to the aryl combined directly through alkyl group, such as benzyl.

The term "substituent aryl" refers to the aryl substituted by 1-4 of the following substituent groups: Such as alkyl, substituent alkyl, halogen, trifluoromethoxy, trifluoromethyl, hydroxyl, alkoxy, cycloalkyloxy, heterocyclic oxygroup, alkane acyl, alkane acyl oxygen radical, amino, alkylamino, aralkyl amido, naphthene amido, heterocyclic amido, dialkyl amino, alkane acyl amido, thiol, alkyl sulfo, naphthenic base sulfo, heterocycle sulfo, carbamido, nitryl, cyano, carboxyl, carboxyl alkyl, formamyl, alkoxy carbonyl, alkyl carbonyl sulfur, aryl carbonyl sulfur, alkyl sulfonyl, sulfonamido, aryloxy, etc. The said substituent group may be further substituted by halogen, hydroxyl, alkyl, alkoxy, aryl, substituent aryl, substituent alkyl or substituent aralkyl.

The term "alkenyl" refers to the straight chain or branched-chain alkyl group with 1-4 ethylenic bonds containing 2-20 carbon atoms, preferably 2-15 carbon atoms, most preferably 2-8 carbon atoms.

The term "substituent alkenyl" refers to the alkenyl group substituted by, for example, 1-2 of the following substituent groups: such as halogen, hydroxyl, alkoxy, alkane acyl, alkane acyl oxygen radical, amino, alkylamino, dialkyl amino, alkanoyl amido, thiodiglycolic, alkyl sulfo, alkyl carbonyl sulfur, alkyl sulfonyl, sulfonamido, nitryl, cyano, carboxyl, formamyl, substituted formamyl, guanidyl and heterocyclic radical, such as indolyl, imidazolyl, furyl, thienyl, thiazolyl, pyrrolidyl, pyridyl, pyrimidyl, etc.

The term "alkynyl or chain alkynyl" refers to the straight chain or branched-chain alkyl group with 1-4 acetylenic bonds containing 2-20 carbon atoms, preferably 2-15 carbon atoms, most preferably 2-8 carbon atoms.

The term "substituent alkenyl" refers to the alkenyl substituted by, for example, one of the following substituent groups: halogen, hydroxyl, alkoxy, alkane acyl, alkane acyl oxygen radical, amino, alkylamino, dialkyl amino, alkane acyl amido, thiodiglycolic, alkyl sulfo, alkyl carbonyl sulfur, alkyl sulfonyl, sulfonamido, nitryl, cyano, carboxyl, formamyl, substituted formyl amino, guanidyl and heterocyclic radical, such as imidazolyl, furyl, thienyl, thiazolyl, pyrrolidyl, pyridyl, pyrimidyl, etc.

The term "naphthenic base" refers to optionally substitutive, saturate hydrocarbon ring system preferably containing 1-3 rings and each (may be further condensed with unsaturated $C_3$-$C_7$ carbonatomic ring) containing 3-7 carbon atoms. Example groups include cyclopropyl, cyclobutyl, cyclopentyl, cyclohexyl, cycloheptyl, cyclo-octyl, cyclodecyl, cyclic dodecyl and adamantyl. Example for substituent group includes one or more of alkyl groups as described above, or one or more of alkyl substituent groups as described above.

The terms "heterocycle", "heterocyclic", and "heterocyclic radical" refer to optionally substituted, completely saturated or incompletely saturated aromatic or non-aromatic ring group, for example, the said ring is 4-7-membered monocyclic, 7-11-membered dicyclic or 10-15-membered tricyclic system, containing at least one heteroatom on the ring at least containing on carbon atom. There may be 1, 2, 3 or 4 heteroatoms selected from nitrogen atom, oxygen atom and sulphur atom on each ring of heterocyclic group containing heteroatom, wherein the said nitrogen and sulphur heteroatom may also be optionally oxidized and nitrogen heteroatom may also be optionally quaternized. The said heterocyclic group may be connected on any heteroatom or carbon atom.

Example monocyclic heterocyclic group includes pyrrolidyl, pyrryl, indolyl, pyrazolyl, oxa-cyclobutyl group, pyrazolinyl, imidazolyl, imidazolinyl, imidazolidinyl, oxazolyl, oxazolidinyl, isoxazolinyl, isoxazolyl, thiazolyl, thiadiazole, oxazolidinyl, isoxazolinyl, isoxazolyl, furyl, tetrahydrofuran, thienyl, oxadiazol, piperidyl, piperazinyl, 2-oxo-piperazinyl, 2-oxo-piperidyl, 2-oxo-pyrrolidyl, 2-oxopazepine, azepine, 4-piperidone, pyridyl, N-oxo-pyridyl, pyrazinyl, pyrimidyl, pyridazinyl, tetrahydrothiopyran, tetrahydropyrane, morpholinyl, thiamethoxam morpholinyl, thiamethoxam morpholine sulfoxide, tetrahydrothiopyran sulfoxide, thiamethoxam morpholinyl sulfoxide, 1,3-dioxolame and tetralin-1,1-dioxo thienyl, dioxane, isoxazolyl, thia cyclobutyl, thia cyclopropyl, triazinyl and triazolyl, etc.

Example bicyclic heterocyclic group includes benzothiazolyl, benzoxazolyl, benzothiophene, quinuclidinyl, quinolyl, quinolyl-N-oxide, tetrahydroisoquinol, isoquinolyl, benzimidazolyl, benzopyranyl, indolizine, benzopyranyl, chromone, aryl coumarin, 1,2-phthalazine, quinoxaline, indazolyl, pyrrolo and pyridyl, furan and pyridyl (such as furan and [2,3-c]pyridyl, furan and [3,1-b]pyridyl or furan and [2,3-b]pyridyl), isoindolinyl, dihydrogen quinazoline (such as 3,4-dihydro-4-oxo-quinazolinyl), benzisothiazol, benzisoxazole, benzodiazine, benzopyranyl, benzothiopyran, benzodiazine, benzofuryl, thiochroman, thiochroman sulphone, chroman, chroman sulphone, dihydrobenzene benzopyranyl, indolinyl, isobenzopyran, isoindolinyl, 1,5-phthalazine, 2,3-phthalazine, 3,4-methylenedioxy benzyl, purine, pyridine-pyridy, quinazolinyl, tetralinquinolyl, thiophene-furan, thiophene-pyridine, thiophene-thienyl, etc.

Smaller heterocycles, such as epoxide and aziridine, are also included.

The term "heteroatom" includes oxygen, sulphur and nitrogen.

The term "pharmaceutically acceptable salt" includes the active compound salt prepared with relatively nontoxic acid or alkali on the basis of the specific substituent group existed on the compound as described in this invention. When the compound in the invention contains relatively acidic functional group, alkali addition salt can be obtained by enabling the compound in neutral form to contact sufficient necessary with alkali directly or in appropriate inert solvent. Examples of pharmaceutical acceptable inorganic alkali salt derivatives include aluminum, ammonium, calcium, copper, ferric iron, ferrous, lithium, magnesium, manganese, bivalent manganese, potassium, sodium, zinc, etc. Pharmaceutical acceptable organic base salt derivatives include primary, secondary and tertiary amine salts; they include substituent amine, cyclammonium, amine, etc., such as arginine, glycine betaine, caffeine, choline, N,N'-dibenzyl ethylenediamine, diethylamine, 2-diethyl aminoacyl alcohol, 2-dimethyl aminoacyl alcohol, cholamine, ethylenediamine, N-ethyl morpholine, N-ethyl piperidine, glucosamine, glucamine, histidine, hydrabamine, isopropamide, lysine, methylglucosamine, morpholine, piperazine, piperidine, polyamino resin, procaine, purine, theobromine, triethylamine, trimethylamine, tripropylamine, tromethamine, etc. When the compound of the prevent invention contains relatively alkali functional group, acid addition salt can be obtained by enabling the compound in neutral form to contact sufficient required acid directly or in appropriate inert solvent. Examples of pharmaceutical acceptable acid addition salts include salts derived from inorganic acid, such as nitrate, carbonate, bicarbonate, phosphate, hydrophosphate, dihydric phosphate, sulphate, bisulfate, phosphite, hydrochloride, hydrobromide, hydriodate, etc.; salt derivated from relative nontoxic organic acid, for example, acetic acid, propionic acid, isobutyric acid, malonic, benzoic acid, succinic acid, suberic acid, fumaric acid, mandelic acid, phthalic acid, benzenesulfonic acid, p-toluenesulfonic acid, citric acid, tartaric acid, methanesulfonic acid, etc.; and also include arginine acid, for example, arginine salt and organic acid such as glucuronic acid or galactonic acid salts; preferably nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactose acid salt.

In some embodiments in the present invention, the leaving group of compounds in the present invention contains basic group(s) that may form salt with acid and platinum (II) complex salts are prepared with the method well known to the technical person in this field. For example, it may form mesylate, trifluoromethanesulfonic salt with lower alkyl sulfonic acid, such as methanesulfonic acid, trifluoromethanesulfonic acid, etc.; form tosilate, benzene sulfonate, camphosulfonate with arylsulphonate, such as benzenesulfonic acid or p-toluenesulfonic acid, etc; form appropriate salts with organic carboxylic acid, such as acetic acid, fumaric acid, tartaric acid, oxalate, maleic acid, malic acid, succinic acid, lactic acid or citric acid, etc.; may form glutamate or aspartate with arginine acid, such as glutamic acid or aspartic acid; form appropriate salts with inorganic acid, such as nitric acid, carbonic acid, sulfuric acid or phosphoric acid, etc. The acid that may be used include organic acid, inorganic acid, etc.

The compounds of the present invention may be interconverted with their salt form through the conventional method in this field. For example, free bases can be obtained by separation in conventional way after the contacting between salts and alkali or acid, or the form of salts can be obtained by separation in conventional way by adding acid or alkali to the compounds. Some physical properties of the free bases, such as the solubility in polar solvent, are different from various salt forms; however, for the purpose of the present invention, salts and the compounds in parent form have the same antitumor effect.

In addition to the salt form, the present invention may provide the compounds in the form of prodrug esters. The "prodrug(s)" of the compounds as described in this invention refers to the compounds that are prone to chemical change in physiological environment to obtain the compounds of the present invention. In addition, prodrugs can be converted into the compounds of the present invention with chemical or biochemical methods in separation environment. For example, when placed in the transdermal patch reponsitory containing appropriate enzyme or chemical reagent, prodrugs may be slowly converted into the compounds of the present invention. Prodrugs are usually pharmacological inert compounds before converting into active drugs; however, this situation is not necessary. Usually, the functional group required by the activity in drug is concealed with "precursor group" (as defined below), releasing functional group through conversion (such as cracking in specific operating condition) and obtaining the "precursor part" of active drug and prodrug. Precursor part may be catalyzed or induced through such as hydrolysis reaction, or through another actor (such as enzyme, light, acid or alkali) or change of physical or environmental parameter (such as change of temperature) or exposing physical or environmental parameters for spontaneous cracking. Comparing with operating environment, actor may be endogenic, for example, the enzyme existed in the cell where prodrug is given or the acidic environment of gastro or provided from external source.

"Precursor Group" refers to a sort of protective group that can convert drug into prodrug when the functional group used in covering active drug forms "precursor part". Precursor group is usually connected with the functional group of drug through bond. The said bond can be cracked in specific condition. Therefore, precursor group is a part of precursor part. The said precursor part is cracked in specific operating condition and releases functional group. As a specific example, the amide precursor part of the formula —NH—C(O)CH$_3$ contains precursor group —C(O)CH$_3$.

It is well known in the art that a wide variety of precursor groups and the part of precursorssuitably conceal the functional group in active compounds to obtain prodrugs. For example, hydroxyl functional group may become suphonate, ester (such as acetic acid ester or maleic acid ester) or carbonic acid ester precursor part by concealing. This precursor part may be hydrolyzed in the body, to obtain hydroxyl. Carboxyl can be covered into ester (including methyl, ethyl, pivaloyl acyloxy methyl, silicyl ester and sulpho acid ester), amide or hydrazide precursor part. They can be hydrolyzed in body to obtain carboxyl. The present invention includes the known esters and acyls used for change of solubility or hydrolysis property in the field, used as controlled-release or prodrug preparation. For one skilled in the art, the specific examples of appropriate precursor groups and their appropriate precursor parts are obvious.

Some compounds of the present invention may exist in the form of non-solvation and solvation including hydration. "Solvate" refers to the compound generated from the combination of solvent molecule with the molecule or ion of solute. Solvent may be organic compound, inorganic compound or the mixture of both. Some examples of solvent include but not limited to carbinol, N, N-dimethyl formamide, tetralin furan, dimethylsulfoxide, and water. Generally, solvent form is equivalent to non-solvent form and included in the range of the present invention. Some compounds of the present invention may exist in the form of polymorph or smorphism. In general, for the assumed usage of the present invention, all physical forms are the same and included in the range of the present invention.

Some compounds of the present invention have asymmetric carbon atom (rotophore) or double bond; their raceme, non-enantiomer, geometric isomer, regional isomer and individual isomer (such as separated enantiomer) are included in the range of the present invention. Those isomers may be split or asymmetrically synthesized with conventional method to make isomer "optical pure", i.e., not containing other isomers on the whole. For example, if particular enantiomer of the compound of the present invention is required, pure required enantiomer can be obtained through asymmetric synthesis preparation or through chiral auxiliaries derivatization, wherein splitting the mixture of diasteromer obtained and cracking the assistant group, or when the molecule contains alkali functional group such as amino or acidic functional group such as carboxyl, appropriate optical active acid or alkali may be used for forming asymmetric heterogeneous salt, then splitting the non-enantiomer formed hereof through fractional crystallization or chromatographic process well-known in this field, finally pure enantiomer is recovered.

The compound of the present invention may contain the isotope of the atom in abnormal proportion in one or more atoms constituting the compound. For example, the compound may be labeled with radioisotope such as tritium ($^3$H), iodine –125($^{125}$I) or carbon –14($^{14}$C). Regardless of whether it has radioactivity or not, all isotope forms of the compound of the present invention are all included in the range of the present invention.

Another purpose of the present invention is to provide the preparation methods for the foregoing compounds.

I. The preparation method for the formula (A) is provided as follows:

(1) Potassium chloroplatinite was added into water and the mixture was stirred to form solution at room temperature; potassium iodide was put into above potassium chloroplatinite solution to react with shielded nitrogenand gas away from light and oxygen in water bath condition;

(2) R$_4$NH$_2$ was dissolved in distilled water and added dropwise into the reaction liquid in (1); the mixture was reacted in water bath condition;

(3) After cooling down above the reaction mixture below room temperature, R$_5$NH$_2$ was dissolved in distilled water and then added dropwise to the reaction mixture (2) to react in water bath; yellow deposit in large quantity was generated in the mixture; after cooling down the mixture below room temperature; diiodo diamine platinum (II) was obtained through suction filtration and washing.

(4) Ag$_2$SO$_4$ was added in water and stirred; in water; diiodo diamine platinum (II) was added into reaction mixture and then water was added; the mixture was stirred in water bath condition away from light and oxygen with shielded nitrogenand gas; dihydrol diamine platinum (II).sulphate was obtained by suction;

(5) Putting diethyl malonate, Br—R$_3$—Br, K$_2$CO$_3$ and tetrabutylammonium bromide into flask the mixture was heated and stirred; after removal of solid by suction and washing, filtrate was collectted in vacuo after removal of solvent;

(6) 2-Br—R$_3$-diethyl malonate and anhydrous K$_2$CO$_3$ was added in acetonitrile and stirring; R$_1$—NH—R$_2$ was added into reaction mixture; the mixture was heated and stirred; filtering out insoluble substance of the mixture; the filtrate was pumped dry and residue was dissolved in organic solvent; the organic phase was washed with aqueous solution and dried; after removal of solvent in vocuo; the product was obtained by purifying through column chromatography.

(7) NaOH solution was added into the product in (6) and stirred at room temperature.

(8) After treating the product in (7) with acid solution, the product in above (4) was added, the mixture was heated to afford the platinum compound of the present invention.

The Preferable preparation method is as follows:

(1) Stirring potassium chloroplatinite in water at room temperature; potassium iodide solution of water was added into above potassium chloroplatinite solution. The mixture was stirred away from light and oxygen in water bath at 40~60° C.

(2) R$_4$NH$_2$ solution of water was added dropwise to the reaction mixture in (1) to react in water bath at 40~60° C.;

(3) Cooling down reaction mixture below 20° C., R$_5$NH$_2$ aqueous solution was added dropwise into the reaction mixture in (2) to react in water bath for 30~60 min at 40~60° C.; there will be yellow deposit in great quantity; after cooling down below 20° C., diiodo diamine platinum (II) was obtained by suction and washing with water, anhydrous ethanol, and diethyl ether in turn.

(4) Stirring Ag$_2$SO$_4$ in water, above diiodo diamine platinum (II) was put into reaction mixture and then water was added; the mixture was stirred away from light and oxygen at 40~60° C.; dihydrol diamine platinum (II).sulphate was obtained after suction filtration.

(5) Putting diethyl malonate, Br—R$_3$—Br, K$_2$CO$_3$ and tetrabutylammonium bromide into flask the mixture was heated and stirred; after removal of solid by suction and washing, filtrate was washed and dried over MgSO4; distillate was collectted in vacuo after removal of solvent;

(6) Stirring 2-Br—R$_3$-diethyl malonate and anhydrous K$_2$CO$_3$ in acetonitrile; R$_1$—NH—R$_2$ was added into reaction mixture; the mixture was heated and stirred; filtering out insoluble substance of the mixture; the filtrate was pumped dry and added, organic solvent for dissolution; the organic phase was washed with aqueous solution and dried; after removal of solvent in vocuo, the product was obtained by purifying (through column chromatography).

(7) NaOH solution was added into the product in (6) and stirred at room temperature.

(8) After treating the product in (7) with acid solution, the product in above (4) was added, the mixture was heated to afford the platinum compound of the present invention.

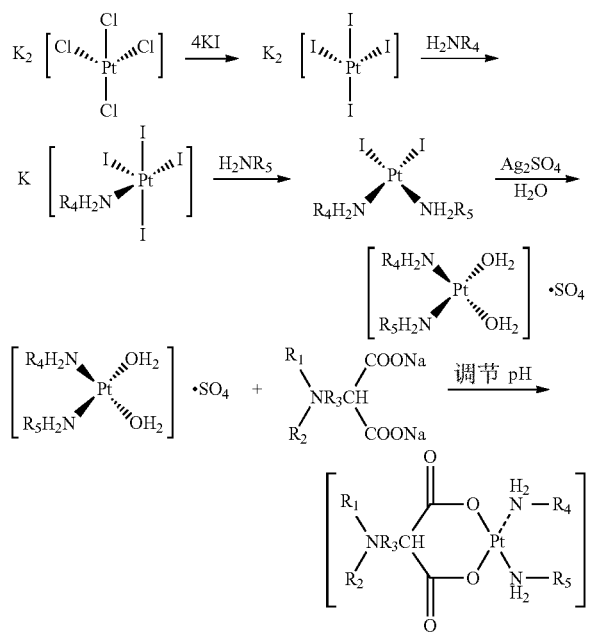

II. The preparation method in the formula (B) is as follows:

(1) Potassium chloroplatinite was added in water and stirred at room temperature; potassium iodide solution of water was added into above potassium chloroplatinite solution. The mixture was stirred away from light and oxygen in water bath;

(2) Bidentate ammonia $NH_2$—X—$NH_2$ aqueous solution was added dropwise into the reaction mixture in (1) to react in water bath; yellow deposit in great quantity was afforded; after coolling down the mixture below room temperature, bidentatediiodo diamine platinum (II) was obtained by suction and washing (3) $Ag_2SO_4$ was added in water and stirred, above bidentatediiodo diamine platinum (II) was put into reaction mixture and then water was added; the mixture was stirred away from light and oxygen; dihydrol diamine platinum (II) sulphate was obtained after suction filtration.

(4) Putting diethyl malonate, Br—$R_3$—Br, $K_2CO_3$ and tetrabutylammonium bromide into flask the mixture was heated and stirred; after removal of solid by suction and washing, filtrate was washed and dried over MgSO4; distillate was collectted in vacuo after removal of solvent;

(5) Stirring 2-Br—$R_3$-diethyl malonate and anhydrous $K_2CO_3$ in acetonitrile; $R_1$—NH—$R_2$ was added into reaction mixture; the mixture was heated and stirred; filtering out insoluble substance of the mixture; the filtrate was pumped dry and added, organic solvent for dissolution; the organic phase was washed with aqueous solution and dried, after removal of solvent in vocuo; the product was obtained by purifying through column chromatography.

(6) NaOH solution was added into the product in (5) and stirred at room temperature.

(7) After treating the product in (6) with acid solution, the product in above (3) was added, the mixture was heated to afford the platinum compound of the present invention.

The Preferred preparation method is as follows:

(1) Potassium chloroplatinite was added in water and stirred at room temperature; potassium iodide solution of water was added into above potassium chloroplatinite solution. The mixture was stirred away from light and oxygen in water bath at 40~60° C.

(2) Bidentate ammonia $NH_2$—X—$NH_2$ aqueous solution was added dropwise into the reaction mixture in (1) to react in water bath for 40~60° C.; yellow deposit in great quantity was afforded; after coolling down the mixture below 20° C., bidentatediiodo diamine platinum (II) was obtained by suction and washing.

(3) Stirring $Ag_2SO_4$ in water, above bidentatediiodo diamine platinum (II) was put into reaction mixture and then water was added; the mixture was stirred away from light and oxygen at 40~60° C.; dihydrol diamine platinum (II).sulphate was obtained after suction filtration.

(4) Putting diethyl malonate, Br—$R_3$—Br, $K_2CO_3$ and tetrabutylammonium bromide into flask the mixture was heated and stirred; after removal of solid by suction and washing, filtrate was washed and dried over MgSO4; distillate was collectted in vacuo after removal of solvent;

(5) Stirring 2-Br—$R_3$-diethyl malonate and anhydrous $K_2CO_3$ in acetonitrile; $R_1$—NH—$R_2$ was added into reaction mixture; the mixture was heated and stirred; filtering out insoluble substance of the mixture; the filtrate was pumped dry and added, organic solvent for dissolution; the organic phase was washed with aqueous solution and dried, after removal of solvent in vocuo; the product was obtained by purifying through column chromatography.

(6) NaOH solution was added into the product in (5) and stirred at room temperature.

(7) After treating the product in (6) with acid solution, the product in above (3) was added, the mixture was heated to afford the platinum compound of the present invention.

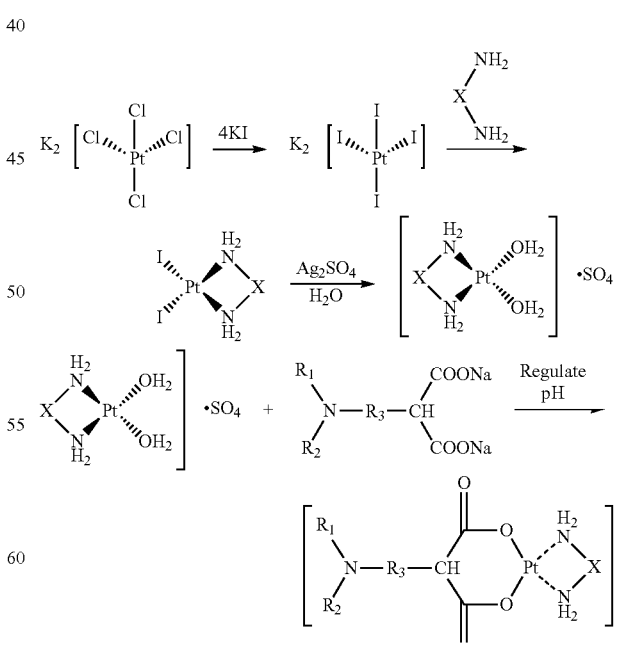

The present invention also provides a pharmaceutical composition containing above compound(s), its pharmaceutically acceptable salt, stereoisomer, prodrug or its solvate and pharmaceutical acceptable carriers. The composition contains approximately 0.01%-100%, preferably approximately 0.1%-100%, more preferably approximately 1%-100%, most preferably approximately 20%-100% (in weight) of one or more compounds of the present invention. The remaining part is composed of appropriate drug carrier(s) and/or excipient(s). The known method in this field and appropriate carrier may be used to form composition containing the compound of the present invention to match with administration route.

The quantity of the active compound in unit dose preparation may be between approximately 0.001 mg and approximately 1000 mg, preferably between approximately 0.01 mg and approximately 500 mg, and more preferably between approximately 1 mg and approximately 100 mg, and most preferably between approximately 10 mg and approximately 50 mg.

The administration may, for example, be oral, local, intravenous, subcutaneous, percutaneous, transdermal, intramuscular, intra-articular, parenteral, intra-arterial, intradermal, intraventricular, encephalic, intraperitoneal, within damage, intranasal, rectum, vagina, suction or through implantation repository. The term "parenteral" used in present invention includes subcutaneous, intravenous, intramuscular, intra-articular, within synovial fluid, within breast bone, intrathecal, intrhepatic, within damaged position and intracranial injection or target controlled infusion, preferably giving composition intravenously. The preparation of the prevent invention may be designed as quick-acting, immediate-release or long-acting. In addition, the compound may be administered locally other than in systemic way, such as giving (such as injecting) sustained release preparation. In accordance with the representative embodiment, the composites of the present invention may be prepared into the drug for mammal, preferably for human.

One or more composites containing in the prevent invention may be given repeatedly, for example, at least 2, 3, 4, 5, 6, 7, 8 or more times, or the composites may be given through continuous infusion. The appropriate positions of drug delivery include but not limited to blood vessel, muscle, skin, bronchus, intestines and stomach, anus, vagina, eye and ear. The preparation may adopt liquid dosage form, freeze-dry powder form, solid or semisolid, such as solution, suspension, emulsion, tablet, pill, capsule, powder, suppository, retention enema, cream, ointment, lotion, gel, aerosol, etc., preferably, the simple unit dosage form for delivering accurate dose.

For parenteral drug delivery, the composite may be in the form of sterile injection and aseptic packaging powder, preferably, preparing injection at pH value of approximately 4.5-7.5.

The composite of the present invention in sterile injection form are water or oil mixed suspension. Such suspension may be prepared with suitable dispersive or wetting agent and suspending agent according to the known technology in the field. Sterile injection preparation may be the sterile injection solution or suspension dissolved or suspended in nontoxic parenteral acceptable diluent or solvent, such as the solution dissolved in 1,3-butylene-glycol. Usable acceptable menstruum and solvent include water, Ringer's solution and other hypertonic sodium chloride solution. Additionally, sterile non-volatile oil is usually used as solvent or suspended substrate. Therefore, the nonvolatile oil of any brand including synthetic monoglyceride or diester can be used, similar to naturally pharmaceutical acceptable oil such as olive oil or castor oil, especially their polyethylene oxide ethylation form. Fatty acid such as oleic acid and its glyceride derivant can be used to prepare injection preparation. Such oil solution or suspension may also contain long-chain alcohol diluent or dispersing agent, such as carboxymethylcellulose or similar dispersing agent generally used in the preparation in pharmaceutical acceptance dosage form including emulsion and suspension. Other commonly used surfactants, such as Tween, Span, and the acceptable solid, liquid usually used for preparation pharmacy or other emulsifier or bioavailability promoter in other dosage form may be used for the purpose of preparation. Such compounds as those used for parenteral drug delivery, for example, through injection such as large dose injection or continuous infusion, may be prepared. Injection unit dosage form may be stored in ampoule or multiple-dose container.

The composites of the present invention in the form of freeze-drying may be provided. Such composites may include buffer agent used for redissolution before drug delivery, or freeze-drying composites may contain buffer agent, used for, for example, water redissolution. Freeze-drying composites may contain appropriate vasoconstrictor, such as epinephrine. Freeze-drying composites may be delivered through syringe, optionally packaged with the buffer agent used for redissolution, for the convenience to immediately delivering such redissolution composites to patients.

The medicinal composites of the present invention may also be used as any oral acceptable dosage form. They include tablet, capsule, cachet, emulsion, suspension, solution, syrup, elixir, spray, pill, lozenge, powder, granule and sustained release preparation. Appropriate excipients used for oral administration include medical Mannitol, lactose, starch, magnesium stearate, saccharin sodium, lcum powder, cellulose, glucose, gelatin, cane sugar, magnesium carbonate, etc. In case of the tablet used for oral administration, the common carriers include lactose and corn starch.

Generally, lubricant such as magnesium stearate may be added. In case of capsule, usable diluents include lactose and dry corn starch. When water suspension is required for oral medication, active ingredient shall be mixed with emulsified and suspending agents. Some sweetening agents, corrigents or colorants may be added according to the circumstances.

One or more compounds of the present invention and optionally one or more pharmaceutical acceptance auxiliary materials may be dissolved or dispersed on carriers such as salt aqueous solution, glucose aqueous solution, glycerol, ethanol, etc. to form, for example, oral, local or intravenous administered solution or suspension for preparing liquid compositions. Sterile liquid, such as oil, water, ethanol and their combination may be used for preparing the pharmaceutical preparations in the form of liquid suspension or solution.

For oral or parenteral drug delivery, pharmacy-suitable surfactant, suspending agent or emulsifier may be added. Suspension may contain oil, such as peanut oil, sesame oil, cottonseed oil, corn oil, and olive oil. Suspension preparation may also contain fatty acid ester, such as oleic acid ethyl ester, isopropyl myristate; fatty acid glyceride and acetyl fatty acid glyceride. Suspension preparations may include ethanol, such as alcohol, isopropanol, hexadecanol, glycerol and propylene glycol; ether such as poly(ethylene glycol); petroleum hydrocarbon, such as mineral oil and vaseline, and water can also be used for suspension preparation.

In some embodiments, the compositions adopt the form of pill, tablet or capsule. Therefore, the compositions may contain one or more diluents, such as lactose, cane sugar, dicalcium phosphate, etc; disintegrants, such as starch or their derivatives; lubricants, such as magnesium stearate, etc; and/or adhesives, such as starch, Arabic gum, polyvinylpyrrolidone, gelatin, cellulose, and their derivatives. Tablet may be prepared with any pressing or molding method known to the technical personnel in the field. Tablet may be prepared and pressed through pressing optionally the compounds of the present invention in the form of free flow mixed with auxiliary elements (such as adhesive, lubricant, diluent, disintegrant or dispersing agent) in suitable machine. Molding tablet may be prepared by molding powder mixture of the compound of the present invention with any suitable carrier in suitable machine.

Or the medicinal compositions of the present invention may be in the suppository form of rectal administration. Such suppositories may be prepared by mixing the drug with appropriate non-irritating excipient, which is solid under room temperature but is liquid under rectal temperature and thus release drug in rectum. Such materials include cocoa butter, beewax, polyethylene glycol, hard fat and/or hydrogenated coco-glyceride. The compositions suitable for rectal administration may also contain rectal enema unit. Such unit contains one or more compounds of the present invention and pharmaceutical acceptable menstruum (such as 50% ethanol aqueous solution or salt aqueous solution). Such menstruum is physiologically compatible with rectum and/or colon. Rectal enema unit contains the applicator tip protected by inert cover. This tip, preferably, is composed of polyethylene, lubricated with lubricant such as white vaseline, preferably protected by one-way valve, to prevent the backflow of the drug delivered. Rectal enema unit shall have sufficient length, preferably 2 inches, and inserted into colon via anus.

The medicinal compositions of the present invention may also be in the form of local drug delivery, especially when therapeutical target includes the region or organ locally accessible. The diseases of those organs include the diseases of eye, skin or lower intestinal tract. It is easy to prepare suitable topical preparation used for the regions or organs in those regions or organs. In case of topical administration, the compound of the present invention containing one or more composites may be in the form of emulsion, lotion, gel, foam, cream, gelatin, solution, suspension, ointment and transdermal patch.

Topical administration at lower intestinal tract can be realized through rectal suppository preparation or suitable enema preparation. Topical transdermal patch may be used as well. In case of topical application, the medicinal composition in appropriate ointment form may be prepared. Such ointment contains the active ingredient suspended on or dissolved in one or more carriers. The carriers used for the topical delivery of the compound of the present invention include but not limited to mineral oil, liquid Vaseline, white Vaseline, propylene glycol, polyoxyethylene, polypropylene oxide compound, emulsifying wax and water. Or the medicinal composition in appropriate lotion or cream form may be prepared. Such lotion or creation contains the active ingredients suspended on or dissolved in one or more pharmaceutical acceptable carriers. Suitable carriers include mineral oil, Span-60, Tween-60, cetyl, wax, cetanol, 2-octyldodecanol, benzyl alcohol and water.

The medicinal composites of the present invention may be delivered through nose aerosol or suction. In case of inhalation delivery, the composites in the form of dry powered or liquid may be delivered through sprayer. Such composites are prepared with the known technology in pharmaceutical preparation field. Moreover, the composites in the form of solution may be prepared in saline with benzyl alcohol or other suitable corrosion remover, absorption enhancer for reinforcing bioavailability, fluorocarbon compound and/or other conventional solubilizer or dispersing agent.

The pharmaceutical acceptable carriers that can be used for those composites include ion exchanger, aluminum oxide, aluminum stearate, lecithin; serum protein such as human serum albumin; buffer substance such as phosphate; glycine, sorbic acid, potassium sorbate, partial glyceride mixture of saturate plant fatty acid, water, salt or electrolyte such as sulfuric acid protamine, sodium hydrogen phosphate, potassium hydrogen phosphate, sodium chloride, zinc salt; colloidal silicon dioxide, magnesium trisilicate, polyvinylpyrrolidone, cellulose substance, polyethylene glycol, sodium carboxymethylcellulose, polyacrylate, wax, polyethylene-polypropylene oxide-block polymer, polyethylene glycol and wool fat.

Examples of suitable excipients include but not limited to water, saline, lactose, glucose, cane sugar, sorbitol, Mannitol, starch, Arabic gum, calcium phosphate, alginate, tragacanth, gelatin, calcium silicate, microcrystalline cellulose, polyvinylpyrrolidone, cellulose, syrup, methylcellulose, ethyl cellulose, hydroxypropyl methyl cellulose and polyacrylic acid, such as carbopol. The composites may include lubricant such as talcum powder, magnesium stearate and mineral oil; wetting agent; emulsifier; suspending agent; corrosion remover such as methyl-, ethyl- and propyl-hydroxyl-benzoate; pH modifier such as inorganic and organic acid and alkali; sweetening agent; and corrigent.

In addition to above representative dosage forms, the technical personnel in the field usually know other pharmaceutical acceptable excipients, carriers and dosage forms, which are included in the present invention. It is understood that the specific dosage and therapeutical schedule for any specific patient are decided by many factors. They include the activity of specific compound used, patient's age, weight, general health condition, sex, diet, drug administration time, discharge rate, combination, judgment of therapist and severity of specific disease treated. The quantity of active ingredient is also decided by specific compound and other therapeutic drug in (if any) composites.

The above pharmaceutical composites can further include other active ingredients for treating or auxiliary treating proliferating diseases, or the other combined use of the drugs for treating or auxiliary treating proliferating disease, such as the combined use of anti-proliferative agent, immunomodulator, anticancer drug, cytotoxic agent, and anticancer aided drug beyond the present invention.

Other examples of those therapeutic agents include: anti-proliferative agent, such as methotrexate; FK506 (fujimycin, Prograf), mycophenolate mofetil; TNF-α inhibitor, such as Tenidap; cytotoxic drug, such as azathioprine and cyclophosphamide; anti-TNF antibody or soluble TNF receptor, such as etanercept (Enbrel); Rapamycin, leflunimide, and cyclo-oxygenase-2 (COX-2) inhibitor, such as celecoxib and rofecoxib, or their derivatives; and the PTK inhibitor that the existing technology has been made public.

Typical anticancer drugs and cytotoxic agents include but not limited to: alkylating agent, such as chlormethine, alkyl-sulphonate, nitrourea, aziridine and triazene; antimetabolite, such as Folate antagonist, purineanalogue and pyrimidine analogue; antibiotics, such as anthracene nucleus, bleomycin, mitomycin, dactinomycin and streptomyces plicatus; enzyme, such as L-asparaginase; farnesyltransferase inhibitor; hormone drug, such as, glucocorticoid, estrogen/antiestrogen, androgen/antiandrogen, pregnendione, luteinizing hormone releasing hormone antagonist, acetic acid Sandostatin; microtubules breaker, such as ecteinascidin or its analogue and derivant; microtubules stabilizer, such as paclitaxel, docetaxel and epothilone or their analogues or derivatives; products derived from plants, such as Vinca Alkaloids, epipodophyllotoxin, taxane; topoisomerase inhibitor; isoprene based protein transferase inhibitor; miscellaneous reagents, such as, hydroxycarbamide, Procarbazine, Mitotane, hexamethyl melamine, platinum coordinated complex such as cisplatin and Carboplatin; and other drugs used for anticancer and cytotoxic agent, such as biological response regulator, growth factor; and immunomodulator and monoclonal antibody. The compound of the present invention may also be used in combination with radiotherapy.

The examples of the anticancer drugs and cytotoxic agents in the same category include but not limited to: chlormethine hydrochloride, cyclophosphamide, chlorambucil, betamerphalan, ifosfamide, busulfan, carmustine, lomustine, semustine, streptozotocin, thiotepa, dacarbazine, methotrexate, sulfur guanopterin, thiol petrin, fludarabine, Pentastatin, leustatin, cytarabine, fluorouracil, doxorubicin hydrochloride, daunorubicin, idarubicin, sulfuric acid bleomycin, mitomycin C, Dactinomycin D, safracins, Micronomicin, quinocarcins, discodermolides, vincristine, vincaleukoblastinum, Corvino libin tartrate, etoposide, teniposide, paclitaxel, tamoxifen, estramustine, phosphoric acid estramustine sodium salt, Flutan, Buserelin, Lupron, pteridine, diyne, levomisole, aflacon, interferon, interleukin, Aldesleukin, Felsdine, myeloid growth factor, rituximab, BCG, vitamin A acid, irinotecan hydrochloride, betamethasone, gemcitabine-hydrochloride, hexamethy and Topotecan, and any of their analogues or derivatives.

The preferred members in those categories include but not limited to: paclitaxel, cisplatin, Carboplatin, adriamycin, idarubicin, daunorubicin, aminopterin, methotrexate, methyl petrin, mitomycin C, ecteinascidin, pholipomycin, 5-fluorouracil, 6-thiol petrin, gemcitabine, cytarabine, podophyllotoxin or podophyllotoxin derivant, such as etoposide, phosphoric acidetoposide or teniposide, betamerphalan, vincaleukoblastinum, vincristine, leurosidine, vindesine and leurosine.

Examples of antitumor drugs and other cytotoxic agents include: U.S. patent application Ser. No. 09/506, 481, submitted on Feb. 17, 2000, German patents 41380428, WO97/19086, WO98/22461, WO98/25929, WO98/38192, WO99/01124, WO99/02224, WO99/02514, WO99/03848, WO99/07692, WO99/27890, WO99/28324, WO99/43653, WO99/54330, WO99/54318, WO99/54319, WO99/65913, WO99/67252, WO99/67253, and epothilone derivatives in WO00/00485; cell cycle protein dependent kinase inhibitor in WO99/24416; and isoprene protein transferase inhibitor in WO97/30992 and WO98/54966.

Other therapeutic agents above may use, for example, the dosage pointed out in clinical medicine manual or the dosage determined by the general technical personnel in the field when using together with the compound of the present invention.

Finally, the present invention provides a method for treating cell proliferation diseases, including effective dosage of the compound in formula A delivering to the patient with requirement.

"Cell proliferation disease" refers to the disease with the characteristic of abnormal cell proliferation. Proliferation disease does not mean any limit on cell growth rate but only represents the loss of the normal control affecting growth and cell division. Therefore, in some embodiments, the cell of proliferation disease may have the same cell division rate as normal cell without affecting the signal restricting such growth. Within the range of neoplasm or tumor, the neoplasm or tumor of "cell proliferation disease" is the abnormal growth of tissue. "Cell proliferation disease" refers to any kind of various malignant tumors characterized in cell proliferation. Such tumors have the capability to intrude into surrounding tissues and/or transfer to new position of settlement.

In general, the cell proliferation diseases that can be treated with the compound exposed in paper relate to any disease characterized in abnormal cell proliferation. Those include various benign or malignant, transferred or non-transferred tumor and cancer. The method described in this paper may be used for confronting the particular characteristics of tumor, such as tissue invasion or transitivity. Cell proliferation diseases include various tumors. They include but not limited to:

Cancer: Including bladder cancer, breast cancer, colon cancer, renal cancer, liver cancer, lung cancer, cellule lung cancer, ovarian cancer, prostate cancer, pancreatic cancer, esophageal cancer, gastric cancer, gallbladder, cervical cancer, thyroid cancer and skin cancer, squamous cell carcinoma;

Hematopoietic tumors of lymphatic system: Including leukemia, leukemia of acute lymphatic system, leukemia of acute lymphoblast, β-cell lymphoma, T-cell lymphoma, Hodgkins lymphoma, non-Hodgkins lymphoma, chorionic villus lymphoma and Burketts lymphoma;

Hematopoietic tumors of myeloid lineage: Including acute and chronic myelocytic leukemia, myelodysplastic syndromes and promyelocytic leukemia;

Tumors of central and peripheral nervous system: Including astrocytoma, neuroturbo chargeoma, glioma and schwannoma;

Neoplasms of mesenchymal origin: Including fibrosarcoma, rhabdomyosarcoma and osteosarcoma;

Other tumors: Including melanoma, xenoderma pigmentosum, amination acanthoma, seminoma, follicular thyroid carcinoma and teratocarcinoma.

In some embodiments, the malignant proliferation disease treated is hematologic neoplasm. This tumor is the cell hyperplasia of hemopoietic system.

In some embodiments, the hematologic neoplasm treated is lymphocytoma, wherein abnormal cell originates from lymphoid cell lineage cells and/or the characteristic phenotype displays lymphoid cell lineage cells. Lymphoid cell tumor may be subdivided into B cytoma, T and NK cytoma, and Hodgkin lymphoma. B cytoma can be further divided into ancestor B cytoma and mature/peripheral B cytoma. The illustrational B cytomais precursor B lymphocyte leukemia/lymphoma (precursor B cell acute lymphocyte leukemia), while the illustrational mature/peripheral B cytoma is B cell chronic lymphocyte leukemia/small lymphocyte lymphoma, B cell prolymphocyte leukemia, lymphoplasmacytic lymphoma, splenic marginal region B cell lymphoma, hairy cell leukemia, plasma cell myeloma/plasmacytoma, MALT type universal domain area B cell lymphoma, section area B cell lymphoma, follicle lymphoma, jacket cell lymphoma, diffuse large B cell lymphoma, mediastinal large B cell lymphoma, primary effusion lymphoma and Burkittl ymphoma/Burkitt cell leukemia. T cell and NK cytoma can be further divided into precursor T cell cancer and mature (peripheral) T cytoma. Illustrational precursor T cytoma is precursor T-lymphocyte lymphoma/leukemia (precursor T cell acute lymphocyte leukemia), while illustrational mature (peripheral) T cytoma is T cellprolymphocyte leukemia T cell particle lymphocyte leukemia, aggressive NK cell leukemia, adult T cell lymphoma/leukemia (HTLV-1), extranodal nasal type NK/T cell lymphoma; nasal form, pathotype T cell lymphoma, hepatolienal γ-δ T cell lymphoma, subcutaneous panniculitis T cell lymphoma, granuloma fungoides/Sezary syndrome, retrogressive maxicell lymphoma; T/invalid cell, primary skin type peripheral T cell lymphoma, non-additionally characterized blood vessel immunoblastic lymphadenopathy T cell lymphoma, retrogressive maxicell lymphoma, T/invalid cell, primary body type. The third type of lymphoid cell tumor is Hodgkin lymphoma, also called as Hodgkin's disease. The illustrative diagnosis of the disease treated with the said compound includes but not limited to nodular lymphocyte predominant Hodgkin lymphoma and various Hodgkin's diseases in classic form, wherein the illustrational diseases are nodual hardening Hodgkin lymphoma (Level 1 and Level 2), lymphocyte-enriched classic Hodgkin lymphoma, Hodgkin lymphoma composed of mixed cells and lymphocytic depletion Hodgkin lymphoma.

In some embodiments, the hematologic neoplasm treated is myelocytome. Such tumor includes a major category of malignant proliferation disease involving or displaying the cell characteristic phenotype of myelocyte spectrum. Myelocytome may be subdivided into myeloproliferative disease, myeloproliferative disorder/myelodysplastic disease, myelodysplastic syndrome and acute myeloid leukemia. Illustrational myelodysplastic disease is chronic myelogenous leukemia, chronic neutrophils leukemia, chronic eosinophilic pneumonia leukemia/hypereosinophilic syndrome, chronic idiopathic myelofibrosis, polycythemia and primary thrombocythemia. Illustrational myeloproliferative disorder/myelodysplastic disease is chronic myelomonocytic leukemia, atypical chronic myelogenous leukemia and teenager acute myelomonocytic leukemia. Illustrational myelodysplastic syndrome is the refractory anemia with and without annular sideroblast, refractory pancytopenia (myelodysplastic syndrome) with multilinkage dysplasia, refractory anemia (myelodysplastic syndrome) with excessive germ cell, 5q-syndrome and myelodysplastic syndrome. In various embodiments, the compound of the present invention can be used for treating any relevant myelocytome.

In some embodiments, the said compound can be used for treating acute myeloid leukemia (AML). Such leukemia represents a major category of myelocytome in which the diseases may be further divided. Such branches include but not limited to AML with recurrent chromosomal translocation, AML with multilinkage dysplasia and other unclassified AMLs. The illustrational AMLs with recurrent chromosomal translocation include but not limited to AML with t (8;21) (q22;q22), AML1 (CBF-α)/ETO, acute promyelocytic leukemia (AML with t(15;17X)(q22;q11-12) and variants, PML/RAR-α), AML with abnormal eosinophil cell (inv(16) (p13q22) or t(16;16)(p13;q11), CBFb/MYH11X) and 11q23 (MLL) abnormal AML. The illustrational AMLs with multilinkage dysplasia are the AMLs relative to or irrelative to the foregoing myelodysplastic syndrome. Other acute myeloid leukemia not classified into the category of any definition includes minimally differentiated AML, immature AML, mature AML, acute myelomonocytic leukemia, acute mononuclear leukemia, acute red cell leukemia, acute megakaryocyte leukemia, acute basophil cell leukemia and acute total leukemia with myelofibrosis.

Preferably, the treated tumors are breast cancer, lung cancer, colon cancer, gastric cancer, esophagus cancer, ovarian cancer, osteosarcoma, cervical cancer, liver cancer, cerebroma, prostate cancer, and melanoma.

The term "treatment" used in the present invention indicates the relief of the symptom relating to symptom or disease or termination of the further development or deterioration of those symptoms, or stopping or preventing disease or symptom.

The term "pharmaceutical effective dose", "effective dose of treatment" or "therapeutically effective dose" refers to the quantity of the subject compound that research personnel, veterinarians, physicians or other clinical technicians are seeking the biological or medical reaction to tissue, system, animal or human.

The term "effective dose of treatment" includes the dose of compound delivered sufficient to stop the development of one or more symptoms of diseases or symptoms under treatment or to relieve to a certain degree. The effective dose of treatment should be changed with the compound, symptom or status and severity as well as the age, weight, etc. of the mammal treated.

The term "patient" defined in this paper includes animals, such as mammal. Mammal includes but not limited to primate (such as human), cow, sheep, goat, horse, dog, cat, rabbit, rat, mice, etc. In preferred embodiment, the patient is human. The effective dose of the compound of the present invention may be decided by the general technical personnel in the field. For adult, the dosage is approximately 0.001-1000 mg of active compound per kg of weight per day. The drug may be administered in single dose or in respective divided dose, such as 1-4 times per day. It should be clear that, for any specific object, the specific dose level and administration frequency are variable and decided by many factors, including the activity of the specific compound used, metabolic stability and acting duration of the compound, species of administration object, age, weight, health status, sex, and dietary habit, way and time of administration, discharging rate, combination of drugs, and the severity of specific symptom.

Comparing with the antitumor platinum compound of the prior art, the solubility of the ionized compound of the present invention is obviously improved. The solubility of the compounds in the invention is above 80 mg/ml in water. Especially for the compounds in embodiments of the present invention, the solubility is generally more than 100 mg/ml. Moreover, the platinum compound of the prior art cannot be salinized. The compound of the present invention can produce salt form and is more favorable for producing into the form of stable preparation.

The above dosage forms of any compound containing effective dose are within the range of the conventional test and the present invention. Therapeutically effective dose may be adjusted according to the administration route and dosage form. The representative compound of the present invention is the preparation showing high therapeutic index. Therapeutic index is the dose ratio between toxicity and curative effect and can be expressed by the ratio between $LD_{50}$ and in vivo antitumor activity ($ED_{50}$) or in vitro cytotoxicity ($IC_{50}$). $LD_{50}$ is the lethal dose for 50% population; $ED_{50}$ is the therapeutically effective dose for 50% population. $LD_{50}$ and $ED_{50}$ are determined in animal cell culture medium or experimental animal through standard pharmaceutical method. Since $LD_{50}$ (lethal dose for 50% animal, mmol/kg) representing toxicity of the compound of the present invention is much higher than the platinum compound cisplatin and carboplatin, etc. of the existing technology and the effective dose of in vivo antitumor activity and in vitro concentration of inhibiting cell toxicity $IC_{50}$ value are equivalent or lower than carboplatin, it can be used for treating the patient who cannot tolerate the existing platinum compounds such as carboplatin, cisplatin, etc. and achieve better technical effect. The $IC_{50}$ value of the compound of the present invention is higher than 0.45 mmol/kg, preferably higher than 0.5 mmol/kg, and most preferably higher than 0.6 mmol/kg. The compound of the present invention may be individually use or used in combination, and/or in combined use with other suitable therapeutic agents used for treating proliferating diseases.

Embodiment

The following embodiments and test examples were described in the present invention in details, but will not restrict the enablement of the present invention in any way. The technical personnel in this field should understand that any modification or substitution of appropriate technical characteristics according to the instructions of the existing technology remain within the range of protection claimed by the present invention. The purity of the raw materials used in the present invention is just above chemical purity. The said raw materials may be purchased from market. The compounds obtained in the following embodiments are in the form of salt. Ionized compounds may be obtained by adding alkali to regulate pH value of those compounds in the form of salt. The said compounds can be easily converted into other types of organic or inorganic salts by using the method of adding appropriate acid, which possibly include but not limited to nitrate, carbonate, bicarbonate, phosphate, hydrophosphate, dihydric phosphate, sulphate, bisulfate, phosphite, acetate, propionate, isobutyrate, malonate, benzoate, succinate, suberate, fumarate, mandelate, phthalate, benzene sulfonate, tosilate, citrate, tartrate, mesylate, arginine salt, glucuronate or galactose acid salt, etc. This will not be explained again in the following embodiments one by one.

EXAMPLE 1

[2-(2-methylamine ethyl)-malonato].[cis-diamino]platinum (II) phosphate

Step 1: 2-(2-bromethyl)-diethyl malonate

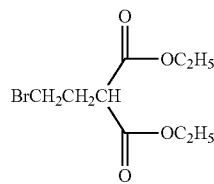

Diethyl malonate (16.02 g, 0.1 mol) and 1, 2-dibromoethane (47.45 g, 0.25 mol) were placed into 150 ml flasks. $K_2CO_3$ (15.203 g, 0.11 mol) and tetrabutylammonium bromide (153 mg) were added. The mixture was stirred and heated to 65~85° C. in oil bath for 16~24 h; suction filtration was conducted to remove solid which was washed with diethyl ether (30 ml×3 times), filtrate was consolidated; and washed with water (40 ml×3 times) then dried with $MgSO_4$ for 4~8 h; After removal of solvent, the distillate was collected for 125° C.-143° C. at vacuum 7 mmHg; the product was 8.699 g; and the yield was 32.7%.

Step 2: 2-(2-methylamine ethyl)-diethyl malonate

To the mixture of

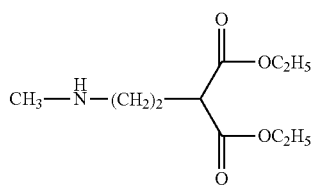

2-bromethyl-diethyl malonate (106.91 g, 0.4 mol), anhydrous $K_2CO_3$ (55.840 g, 0.4 mol) in acetonitrile (500 ml), methylamine (31.1 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous $MgSO_4$ overnight; after removal of solvent in vacuo, light yellow oil (85.5 g) was obtained; the oil was purified by column chromatography to afford the title compound (41.4 g) and the yield was 47.7%.

Step 3: 2-(2-methylamine ethyl)-sodium malonate

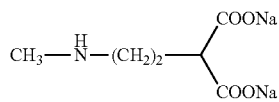

2M NaOH solution (2.5 mL) was added to 2-(2-methylamine ethyl)-diethyl malonate (435 mg, 2 mmol) in 20 mL flasks; and the mixture was stirred at room temperature for 45~60 h, 2-(2-methylamine ethyl)-malonic acid disodium salt solution was obtained.

Step 4: Diamine.diiodo-platinum (II)

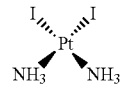

KI (6.640 g, 40 mmol) solution (50 ml) was added to potassium chloroplatinite ($K_2PtCl_4$) (2.075 g, 5 mmol) in water (50 ml), the mixture was stirred and heated to 40~60° C. away from light and oxygen for 0.5~2 h, and then ammonia water (50 ml) (containing 5 mmol ammonia) was added; the reaction mixture was kept under this condition for 0.5~2 h. Light yellow solid product (2.29 g) was obtained by suction filtration and washed successively with water (10 ml×3 times) and diethyl ether (10 ml×3 times); the yield was 95.1%. Elemental analysis: H1.24% (theoretical 1.21%); N5.56% (theoretical 5.797%).

Step 5: Diamine.dihydrate platinum (II) sulphate

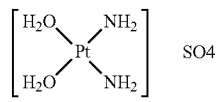

Adding $Ag_2SO_4$ (625 mg, 2 mmol) in water (30 ml) and stirring, diamine.diiodo-platinum (II) (0.96 g, 2 mmol) was added and another part of water (40 ml) was added to the reaction mixture; the mixture was stirred and heated at 40~60° C. for 4~8 h. After removing AgI deposit by suction, the filtrate was the aqueous solution of the product.

Step 6: [2-(2-methylamine ethyl)-malonato].[cis-diamine]platinum (II) phosphate

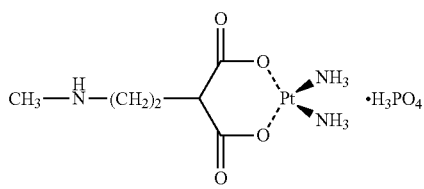

2-(2-methylamine ethyl)-malonic acid disodium salt (2 mmol) solution was regulated the pH to 5~7 with H₃PO₄ (1M) and then cis-diamine.dihydrate platinum (II) sulphate aqueous solution was poured into reaction mixture; the mixture was heated in water bath to 40~75° C. for 4-6 h. under N₂ protection; after filtration, reaction mixture was concentrated to a certain volume and should be at a standstil; crystalline-type [2-(2-methylamine ethyl)-malonato].[cis-diamino] platinum (II) phosphate (106 mg) is obtained.

The said compound is soluble in water. The solubility is 221 mg/ml. Free base of the compound [2-(2-methylamine ethyl)-malonic].[cis-diamine] platinum (II) could be obtained by regulating pH with alkali. Free base elemental analysis: C18.29% (theoretical 18.56%); H3.84% (theoretical 3.87%); N10.57% (theoretical 10.82%).

¹HNMR (D₂O) (ppm): δ3.60 (t, 1H), δ2.87 (s, 3H), δ2.65 (t, 2H), δ1.75 (m, 2H).

EXAMPLE 2

[2-(2-dimethylamine ethyl)-malonato].[cis-diamine] platinum (II) acetate

Step 1: Same as [Embodiment 1] Step 1

Step 2: 2-(2-dimethylamine ethyl)-diethyl malonate

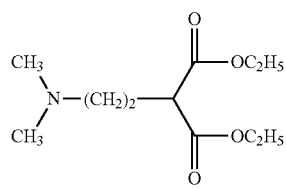

To the mixture of 2-broethyl-diethyl malonate (106.91 g, 0.4 mol), anhydrous K₂CO₃ (55.840 g, 0.4 mol) in acetonitrile (500 ml), dimethylamine (45.3 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (91.3 g) was obtained; the oil was purified by column chromatography to afford the title compound (45.37 g) and the yield was 49.1%.

Step 3: 2-(2-dimethylamine ethyl)-sodium malonate

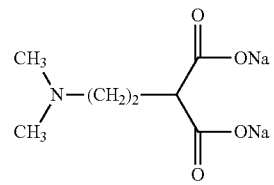

2M NaOH solution (2.5 mL) was added to 2-(2-dimethylamine ethyl)-diethyl malonate (435 mg, 2 mmol) in 20 mL flasks; and the mixture was stirred at room temperature for 45~60 h, 2-(2-dimethylamine ethyl)-malonic acid disodium salt solution was obtained.

Step 4, 5: Same as [Embodiment 1] Step 4, 5

Step 6: [2-(2-dimethylamine ethyl)-malonato].[cis-diamine] platinum (II) acetate

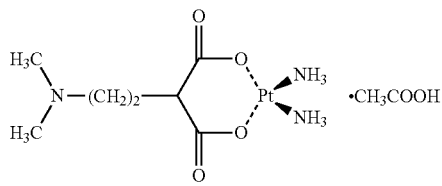

2-(2-dimethylamine ethyl)-malonic acid disodium salt (2 mmol) solution was regulated to the pH 5~7 with CH₃COOH (1M) and then cis-diamine.dihydrate platinum (II) sulphate aqueous solution was poured into reaction mixture; the mixture was heated in water bath to 40-6 h. under N₂ protection; after filtration through celite, reaction mixture was concentrated to a certain volume and should be at a standstill; crystalline-type 2-(2-dimethylamine ethyl)-malonic-cis-diamino platinum (II) phosphate (113 mg) was obtained.

Both the free base and salt of the said compound are soluble in water. The solubility is 198 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C20.57% (theoretical 20.9%); H4.41% (theoretical 4.23%); N10.52% (theoretical 10.45%).

¹HNMR (D₂O)(ppm): δ3.65(t,1H), δ2.66(s,6H), δ2.55(t, 2H), δ1.74(m,2H).

EXAMPLE 3

[2-(3-dimethylamine propyl)-malonato].[cis-diamine] platinum (II) phosphate

Step 1: 2-(3-bromopropane)-diethyl malonate

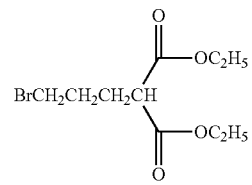

Diethyl malonate (16.02 g, 0.1 mol) and 1,3-dibromoethane (50.6 g, 0.25 mol) were placed into 150 ml flasks. K$_2$CO$_3$ (15.13 g, 0.11 mol) and tetrabutylammonium bromide (153 mg) were added. The mixture was stirred and heated to 65~85° C. in oil bath for 16~24 h; suction filtration was conducted to remove solid which was washed with diethyl ether (30 ml×3 times), filtrate consolidated was washed with water (40 ml×3 times) and dried over anhydrous MgSO$_4$ for 4~8 h. After removal of solvent, the distillate was collected for 125-143° C. at vacuum 7 mmHg; the product was 9.39 g; and the yield was 32.9%

Step 2: 2-(3-dimethylamine propyl)-diethyl malonate

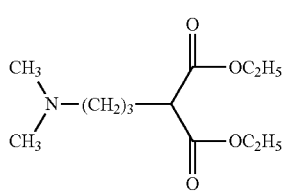

To the mixture of 2-bropropyl-diethyl malonate (106.91 g, 0.4 mol), anhydrous K$_2$CO$_3$ (55.70 g, 0.4 mol) in acetonitrile (500 ml), dimethylamine (45.2 g, 1.0 mol) solution in refrigerated was added and the mixture was heated at 40~60° C. for 2-6 h; insoluble substance was filtered out and the filtrate was concentrated in vacuo; the residue was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (97.1 g) was obtained; the oil was purified by column chromatography to afford the title compound (34.37 g) and the yield was 35.1%.

Step 3: 2-(3-dimethylamine propyl)-sodium malonate

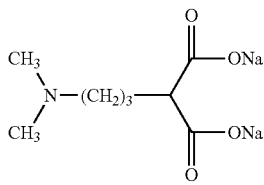

2M NaOH solution (2.5 mL) was added to 2-(2-dimethylamine ethyl)-diethyl malonate (463 mg, 2 mmol) in 20 mL flasks; and the mixture was stirred at room temperature for 45~60 h, 2-(3-dimethylamine propyl)-malonic acid disodium salt solution is obtained.

Step 4, 5: Same as [Embodiment 1] Step 4, 5

Step 6: [2-(3-dimethylamine propyl)-malonato].[cis-diamine] platinum (II) phosphate

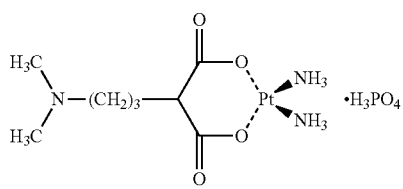

2-(3-dimethylamine propyl)-malonic acid disodium salt (2 mmol) solution was regulated to the pH 5~7 with H$_3$PO$_4$ (1M) and then cis-diamine.dihydrate platinum (II) sulphate aqueous solution was poured into reaction mixture; the mixture was heated in water bath to 40~75° C. for 4-6 h. Under N$_2$ protection; after filtration, the filtrate was concentrated to a certain volume and should be at a standstill; crystalline-type 2-(2-methylamine ethyl)-malonic-cis-diamino platinum (II) phosphate (115 mg) was obtained.

Both the free base and salt of the said compound are soluble in water. The solubility is 164 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C23.22% (theoretical 23.08%); H4.54% (theoretical 4.57%); N10.32% (theoretical 10.10%).

$^1$HNMR(D$_2$O)(ppm):δ3.62(t,1H), δ2.75(s,6H),δ2.69(t,2H),δ1.75(m,2H), δ1.49(m,2H).

EXAMPLE 4

[2-(3-amino propyl)-malonato].[cis-diamine] platinum (II) phosphate

Step 1: Same as [Embodiment 3] Step 1

Step 2: 2-(3-amino propyl diethyl malonate

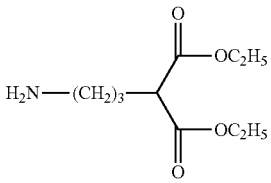

To the mixture of 2-bropropyl-diethyl malonate (113.7 g, 0.4 mol), anhydrous K$_2$CO$_3$ (55.40 g, 0.4 mol) in acetonitrile (500 ml), dimethylamine (45.2 g, 1.0 mol), Excessive ammonia was bubbled into mixture which was then heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (85.9 g) was obtained; the oil was purified by column chromatography to afford the title compound (34.9 g) and the yield was 40.2%.

Step 3: 2-(3-amino propyl)-sodium malonate

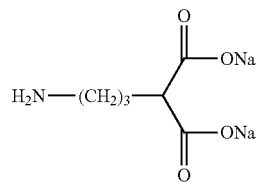

2M NaOH solution (2.5 mL) was added to 2-(3-aminopropyl)-diethyl malonate (433 mg, 2 mmol) in 20 mL flasks; and the mixture was stirred at room temperature for 45~60 h, 2-(3-aminopropyl)-malonic acid disodium salt solution was obtained.

Step 4, 5: Same as [Embodiment 1] Step 4, 5

Step 6: [2-(3-amino propyl)-malonato].[cis-diamine] platinum (II) phosphate

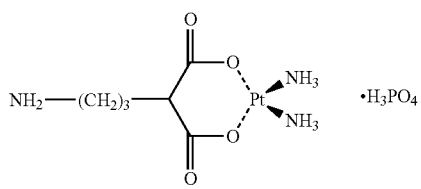

2-(3-aminopropyl)-malonic acid disodium salt (2 mmol) solution was regulated to the pH 5~7 with $H_3PO_4$ (1M) and then cis-diamine.dihydrate platinum (II) sulphate aqueous solution was added into reaction mixture which was then heated in water bath to 40~75° C. for 4-6 hr. under $N_2$ protection; after filtration, the filtrate was concentrated to a certain volume and should be at a standstill; crystalline-type 2-(3-aminpropyl)-malonic-cis-diamino platinum (II) phosphate (118 mg) was obtained.

Both the free base and salt of the said compound are soluble in water. The solubility is 176 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C18.37% (theoretical 18.56%); H3.61% (theoretical 3.87%); N10.72% (theoretical 10.82%).

1HNMR(D2O)(ppm):δ3.62(t,1H), δ2.88(t,2H), δ1.78(m, 2H), δ1.52(m,2H).

EXAMPLE 5

[2-(2-diethylamine ethyl)-malonato].[cis-diamine] platinum (II) phosphate

Step 1: Same as [Embodiment 1] Step 1

Step 2: 2-(2-diethylamine ethyl)-diethyl malonate

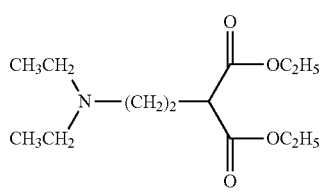

To the mixture of 2-broethyl-diethyl malonate (106.75 g, 0.4 mol), anhydrous $K_2CO_3$ (55.70 g, 0.4 mol) in acetonitrile (500 ml), dimethylamine (45.2 g, 1.0 mol) solution in refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (92.5 g) was obtained; the oil was purified by column chromatography to afford the title compound (46.93 g) and the yield was 45.3%.

Step 3: 2-(2-diethylamine ethyl)-sodium malonate

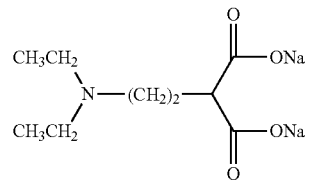

2M NaOH solution (2.5 mL) was added to 2-(2-diethylamine ethyl)-diethyl malonate (518 mg, 2 mmol) in 20 mL flasks; and the mixture was stirred at room temperature for 45~60 h, 2-(2-diethylamine ethyl)-malonic acid disodium salt solution was obtained.

Step 4, 5: Same as [Embodiment 1] Step 4, 5

Step 6: [2-(2-diethylamine ethyl)-malonato].[cis-diamine] platinum (II) phosphate

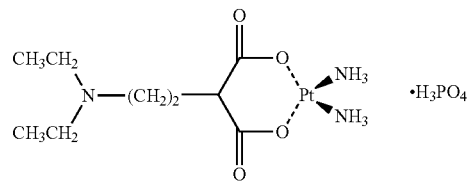

2-(2-diethylamine ethyl)-malonic acid disodium salt (2 mmol) solution was regulated to the pH 5~7 with $H_3PO_4$ (1M) and then cis-diamine.dihydrate platinum (II) sulphate aqueous solution was poured into reaction mixture; the mixture was heated in water bath to 40~75° C. for 4-6 h. Under $N_2$ protection; after filtration, reaction mixture was concentrated to a certain volume and should be at a standstill; crystalline-type 2-(2-diethylamine ethyl)-malonic-cis-diamino platinum (II) phosphate (118 mg) was obtained.

Both the free base and salt of the said compound are soluble in water. The solubility is 187 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C24.9% (theoretical 25.12%); H4.84% (theoretical 4.88%); N9.56% (theoretical 9.77%).

$^1$HNMR($D_2O$)(ppm):δ3.60(t,1H),δ2.78(q,4H), δ2.70(t, 2H), δ1.70(m,2H),δ1.08(t,6H).

EXAMPLE 6

[2-(3-diethylamine propyl)-malonato].[cis-diamine] platinum (II)

Step 1: Same as [Embodiment 3] Step 1

Step 2: 2-(3-diethylamine propyl)-diethyl malonate

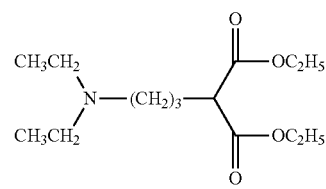

To the mixture of 2-bropropyl-diethyl malonate (114.1 g, 0.4 mol), anhydrous $K_2CO_3$ (55.60 g, 0.4 mol) in acetonitrile (500 ml), diethylamine (73.1 g, 1.0 mol) solution refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (105.3 g) was obtained; the oil was purified by column chromatography to afford the title compound (39.5 g) and the yield was 36.3%.

Step 3: 2-(3-diethylamine propyl)-sodium malonate

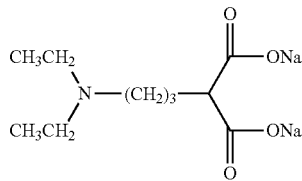

2M NaOH solution (2.5 mL) was added to 2-(3diethylamine ethyl)-diethyl malonate (518 mg, 2 mmol) in 20 mL flasks; and the mixture was stirred at room temperature for 45~60 h, 2-(2-diethylamine ethyl)-malonic acid disodium salt solution was obtained.

Step 4, 5: Same as [Embodiment 1] Step 4, 5

Step 6: 2-(3-diethylamine propyl)-malonic-cis-diamino platinum (II) phosphate 2-(3-diethylamine ethyl)-malonic acid disodium salt (2 mmol) solution was regulated to the pH 5~7 with $H_3PO_4$ (1M) and then cis-diamine.dihydrate platinum (II) sulphate aqueous solution was poured into reaction mixture; the mixture was heated in water bath to 40~75° C. for 4-6 h. under $N_2$ protection; after filtration through celite, reaction mixture was concentrated to a certain volume and should be at a standstill; crystalline-type 2-(3-diethylamine ethyl)-malonic.cis-diamino platinum (II) phosphate (123 mg) was obtained.

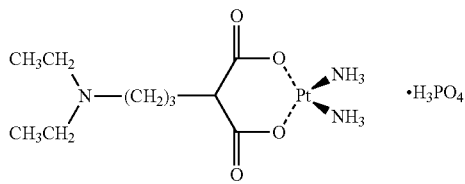

$^1HNMR(D_2O)(ppm)$: δ3.62(t,1H), δ2.76(q,4H), δ2.69(t,2H), δ1.74(m,2H), δ1.49(m,2H), δ1.07(t,6H).

Both the free base and salt of the said compound are soluble in water. The solubility is 165 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C26.76% (theoretical 27.03%); H4.85% (theoretical 5.18%); N9.64% (theoretical 9.46%).

EXAMPLE 7

2-(3-di-n-propylamine ethyl)-malonic.cis-diamino platinum (II) phosphate

Step 1: Same as [Embodiment 1] Step 1

Step 2: 2-(2-di-n-propylamine ethyl)-diethyl malonate

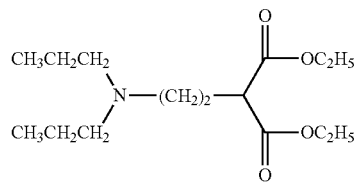

To the mixture of 2-broethyl-diethyl malonate (106.6 g, 0.4 mol), anhydrous $K_2CO_3$ (55.0 g, 0.4 mol) in acetonitrile (500 ml), di-n-propylamine (101.0 g, 1.0 mol) solution refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (109.3 g) was obtained; the oil was purified by column chromatography to afford the title compound (47.53 g) and the yield was 41.4%.

Step 3: 2-(2-di-n-propylamine ethyl)-sodium malonate

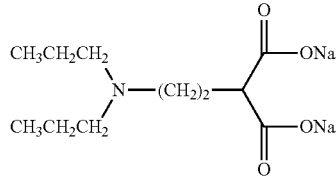

2M NaOH solution (2.5 mL) was added to 2-(2-di-n-propylamine ethyl)-diethyl malonate (575 mg, 2 mmol) in 20 mL flasks; and the mixture was stirred at room temperature for 45~60 h, 2-(2-di-n-propylamine ethyl)-malonic acid disodium salt solution was obtained.

Step 4, 5: Same as [Embodiment 1] Step 4, 5

Step 6: 2-(2-di-n-propylamine ethyl)-malonic-cis-diamino platinum (II) phosphate 2-(2-di-n-propylamine ethyl)-malonic acid disodium salt (2 mmol) solution was regulated to the pH 5~7 with $H_3PO_4$ (1M) and then cis-diamine.dihydrate platinum (II) sulphate aqueous solution was poured into reaction mixture; the mixture was heated in water bath to 40~75° C. for 4-6 h. under $N_2$ protection; after filtration through celite, reaction mixture was concentrated to a certain volume and should be at a standstill; crystalline-type 2-(2-di-n-propylamine ethyl)-ma- Ionic-cis-diamino platinum (II) phosphate (123 mg) was obtained.

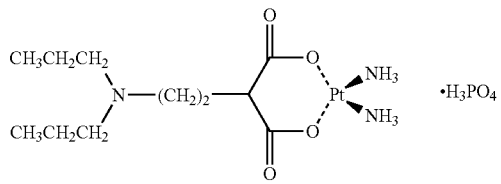

$^1$HNMR (D$_2$O) (ppm): δ3.60(t,1H), δ2.77(t,4H), δ2.70(t, 2H), δ1.78(m,2H), δ1.25(m,4H), δ1.05(t,6H).

Both the free base and salt of the said compound are soluble in water. The solubility is 159 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C28.59% (theoretical 28.82%); H5.62% (theoretical 5.46%); N9.29% (theoretical 9.17%).

EXAMPLE 8

2-(3-di-n-propylamine propyl)-malonic-cis-diamino platinum (II) mesylate

Step 1: Same as [Embodiment 3] Step 1

Step 2: 2-(3-di-n-propylamine propyl)-diethyl malonate

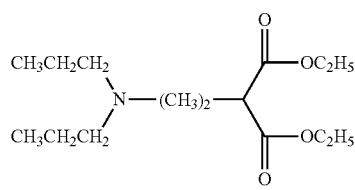

To the mixture of 2-bropropyl-diethyl malonate (113.0 g, 0.4 mol), anhydrous K$_2$CO$_3$ (55.20 g, 0.4 mol) in acetonitrile (500 ml), di-n-propylamine (45.2 g, 1.0 mol) solution refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (103.1 g) was obtained; the oil was purified by column chromatography to afford the title compound (40.1 g) and the yield was 33.3%.

Step 3: 2-(3-di-n-propylamine propyl)-sodium malonate

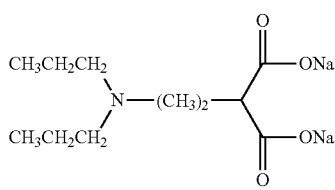

2M NaOH solution (2.5 mL) was added to 2-(3-di-n-propylamine propyl)-diethyl malonate (603 mg, 2 mmol) in 20 mL flasks; and the mixture was stirred at room temperature for 45~60 h, 2-(3-di-n-propylamine propyl)-malonic acid disodium salt solution was obtained.

Step 4, 5: Same as [Embodiment 1] Step 4, 5

Step 6: [2-(3-di-n-propylamine propyl)-malonato].[cis-diamine] platinum (II) mesylate 2-(3-di-n-propylamine propyl)-malonic acid disodium salt (2 mmol) solution was regulated to the pH 5~7 with CH$_3$SO$_3$H (1M) and then cis-diamine.dihydrate platinum (II) sulphate aqueous solution was poured into reaction mixture; the mixture was heated in water bath to 40~75° C. for 4-6 h. under N$_2$ protection; after filtration through celite, reaction mixture was concentrated to a certain volume and should be at a standstill; crystalline-type 2-(3-di-n-propylamine propyl)-malonic-cis-diamino platinum (II) phosphate (125 mg) is obtained.

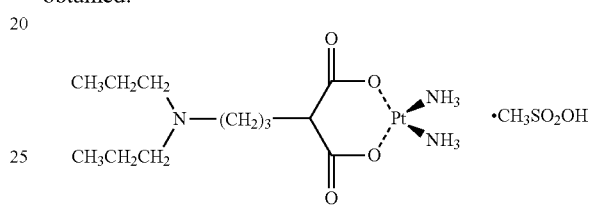

$^1$HNMR(D$_2$O)(ppm): δ3.62(t,1H), δ2.77(t,4H), δ2.70(t, 2H), δ1.74(m,2H), δ1.49(m,2H), δ1.25(m,4H), δ1.03(t,6H).

Both the free base and salt of the said compound are soluble in water. The solubility is 148 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C30.28% (theoretical 30.51%); H5.83% (theoretical 5.72%); N9.16% (theoretical 8.9%).

EXAMPLE 9

[2-(2-aminoethyl)-malonato].[cis-(1,2-cyclotrans-hexamethylene diamine)]platinum (II) phosphate Step 1: Same as [Embodiment 1] Step 1

Step 2: 2-(2-amino ethyl)-diethyl malonate

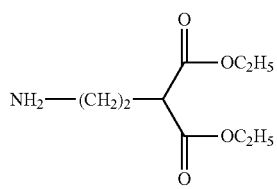

To the mixture of 2-bromethyl-diethyl malonate (106.5 g, 0.4 mol), anhydrous K$_2$CO$_3$ (55.0 g, 0.4 mol) in acetonitrile (500 ml), Excessive ammonia was added and the mixture was heated at 40~60° C. for 2-6 h; insoluble substance is filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (77.4 g) was obtained; the oil was purified by column chromatography to afford the title compound (34.7 g) and the yield was 42.7%.

Step 3: 2-(2-amino ethyl)-sodium malonate

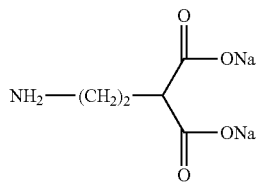

2M NaOH solution (2.5 mL) was added to 2-(2-amino ethyl)-diethyl malonate (603 mg, 2 mmol) in 20 mL flasks; and the mixture was stirred at room temperature for 45~60 h, 2-(2-amino ethyl)-malonic acid disodium salt solution was obtained.

Step 4: trans-hexamethylene diamine.diiodo-platinum (II)

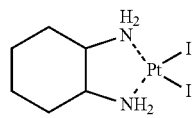

KI (6.640 g, 40 mmol) solution (50 ml) was added to potassium chloroplatinite ($K_2PtCl_4$) (2.075 g, 5 mmol) in water (50 ml), the mixture was stirred and heated to 40~60° C. away from light and oxygen for 0.5~2 h., and then trans-hexamethylene diamine (571 mg, 5 mmol) in water (50 ml) was added; the reaction mixture was kept under this condition for 0.5~2 h. Yellow solid product (2.709 g) was obtained by suction filtration and washed successively with water (10 ml×3 times) and diethyl ether (10 ml×3 times); the yield was 95.1%. Elemental analysis: C12.68% (theoretical 12.80%); H2.61% (theoretical 2.51%); N4.99% (theoretical 4.98%).

Step 5: Trans-cyclohexamethylene diamine.dihydrate platinum (II) sulphate

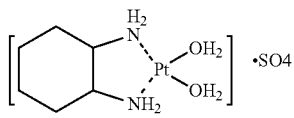

Stirring $Ag_2SO_4$ (625 mg, 2 mmol) in water (30 ml), trans-hexamethylene diamine.diiodo-platinum (II) (1.126 g, 2 mmol) was added and another part of water (40 ml) was added to the reaction mixture; the mixture was stirred and heated at 40~60° C. for 4~8 h. After removing AgI deposit by suction, The filtrate was the aqueous solution of the product.

Step 6: [2-(2-amino ethyl)-malonato].[cis-(1,2-trans-cyclohexamethylene diamine)]platinum (II) phosphate

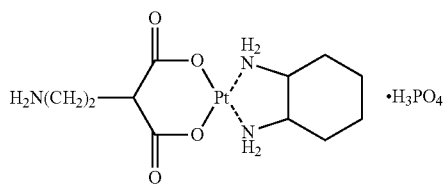

2-(2-amino ethyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h.; and then added 2.5 g silica into it; the mixture was stirred for 15 min and concentrated to dry, the residue was purified by column chromatography to afford the title compound (138 mg).

The said compound is soluble in water. The solubility is 275 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C29.31% (theoretical 29.07%); H4.82% (theoretical 4.63%); N9.17% (theoretical 9.25%).

$^1$HNMR ($D_2O$) (ppm): δ3.61(t,1H), δ2.78(t,2H), δ2.06(br, 2H), δ1.81(m,2H), δ1.74(m,2H), δ1.46(m,2H), δ1.21(br, 2H), δ1.01(m,2H).

EXAMPLE 10

2-(2-diethylamine ethyl)-malonic-cis-(1,2-trans-hexamethylene diamine) platinum (II) tosilate Step 1: Same as [Embodiment 1] Step 1

Step 2, 3: Same as [Embodiment 5] Step 2, 3

Step 4, 5: Same as [Embodiment 9] Step 4, 5

Step 6: [2-(2-diethylamine ethyl)-malonato].[cis-(1,2-trans-cyclohexamethylene diamine)]platinum (II) tosilate

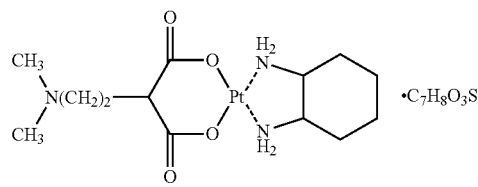

2-(2-dimethylamine ethyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (149 mg).

$^1$HNMR($D_2O$)(ppm): δ3.63(t,1H), δ2.68(s,6H), δ2.55(t, 2H), δ2.06(br,2H), δ1.81(m,2H), δ1.74(m,2H), δ1.46(m, 2H), δ1.21(br,2H), δ1.05(m,2H).

The said compound is soluble in water. The solubility is 233 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C32.34% (theoretical 32.37%); H5.42% (theoretical 5.19%); N8.47% (theoretical 8.71%).

EXAMPLE 11

[2-(3-dimethylamine propyl)-malonato].[cis-(1,2-trans-cyclohexamethylene diamine)]platinum (II) phosphate Step 1, 2, 3: Same as [Embodiment 5] Step 1, 2, 3

Step 4, 5: Same as [Embodiment 9] Step 4, 5

Step 6: [2-(3-dimethylamine propyl)-malonato].[cis-(1,2-trans-cyclohexamethylene diamine)]platinum (II) phosphate

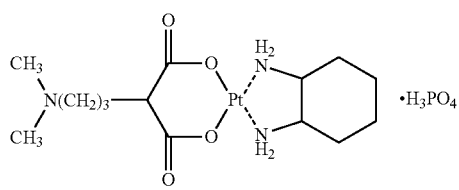

2-(3-dimethylamine propyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (131 mg).

$^1$HNMR($D_2O$)(ppm): δ3.61(t,1H), δ2.75(s,6H), δ2.69(t, 2H), δ2.06(br,2H), δ1.81(m,2H) δ1.74(m,2H), δ1.49(m,2H) δ1.46(m,2H), δ1.21(br,2H), δ1.02(m,2H)

The said compound is soluble in water. The solubility is 200 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C33.54% (theoretical 33.87%); H5.29% (theoretical 5.44%); N8.26% (theoretical 8.47%).

EXAMPLE 12

[2-(2-ethylamine ethyl)-malonato].[cis-(1, 2-trans-cyclohexamethylene diamine)]platinum (II) phosphate Step 1: Same as [Embodiment 1] Step 1

Step 2: 2-(2-ethylamine ethyl)-diethyl malonate

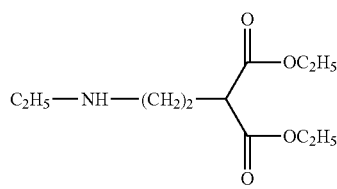

To the mixture of 2-bromethyl-diethyl malonate (106.2 g, 0.4 mol), anhydrous $K_2CO_3$ (55.0 g, 0.4 mol) in acetonitrile (500 ml), ethylamine (44.2 g, 1.0 mol) refrigerated was added and the mixture was heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (85.4 g) was obtained; the oil was purified by column chromatography to afford the title compound (36.8 g) and the yield was 39.7%.

Step 3: 2-(2-ethylamine ethyl)-sodium malonate

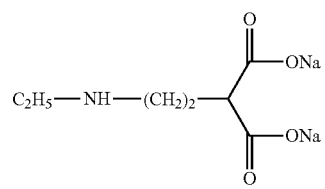

2M NaOH solution (2.5 mL) was added to 2-(2-ethylamine ethyl)-diethyl malonate (465 mg, 2 mmol) in 20 mL flasks; and the mixture was stirred at room temperature for 45~60 h, 2-(2-ethylamine ethyl)-malonic acid disodium salt solution was obtained.

Step 4, 5: Same as [Embodiment 9] Step 4, 5

Step 6: [2-(2-ethylamine ethyl)-malonato].[cis-(1,2-trans-cyclohexamethylene diamine)]platinum (II) phosphate

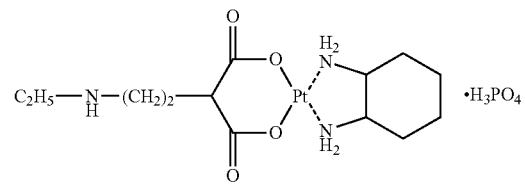

2-(2-ethylamine ethyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (137 mg).

$^1$HNMR($D_2O$)(ppm): δ3.60(t,1H), δ2.78(m,2H), δ2.70(t, 2H), 2.06(br,2H), 1.81(m,2H), δ1.70(m,2H), 1.46(m,2H), 1.21(br,2H), δ1.08(t,3H) 1.00(m,2H).

The said compound is soluble in water. The solubility is 221 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C32.55% (theoretical 32.43%); H5.21% (theoretical 5.0%); N8.56% (theoretical 8.73%).

EXAMPLE 13

2-(2-diethylamine ethyl)-malonic.cis-(1,2-trans-hexamethylene diamine) platinum (II) phosphate Step 1: Same as [Embodiment 1] Step 1

Step 2, 3: Same as [Embodiment 5] Step 2, 3

Step 4, 5: Same as [Embodiment 9] Step 4, 5

Step 6: [2-(2-diethylamine ethyl)-malonato].[cis-(1,2-trans-cyclohexamethylene diamine)]platinum (II) citrate

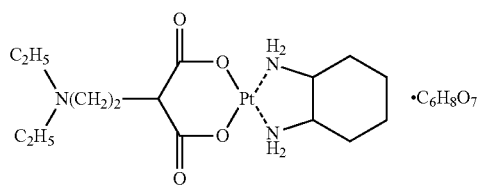

2-(2-diethylamine ethyl)-malonic acid disodium salt (2 mmol) solution was regulated to the pH 5~7 with citric acid (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (155 mg).
$^1$HNMR($D_2O$)(ppm): δ3.62(t,1H), δ2.78(m,4H), δ2.70(t, 2H), 2.06(br,2H), 1.81(m,2H), 1.70(m,2H), 1.46(m,2H), 1.21(br,2H), δ1.06(t,6H) 1.00(m,2H).

The said compound is soluble in water. The solubility is 180 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C35.01% (theoretical 35.29%); H5.43% (theoretical 5.69%); N8.51% (theoretical 8.24%).

EXAMPLE 14

[Embodiment 14] 2-(3-diethylamine propyl)-malonic.cis-(1,2-trans-hexamethylene diamine) platinum (II) phosphate Step 1: Same as [Embodiment 3] Step 1

Step 2, 3: Same as [Embodiment 6] Step 2, 3

Step 4, 5: Same as [Embodiment 9] Step 4, 5

Step 6: [2-(3-diethylamine propyl)-malonato].[cis-(1,2-trans-cyclohexamethylene diamine)]platinum (II) phosphate

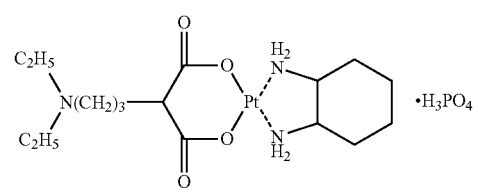

2-(2-diethylamine propyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (145 mg).
$^1$HNMR($D_2O$)(ppm): δ3.61(t,1H), δ2.78(q,4H), δ2.70(t, 2H), δ2.06(br,2H), δ1.81(m,2H), δ1.72(m,2H), δ1.46(m, 2H), δ1.49(m,2H), δ1.21(br,2H), δ1.08(t,6H), δ1.02(m,2H).

The said compound is soluble in water. The solubility is 156 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C36.37% (theoretical 36.64%); H6.13% (theoretical 5.92%); N8.22% (theoretical 8.02%).

EXAMPLE 15

2-(2-di-n-propylamine ethyl)-malonic.cis-(1,2-trans-hexamethylene diamine) platinum (II) phosphate Step 1: Same as [Embodiment 1] Step 1

Step 2, 3: Same as [Embodiment 7] Step 2, 3

Step 4, 5: Same as [Embodiment 9] Step 4, 5

Step 6: [2-(2-di-n-propylamine ethyl)-malonato].[cis-(1,2-trans-cyclohexamethylene diamine)]platinum (II) phosphate

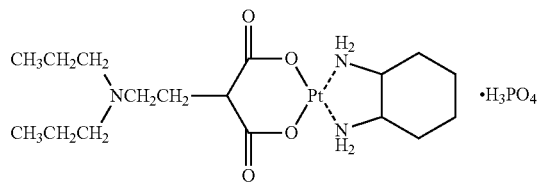

2-(2-di-n-propylamine ethyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (151 mg).
$^1$HNMR($D_2OX$)(ppm): δ3.60(t,1H), δ2.77(t,4H), δ2.70(t, 2H), δ2.06 (br,2H), δ1.81 (m,2H), δ1.78(m,2H), δ1.46 (m,2H), δ1.25(m,4H), δ1.21(br,2H), δ1.03 (t,6H) δ1.00 (m,2H).

The said compound is soluble in water. The solubility is 131 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C37.97% (theoretical 37.92%); H6.34% (theoretical 6.13%); N7.62% (theoretical 7.81%).

EXAMPLE 16

Embodiment 16

2-(3-di-n-propylamine propyl)-malonato].[cis-(1,2-trans-cyclohexamethylene diamine)]platinum (II) phosphate Step 1: Same as [Embodiment 3] Step 1

Step 2, 3: Same as [Embodiment 8] Step 2, 3

Step 4, 5: Same as [Embodiment 9] Step 4, 5

Step 6: [2-(3-di-n-propylamine propyl)-malonato]. [cis-(1, 2-trans-cyclohexamethylene diamine)]platinum (II) phosphate

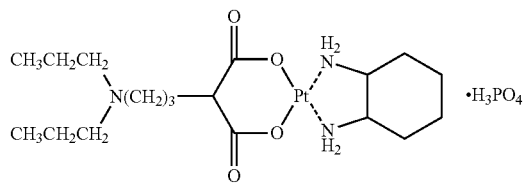

2-(3-di-n-propylamine propyl)-malonic acid disodium salt (2 mmol) solution was regulated to the pH 5~7 with $H_3PO_4$ (1M) and then aqueous trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (160 mg).

$^1$HNMR($D_2O$)(ppm): δ3.62(t,1H), δ2.77(t,4H), δ2.70(t, 2H), δ2.06 (br,2H), δ1.81 (m,2H), δ1.74(m,2H), δ1.49(m, 2H),δ1.46 (m,2H), δ1.25 (m,4H), δ1.21 (br,2H), δ1.03 (t,6H), δ1.00 (m,2H).

The said compound is soluble in water. The solubility is 109 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C39.14% (theoretical 39.13%); H6.38% (theoretical 6.34%); N7.69% (theoretical 7.61%).

EXAMPLE 17

[2-(3-diethylamine propyl)-malonato].[cis-(1,2-trans-diaminocyclopentane)]platinum (II) phosphate Step 1: Same as [Embodiment 3] Step 1

Step 2, 3: Same as [Embodiment 6] Step 2, 3

Synthesis Step 4: 1,2-trans-diaminocyclopentane

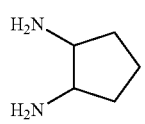

To the solution of cyclopentene (6.81 g, 100 mmol) in dichloromethane (30 ml), $Br_2$ (16.5 g, 103 mmol) was added dropwise slowly at −5~10° C. and stirred for 1~3 h, organic layer was washed with saturate sodium bicarbonate solution (10 ml×3 times) and dry with anhydrous MgSO4 for 2~3 h; After removal of solvent in vacuo, 1,2-trans-dibromo cyclopentane (20.56 g) as light yellow transparent oil was obtained; and the yield is 90.18%. Elemental analysis: C26.51% (theoretical 26.32%); H3.62% (theoretical 3.51%).

1,2-trans-dibromo cyclopentane (11.5 g, 50 mmol) and 30% ammonia ethanol solution (30 ml) was added into 100 ml pressure reactor; the mixture was heated to 40~60° C. and stirred for 6~8 h; After removal of solvent in vacuo to afford 1,2-trans-cyclopentylamine (4.015 g) as light yellow transparent oil; and the yield was 79.6%. Elemental analysis: C60.21% (theoretical 60%); H12.12% (theoretical 12%); N28.21% (theoretical 28%).

Step 5: 1,2-trans-diaminocyclopentane.diiodo-platinum (II)

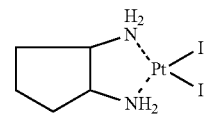

KI (6.630 g, 40 mmol) solution (50 ml) was added to potassium chloroplatinite ($K_2PtCl_4$) (2.073 g, 5 mmol) in water (50 ml), the mixture was stirred and heated to 40~60° C. away from light and oxygen for 0.5~2 h., and then 1,2-trans-diaminocyclopentane (501 mg, 5 mmol) in water (50 ml) was added; the reaction mixture was kept under this condition for 0.5~2 h. Yellow solid product (2.56 g) was obtained by suction filtration and washing successively with water (10 ml×3 times) and diethyl ether (10 ml×3 times); the yield was 93.1%.

Elemental analysis: C10.78% (theoretical 10.93%); H2.31% (theoretical 2.19%); N4.98% (theoretical 5.10%).

Step 6: 1,2-trans-diaminocyclopentane.dihydrate platinum (II) sulphate

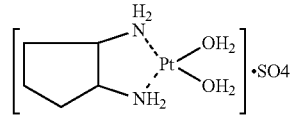

Stirring $Ag_2SO_4$(625 mg, 2 mmol) in water (30 ml), 1,2-trans-diaminocyclopentane.diiodo-platinum (II) (1.10 g, 2 mmol) was added and another part of water (40 ml) was added to the reaction mixture; the mixture was stirred and heated at 40~60° C. for 4~8 h. After removing AgI deposit by suction, the filtrate was the aqueous solution of the product.

Step 7: [2-(3-diethylamine propyl)-malonato].[cis-(1, 2-trans-diaminocyclopentane)]platinum (II) phosphate

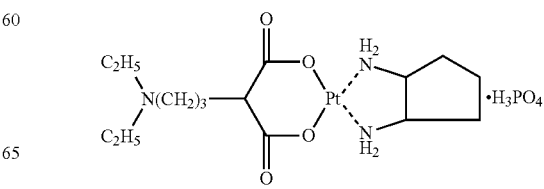

2-(3-diethylamine propyl)-malonic acid disodium salt (2 mmol) solution was regulated to the pH 5~7 with H$_3$PO$_4$ (1M) and then aqueous 1,2-trans-hexamethylene diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (153 mg).

$^1$HNMR(D$_2$O)(ppm): δ3.61(t,1H), δ2.78(q,4H), δ2.70(t, 2H), δ2.08(br,2H), δ1.83(m,2H), δ1.72(m,2H), δ1.49(m, 2H), δ1.42(m,2H), δ1.20(m,1H), δ1.08(t,6H), δ1.02(m,1H).

The said compound is soluble in water. The solubility is 178 mg/ml. It can be easily converted into other types of organic or inorganic salts through free base. It may be but not limited to sulphate, mesylate, tartrate, succinateacetate, citrate, tosilate, fumarate, etc. Free base elemental analysis: C35.58% (theoretical 35.29%); H5.61% (theoretical 5.69%); N8.37% (theoretical 8.24%).

EXAMPLE 18

2-(3-diethylamine propyl)-malonic.cis-(1,2-trans-aminocyclobutyl) platinum (II) succinate Step 1: Same as [Embodiment 3] Step 1

Step 2, 3: Same as [Embodiment 6] Step 2, 3

Step 4: 1,2-trans-aminocyclobutyl

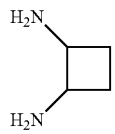

To the solution of cyclobutene (5.39 g, 100 mmol) in dichloromethane (30 ml), Br$_2$ (16.5 g, 103 mmol) was added dropwise slowly at −5~10° C. and stirred for 1~3 h, organic layer was washed with saturate sodium bicarbonate solution (10 ml×3 times) and dried with anhydrous MgSO$_4$ for 2~3 h; After removal of solvent in vacuo, 1,2-trans-dibromo cyclobutane (20.37 g) as light yellow transparent oil was obtained; and the yield was 95.19%. Elemental analysis: C22.53% (theoretical 22.43%); H2.61% (theoretical 2.80%).

1,2-trans-dibromo cyclobutane (10.65 g, 50 mmol) and 30% ammonia ethanol solution (30 ml) was added into 100 ml pressure reactor; the mixture was heated to 40~60° C. and stirred for 6~8 h; After removal of solvent in vacuo to afford 1,2-trans-diaminecyclobutane (3.723 g) as light yellow transparent oil; and the yield is 86.58%. Elemental analysis: C55.57% (theoretical 55.81%); H11.90% (theoretical 11.63%); N32.17% (theoretical 32.56%).

Step 5: 1,2-trans-aminocyclobutyl-diiodo-platinum (II)

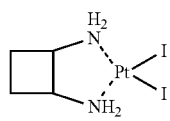

KI (6.630 g, 40 mmol) solution (50 ml) was added to potassium chloroplatinite (K$_2$PtCl$_4$) (2.075 g, 5 mmol) in water (50 ml), the mixture was stirred and heated to 40~60° C. away from light and oxygen for 0.5~2 h., and then 1,2-trans-diaminocyclobutane (501 mg, 5 mmol) in water (50 ml) was added; the reaction mixture shall be kept under this condition for 0.5~2 h. Yellow solid product (2.49 g) was obtained by suction filtration and washing successively with water (10 ml×3 times) and diethyl ether (10 ml×3 times); the yield was 90.8%.

Elemental analysis: C8.75% (theoretical 8.97%); H1.91% (theoretical 1.87%); N5.98% (theoretical 5.23%).

Step 6: 1,2-trans-aminocyclobutyl-dihydrate platinum (II) sulphate

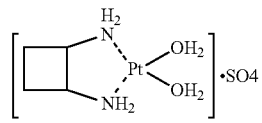

Stirring Ag$_2$SO$_4$ (625 mg, 2 mmol) in water (30 ml), 1,2-trans-diaminocyclobutane.diiodo-platinum (II) (1.07 g, 2 mmol) was added and another part of water (40 ml) was added to the reaction mixture; the mixture was stirred and heated at 40~60° C. for 4~8 h. After removing AgI deposit by suction, The filtrate was the aqueous solution of the product.

Step 7: [2-(3-diethylamine propyl)-malonato].[cis-(1,2-trans-diaminocyclobutene)]platinum (II) succinate

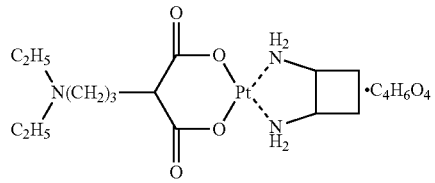

2-(3-diethylamine propyl)-malonic acid disodium salt (2 mmol) solution was regulated to the pH 5~7 with succinic acid (C$_4$H$_6$O$_4$, 1M) and then aqueous 1, 2-trans-cyclobutyl diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (143 mg).

$^1$HNMR(D$_2$O)(ppm): δ3.62(t,1H), δ2.78(q,4H), δ2.70(t, 2H), δ2.08(br,2H), δ1.85(m,2H), δ1.72(m,2H), δ1.49(m, 2H), δ1.44(m,2H), δ1.08(t,6H).

The said compound is soluble in water. The solubility is 208 mg/ml. It can be easily converted into other types of organic or inorganic salts through free base. It may be but not limited to sulphate, mesylate, tartrate, succinateacetate, citrate, tosilate, fumarate, etc. Free base elemental analysis: C34.57% (theoretical 33.87%); H5.62% (theoretical 5.44%); N8.39% (theoretical 8.47%).

EXAMPLE 19

[2-(3-diethylamine propyl)-malonato].[cis-(1,2-trans-cyclopropyl diamine)]platinum (II) phosphate Step 1: Same as [Embodiment 3] Step 1

Step 2, 3: Same as [Embodiment 6] Step 2, 3

Step 4: 1,2-trans-cyclopropyl diamine.diiodo-platinum (II)

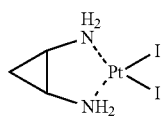

KI (6.630 g, 40 mmol) solution (50 ml) was added to potassium chloroplatinite (K$_2$PtCl$_4$) (2.075 g, 5 mmol) in water (50 ml), the mixture was stirred and heated to 40~60° C. away from light and oxygen for 0.5.2 h., and then 1,2-trans-cyclopropyl diamine (361 mg, 5 mmol) in water (50 ml) was added; the reaction mixture was kept under this condition for 0.5.2 h. Yellow solid product (2.39 g) was obtained by suction filtration and washing successively with water (10 ml×3 times) and diethyl ether (10 ml×3 times), the yield was 91.8%.

Elemental analysis: C6.97% (theoretical 6.91%); H1.41% (theoretical 1.54%); N5.47% (theoretical 5.37%).

Step 5: 1,2-trans-cyclopropyl diamine.dihydrate platinum (II) sulphate

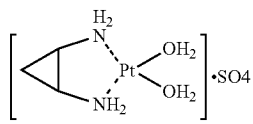

Stirring Ag$_2$SO$_4$ (624 mg, 2 mmol) in water (30 ml), 1,2-trans-cyclopropyl diamine.diiodo-platinum (II) (1.04 g, 2 mmol) was added and another part of water (30 ml) was added to the reaction mixture; the mixture was stirred and heated at 40~60° C. for 4.8 h. After removing AgI deposit by suction, The filtrate was the aqueous solution of the product.

Step 6: [2-(3-diethylamine propyl)-malonato].[cis-(1,2-trans-cyclopropyl diamine)]platinum (II) phosphate

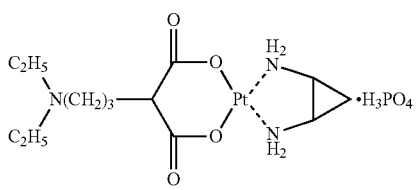

2-(3-diethylamine propyl)-malonic acid disodium salt (2 mmol) solution was regulated to the pH 5~7 with H$_3$PO$_4$ (1M) and then aqueous 1,2-trans-cyclopropyl diamine.dihydrate platinum (II) sulphate was poured into reaction mixture; the mixture was heated in water bath to 40~60° C. for 4-8 h. and then added 2.5 g silica into it, the mixture was stirred for 15 min and concentrated to dry, the residue was purified by column chromatography to afford the title compound (137 mg).

$^1$HNMR(D$_2$O)(ppm): δ3.61(t,1H), δ2.78(q,4H), δ2.70(t, 2H), 2.10(br 2H), 1.87(m,1H), δ1.75(m,2H), δ1.48(m,2H), 1.43(m,1H), 1.09(t,6H).

The said compound is soluble in water. The solubility is 218 mg/ml. It can be easily converted into other types of organic or inorganic salts through ionization. It may be but not limited to sulphate, mesylate, tartrate, succinateacetate, citrate, tosilate, fumarate, etc. Free base elemental analysis: C32.53% (theoretical 32.37%); H5.12% (theoretical 5.19%); N8.99% (theoretical 8.71%).

EXAMPLE 20

2-(2-dimethylamine ethyl)-malonic-cis-1,2-ethylenediamine platinum (II) tosilate Step 1: Same as [Embodiment 1] Step 1

Step 2, 3: Same as [Embodiment 2] Step 2, 3

Step 4: 1,2-ethylenediamine.diiodo-platinum (II)

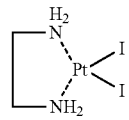

KI (6.64 g, 40 mmol) solution (40 ml) was added to potassium chloroplatinite (K$_2$PtCl$_4$) (2.076 g, 5 mmol) in water (50 ml), the mixture was stirred and heated to 40~60° C. away from light and oxygen for 0.5~2 h., and then 1,2-ethylenediamine (301 mg, 5 mmol) refrigerated in water (50 ml) was added; the reaction mixture shall be kept under this condition for 0.5~2 h. Yellow solid product (2.254 g) was obtained by suction filtration and washing successively with water (10 ml×3 times) and diethyl ether (10 ml×3 times), the yield was 89.8%.

Elemental analysis: C4.77% (theoretical 4.72%); H1.41% (theoretical 1.57%); N5.41% (theoretical 5.50%).

Step 5: 1,2-ethyldiamine.dihydrate platinum (II) sulphate

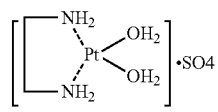

Stirring Ag$_2$SO$_4$ (625 mg, 2 mmol) in water (30 ml), 1,2-ethylenediamine.diiodo-platinum (II) (1.02 g, 2 mmol) was added and another part of water (30 ml) was added to the reaction mixture, the mixture was stirred and heated at 40~60° C. for 4.8 h. After removing AgI deposit by suction, the filtrate was the aqueous solution of the product.

Step 6: [2-(2-dimethylamine ethyl)-malonato].[cis-1,2-ethylenediamine] platinum (II) tosilate

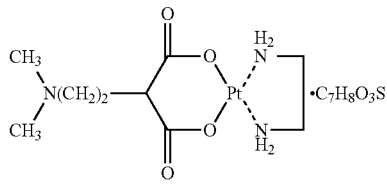

2-(3-dimethylamine ethyl)-malonic acid disodium salt (2 mmol) solution was regulated to the pH 5~7 with p-toluene-sulfonic acid ($C_7H_8O_3S$, 1M) and then aqueous 1,2-ethylene-diamine.dihydrate platinum (II) sulphate was poured into reaction mixture; the mixture was heated in water bath to 40~60° C. for 4-8 h. and then added 2.5 g silica into it, the mixture was stirred for 15 min and concentrated to dry, the residue was purified by column chromatography to afford the title compound (140 mg).

$^1$HNMR($D_2O$)(ppm): δ3.63(t,1H), δ2.68(s,6H), δ2.55(t, 2H), δ2.24-2.32(br,4H), δ1.74(m,2H).

The said compound is soluble in water. The solubility is 269 mg/ml. It can be easily converted into other types of organic or inorganic salts through free base. It may be but not limited to sulphate, mesylate, tartrate, succinateacetate, citrate, tosilate, fumarate, etc. Free alkali elemental analysis: C24.95% (theoretical 25.23%); H4.32% (theoretical 4.44%); N9.92% (theoretical 9.81%).

EXAMPLE 21

2-(2-diethylamine ethyl)-malonic.cis-1,3-propane diamine platinum (II) phosphate Step 1: Same as [Embodiment 1] Step 1

Step 2, 3: Same as [Embodiment 5] Step 2, 3

Step 4: 1,3-propane diamine.diiodo-platinum (II)

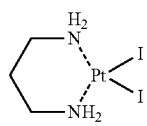

KI (6.64 g, 40 mmol) solution (40 ml) was added to potassium chloroplatinite ($K_2PtCl_4$) (2.073 g, 5 mmol) in water (50 ml), the mixture was stirred and heated to 40~60° C. away from light and oxygen for 0.5~2 h., and then 1,3-propane diamine (commercially available) refrigerated (372 mg, 5 mmol) in water (50 ml) was added; the reaction mixture was kept under this condition for 0.5~2 h. Yellow solid product (2.281 g) was obtained by suction filtration and washing successively with water (10 ml×3 times) and diethyl ether (10 ml×3 times); the yield was 87.6%.

Elemental analysis: C6.77% (theoretical 6.88%); H1.79% (theoretical 1.91%); N5.43% (theoretical 5.35%).

Step 5: 1,3-propyl diamine.dihydrate platinum (II) sulphate

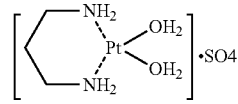

Stirring $Ag_2SO_4$ (625 mg, 2 mmol) in water (30 ml), 1,3-propyl diamine.diiodo-platinum (II) (1.04 g, 2 mmol) was added and another part of water (30 ml) was added to the reaction mixture; the mixture was stirred and heated at 40~60° C. for 4~8 h. After removing AgI deposit by suction, The filtrate was the aqueous solution of the product.

Step 6: [2-(2-diethylamine ethyl)-malonato].[cis-1,3-propyl diamine] platinum (II) phosphate

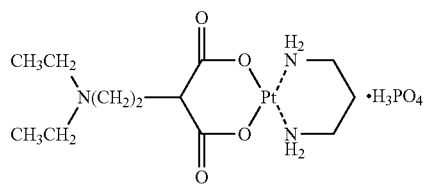

2-(3-dimethylamine ethyl)-malonic acid disodium salt (2 mmol) solution was regulated to the pH 5~7 with H3PO4 (1M) and then aqueous 1,3-propyl diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (142 mg).

$^1$HNMR($D_2O$)(ppm): δ3.60(t,1H), δ2.78(q,4H), δ2.70(m, 2H), δ2.26(t,4H), δ1.70(m,2H), δ1.45(m,2H), δ1.08(t,6H).

The said compound is soluble in water. The solubility is 231 mg/ml. It can be easily converted into other types of organic or inorganic salts through free base. It may be but not limited to sulphate, mesylate, tartrate, succinateacetate, citrate, tosilate, fumarate, etc. Free base elemental analysis: C30.91% (theoretical 30.64%); H5.32% (theoretical 5.32%); N8.98% (theoretical 8.94%).

EXAMPLE 22

[2-(2-di-n-propylamine ethyl)-malonato].[cis-1,4-butanediamine] platinum (II) phosphate Step 1: Same as [Embodiment 1] Step 1

Step 2, 3: Same as [Embodiment 7] Step 2, 3

Step 4: 1,4-butyldiamine.diiodo-platinum (II)

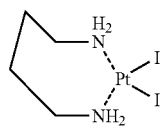

KI (6.635 g, 40 mmol) solution (40 ml) was added to potassium chloroplatinite (K$_2$PtCl$_4$) (2.071 g, 5 mmol) in water (50 ml), the mixture was stirred and heated to 40~60° C. away from light and oxygen for 0.5~2 h., and then 1,4-butyldiamine (commercially available) refrigerated (372 mg, 5 mmol) in water (50 ml) was added; the reaction mixture was kept under this condition for 0.5~2 h. Yellow solid product (2.365 g) was obtained by suction filtration and washing successively with water (10 ml×3 times) and diethyl ether (10 ml×3 times), the yield was 88.1%.

Elemental analysis: C8.69% (theoretical 8.94%); H2.39% (theoretical 2.23%); N5.44% (theoretical 5.21%).

Step 5: 1,4-butyldiamine.dihydrate platinum (II) sulphate

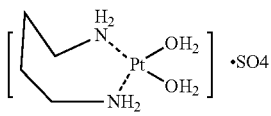

Stirring Ag$_2$SO$_4$ (624 mg, 2 mmol) in water (30 ml), 1,4-butyldiamine.diiodo-platinum (II) (1.04 g, 2 mmol) was added and another part of water (30 ml) was added to the reaction mixture, the mixture was stirred and heated at 40~60° C. for 4~8 h. After removing AgI deposit by suction, The filtrate was the aqueous solution of the product.

Step 6: [2-(2-di-n-propylamine ethyl)-malonato].[1,4-butyldiamine] platinum (II) phosphate

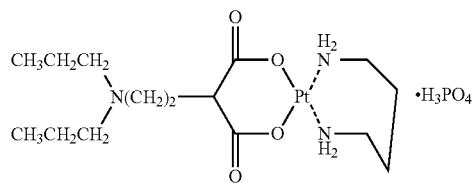

2-(2-di-n-propylamine ethyl)-malonic acid disodium salt (2 mmol) solution was regulated to the pH 5~7 with H$_3$PO$_4$ (1M) and then aqueous 1,4-butyldiamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (149m g).

$^1$HNMR(D$_2$O)(ppm): δ3.60(t,1H), δ2.72(m,4H), δ2.52(m, 4H), δ2.36(t,2H), δ1.82(m,2H), δ1.55 (t,4H), δ1.39 (m,4H), δ1.05(t,6H).

The said compound is soluble in water. The solubility is 181 mg/ml. It can be easily converted into other types of organic or inorganic salts through free base. It may be but not limited to sulphate, mesylate, tartrate, succinateacetate, citrate, tosilate, fumarate, etc. Free base elemental analysis: C34.93% (theoretical 35.16%); H6.22% (theoretical 6.05%); N8.17% (theoretical 8.20%).

EXAMPLE 23

2-(2-ethylic ethylamine)-malonic.cis-1,2-(1,2-dihydroxymethyl)-ethyldiamine platinum (II) phosphate Step 1: Same as [Embodiment 1] Step 1

Step 2, 3: Same as [Embodiment 5] Step 2, 3

Step 4: 1,2-(1,2-dihydroxymethyl)-ethyldiamine.diiodo-platinum (II)

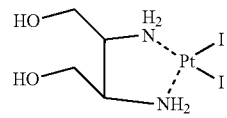

KI (6.637 g, 40 mmol) solution (40 ml) was added to potassium chloroplatinite (K$_2$PtCl$_4$) (2.073 g, 5 mmol) in water (50 ml), the mixture was stirred and heated to 40~60° C. away from light and oxygen for 0.5~2 h., and then 1,2-(1,2-dihydroxymethyl)ethyldiamine (601 mg, 5 mmol) in water (50 ml) was added; the reaction mixture was kept under this condition for 0.5~2 h. Yellow solid product (2.163 g) was obtained by suction filtration and washing successively with water (10 ml×3 times) and diethyl ether (10 ml×3 times), the yield was 79.96%.

Elemental analysis: C8.65% (theoretical 8.44%); H2.39% (theoretical 2.11%); N5.03% (theoretical 4.92%).

Step 5: 1,2-(1,2-dihydroxymethyl)-ethyldiamine.dihydrate platinum (II) sulphate

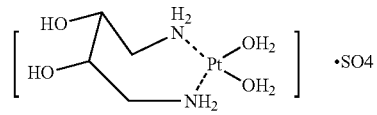

Stirring Ag$_2$SO$_4$ (624 mg, 2 mmol) in water (30 ml), 1,2-(1,2-dihydroxymethyl)-ethyldiamine.diiodo-platinum (II) (1.04 g, 2 mmol) was added and another part of water (30 ml) was added to the reaction mixture; the mixture was stirred and heated at 40~60° C. for 4~8 h. After removing AgI deposit by suction, The filtrate was the aqueous solution of the title compound.

Step 6: [2-(2-diethylamine ethyl)-malonato].[cis-1,2-(1,2-dihydroxymethyl)-ethyldiamine]platinum (II) phosphate

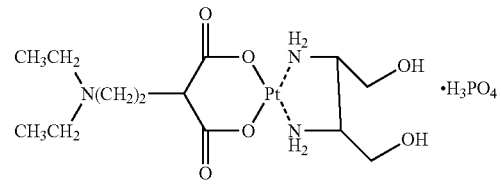

2-(2-diethylamine ethyl)-malonic acid disodium salt (2 mmol) solution was regulated to the pH 5~7 with H3PO4 (1M) and then aqueous 1,2-(1,2-dihydroxymethyl)-ethyldiamine.dihydrate platinum (II) sulphate was poured into reaction mixture; the mixture was heated in water bath to 40~60° C. for 4-8 h. and then added 2.5 g silica into it, the mixture was stirred for 15 min and concentrated to dry, the residue was purified by column chromatography to afford the title compound (13 mg).

¹HNMR(D₂O)(ppm): δ3.60(t,1H), δ3.03(d,4H), δ2.77-2.92 (m,4H), δ2.67(m,2H), δ2.40(t,2H), δ1.75(t,2H), δ1.08 (t,6H).

The said compound is soluble in water. The solubility is 206 mg/ml. It can be easily converted into other types of organic or inorganic salts through free base. It may be but not limited to sulphate, mesylate, tartrate, succinateacetate, citrate, tosilate, fumarate, etc. Free base elemental analysis: C30.43% (theoretical 30.23%); H5.22% (theoretical 5.23%); N8.16% (theoretical 8.14%).

EXAMPLE 24

2-(2-dimethylamine ethyl)-malonic.cis-1,3-(2,2-hydroxymethyl)-propane diamine platinum (II) phosphate Step 1: Same as [Embodiment 1] Step 1

Step 2, 3: Same as [Embodiment 2] Step 2, 3

Step 4: 1,3-(2,2-dihydroxymethyl)-propyl diamine.diiodo-platinum (II)

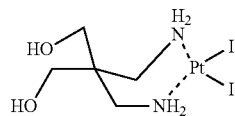

KI (6.637 g, 40 mmol) solution (40 ml) was added to potassium chloroplatinite (K₂PtCl₄) (2.0734 g, 5 mmol) in water (50 ml), the mixture was stirred and heated to 40~60° C. away from light and oxygen for 0.5~2 h., and then 1,3-(2,2-dihydroxymethyl)-propyl diamine (671 mg, 5 mmol) in water (50 ml) was added; the reaction mixture shall be kept under this condition for 0.5~2 h. Yellow solid product (2.163 g) was obtained by suction filtration and washing successively with water (10 ml×3 times) and diethyl ether (10 ml×3 times), the yield was 79.96%.

Elemental analysis: C10.37% (theoretical 10.29%); H2.49% (theoretical 2.40%); N5.01% (theoretical 4.80%).

Step 5: 1,3-(2,2-hydroxymethyl)-propane diamine.dihydrate platinum (II) sulphate

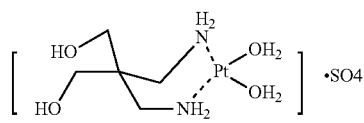

Stirring Ag₂SO₄ (624 mg, 2 mmol) in water (30 ml), 1,3-(2,2-dihydroxymethyl)-propyl diamine.diiodo-platinum (II) (1.04 g, 2 mmol) was added and another part of water (30 ml) was added to the reaction mixture; the mixture was stirred and heated at 40~60° C. for 4~8 h. After removing AgI deposit by suction, The filtrate was the aqueous solution of the title compound.

Step 6: [2-(2-dimethylamine ethyl)-malonato].[cis-1,3-(2,2-hydroxymethyl)-propane diamine]platinum (II) phosphate

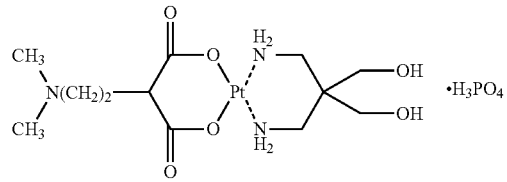

2-(2-dimethylamine ethyl)-malonic acid disodium salt (2 mmol) solution was regulated to the pH 5~7 with H3PO4 (1M) and then aqueous 1,3-(2,2-dihydroxymethyl)-propyl diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (137 mg).

¹HNMR (D₂O)(ppm): δ3.62(t,1H), δ3.49(s,4H), δ2.75(s, 6H), δ2.70 (t,2H), δ2.57(s,4H), δ1.70(m,2H).

The said compound is soluble in water. The solubility is 231 mg/ml. It can be easily converted into other types of organic or inorganic salts through free base. It may be but not limited to sulphate, mesylate, tartrate, succinateacetate, citrate, tosilate, fumarate, etc. Free base elemental analysis: C28.49% (theoretical 28.69%); H5.20% (theoretical 4.98%); N8.19% (theoretical 8.37%).

EXAMPLE 25

2-(2-dimethylamine ethyl)-malonic.cis-1,2-diaminomethylcyclobutane platinum (II) phosphate Step 1: Same as [Embodiment 1] Step 1

Step 2, 3: Same as [Embodiment 2] Step 2, 3

Step 4: trans-1,2-diaminomethylcyclobutane.diiodo-platinum (II)

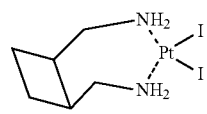

KI (6.64 g, 40 mmol) solution (40 ml) was added to potassium chloroplatinite (K₂PtCl₄) (2.075 g, 5 mmol) in water (50 ml), the mixture was stirred and heated to 40~60° C. away from light and oxygen for 0.5~2 h., and then trans-1,2-diaminomethylcyclobutane (571 mg, 5 mmol) in water (50 ml) was added; the reaction mixture shall be kept under this condition for 0.5~2 h. Yellow solid product (2.251 g) was obtained by suction filtration and washing successively with water (10 ml×3 times) and diethyl ether (10 ml×3 times), the yield was 79.96%.

Elemental analysis: C12.61% (theoretical 12.79%); H2.45% (theoretical 2.49%); N5.11% (theoretical 4.97%).

Step 5: trans-1,2-diaminomethylcyclobutane.dihydrate platinum (II) sulphate

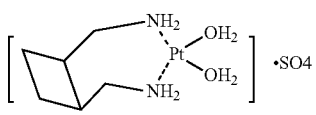

Stirring Ag$_2$SO$_4$ (624 mg, 2 mmol) in water (30 ml), trans-1,2-diaminomethylcyclobutane.diiodo-platinum (II) (1.12 g, 2 mmol) was added and another part of water (30 ml) was added to the reaction mixture; the mixture was stirred and heated at 40~60° C. for 4~8 h. After removing AgI deposit by suction, The filtrate was the aqueous solution of the title compound.

Step 6: [2-(2-dimethylamine ethyl)-malonato].[cis-trans-1,2-diaminomethylcyclobutane]platinum (II) phosphate

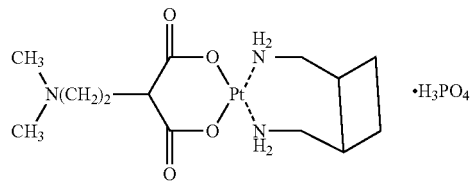

2-(2-dimethylamine ethyl)-malonic acid disodium salt (2 mmol) solution was regulated to the pH 5~7 with H3PO4 (1M) and then aqueous trans-1,2-diaminomethylcyclobutane.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (151 mg).

$^1$HNMR(D$_2$O)(ppm): δ3.62(t,1H), δ2.75 (s,6H), δ2.70 (t,2H), δ2.23(d,4H), δ1.95(m,2H), δ1.70 (m,2H), δ1.44(m,4H)

The said compound is soluble in water. The solubility is 185 mg/ml. It can be easily converted into other types of organic or inorganic salts through free base. It may be but not limited to sulphate, mesylate, tartrate, succinateacetate, citrate, tosilate, fumarate, etc. Free base elemental analysis: C32.49% (theoretical 32.37%); H5.36% (theoretical 5.19%); N8.75% (theoretical 8.71%).

EXAMPLE 26

2-(2-diethylamine ethyl)-malonic.cis-1,4-(trans-2,3-cyclobutyl)-butanediamine platinum (II) phosphate Step 1: Same as [Embodiment 1] Step 1

Step 2, 3: Same as [Embodiment 5] Step 2, 3

Step 4, 5: Same as [Embodiment 25] Step 4, 5

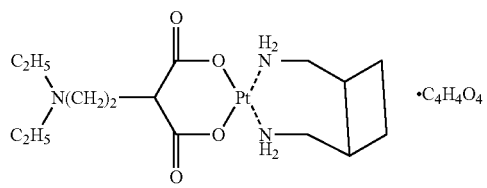

Step 6: 2-(2-diethylamine ethyl)-malonic acid disodium salt (2 mmol) solution was regulated to the pH 5~7 with fumaric acid (C$_4$H$_4$O$_4$, 1M) and then aqueous trans-1,2-diaminomethylcyclobutane.dihydrate platinum (II) sulphate was poured into reaction mixture; the mixture was heated in water bath to 40~60° C. for 4-8 h. and then added 2.5 g silica into it, the mixture was stirred for 15 min and concentrated to dry, the residue was purified by column chromatography to afford the title compound (153 mg).

$^1$HNMR(D$_2$O)(ppm): δ3.62(t,1H), δ2.78(m,4H), δ2.70(t,2H), δ2.23(d,4H), δ1.89 (m,2H), δ1.72 (m,2H), δ1.08(t 6H), δ1.44(m,4H).

The said compound is soluble in water. The solubility is 176 mg/ml. It can be easily converted into other types of organic or inorganic salts through free base. It may be but not limited to sulphate, mesylate, tartrate, succinateacetate, citrate, tosilate, fumarate, etc. Free base elemental analysis: C35.41% (theoretical 35.29%); H5.50% (theoretical 5.69%); N8.17% (theoretical 8.24%).

EXAMPLE 27

2-(2-diethylamine ethyl)-malonic-cis-1,4-cyclohexyl diamine platinum (II) phosphate Step 1: Same as [Embodiment 1] Step 1

Step 2, 3: Same as [Embodiment 5] Step 2, 3

Step 4: 1,4-cyclohexyl diamine.diiodo-platinum (II)

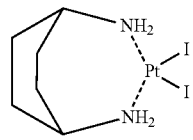

KI (6.64 g, 40 mmol) solution (40 ml) was added to potassium chloroplatinite (K$_2$PtCl$_4$) (2.071 g, 5 mmol) in water (50 ml), the mixture was stirred and heated to 40~60° C. away from light and oxygen for 0.5~2 h., and then 1,4-cyclohexyldiamine (572 mg, 5 mmol) in water (50 ml) was added; the reaction mixture was kept under this condition for 0.5~2 h. Yellow solid product (2.163 g) was obtained by suction filtration and washing successively with water (10 ml×3 times) and diethyl ether (10 ml×3 times), the yield was 76.84%.

Elemental analysis: C12.74% (theoretical 12.79%); H2.45% (theoretical 2.49%); N5.17% (theoretical 4.97%).

Step 5: 1,4-cyclohexanediamine.dihydrate platinum (II) sulphate

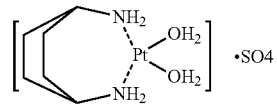

Stirring Ag$_2$SO$_4$ (624 mg, 2 mmol) in water (30 ml), 1,4-cyclohexanediamine.diiodo-platinum (II) (1.125 g, 2 mmol) was added and another part of water (30 ml) was added to the reaction mixture; the mixture was stirred and heated at 40~60° C. for 4~8 h. After removing AgI deposit by suction, The filtrate was the aqueous solution of the title compound.

Step 6: [2-(2-diethylamine ethyl)-malonato].[cis-1,4-cyclohexyl diamine] platinum (II) phosphate

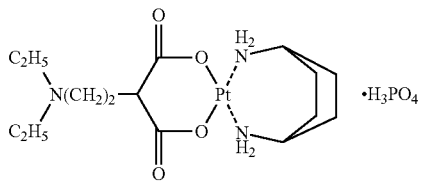

2-(2-diethylamine ethyl)-malonic acid disodium salt (2 mmol) solution was regulated to the pH 5~7 with H3PO4 (1M) and then aqueous t1, 4-cyclohexanediamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (140 mg).

$^1$HNMR(D$_2$O)(ppm): δ3.62(t,1H), δ2.78(m,4H), δ2.70(t, 2H), 2.05(m,2H), δ1.72 (m,2H), δδ1.53-1.78(m,8H), δ1.08 (t,6H).

The said compound is soluble in water. The solubility is 145 mg/ml. It can be easily converted into other types of organic or inorganic salts through free base. It may be but not limited to sulphate, mesylate, tartrate, succinateacetate, citrate, tosilate, fumarate, etc. Free base elemental analysis: C35.51% (theoretical 35.29%); H5.57% (theoretical 5.69%); N8.06% (theoretical 8.24%).

EXAMPLE 28

2-(2-diethylamine ethyl)-malonic.cis-1,3-(2,2-(4-oxacyclohexyl))-propane diamine platinum (II) phosphate Step 1: Same as [Embodiment 1] Step 1

Step 2, 3: Same as [Embodiment 5] Step 2, 3

Step 4: 1,3-(2,2-(4-oxacyclohexyl))-propyl diamine-.diiodo-platinum (II)

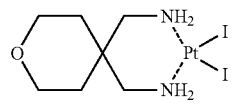

KI (6.64 g, 40 mmol) solution (40 ml) was added to potassium chloroplatinite (K$_2$PtCl$_4$) (2.071 g, 5 mmol) in water (50 ml), the mixture was stirred and heated to 40~60° C. away from light and oxygen for 0.5~2 h., and then 1,3-(2,2-(4-oxacyclohexyl))-propyl diamine (572 mg, 5 mmol) in water (50 ml) was added; the reaction mixture was kept under this condition for 0.5~2 h. Yellow solid product (2.547 g) was obtained by suction filtration and washing successively with water (10 ml×3 times) and diethyl ether (10 ml×3 times), the yield was 85.91%.

Elemental analysis: C14.35% (theoretical 14.17%); H2.75% (theoretical 2.70%); N4.72% (theoretical 4.72%).

Step 5: 1,3-(2,2-(4-oxacyclohexyl))-propyl diamine.dihydrate platinum (II) sulphate

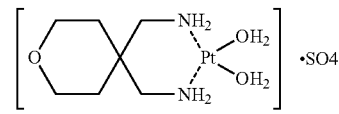

Stirring Ag$_2$SO$_4$ (623 mg, 2 mmol) in water (30 ml), 1,3-(2,2-(4-oxacyclohexyl))-propyl diamine.diiodo-platinum (II) (1.125 g, 2 mmol) was added and another part of water (30 ml) was added to the reaction mixture; the mixture was stirred and heated at 40~60° C. for 4~8 h. After removing AgI deposit by suction, The filtrate was the aqueous solution of the title compound.

Step 6: [2-(2-diethylamine ethyl)-malonato].[cis-1,3-(2,2-(4-oxacyclohexyl))-propyldiamine]platinum (II) phosphate

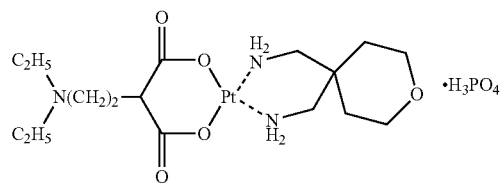

2-(2-diethylamine ethyl)-malonic acid disodium salt (2 mmol) solution was regulated to the pH 5~7 with H3PO4 (1M) and then aqueous 1,3-(2,2-(4-oxacyclohexyl))-propyl diamine.dihydrate platinum (II) sulphate was poured into reaction mixture; the mixture was heated in water bath to 40~60° C. for 4-8 h. and then added 2.5 g silica into it; the mixture was stirred for 15 min and concentrated to dry, the residue was purified by column chromatography to afford the title compound (159 mg).

$^1$HNMR(D$_2$O)(ppm): δ3.70 (t,4H), δ3.60(t,1H), δ2.78(m, 4H), δ2.70 (t,2H), δ2.12(s,4H), δ1.89(m,2H), δ1.52(t,4H), δ1.08 (t,6H).

The said compound is soluble in water. The solubility is 178 mg/ml. It can be easily converted into other types of organic or inorganic salts through free base. It may be but not limited to sulphate, mesylate, tartrate, succinateacetate, citrate, tosilate, fumarate, etc. Free base elemental analysis: C35.27% (theoretical 35.56%); H5.51% (theoretical 5.74%); N8.04% (theoretical 7.78%).

EXAMPLE 29

2-(3-(1-piperidyl)-propyl)-malonic-cis-diamino platinum (II) phosphate

Step 1: Same as [Embodiment 3] Step 1

Step 2: 2-(3-(1-piperidyl)-propyl)-diethyl malonate

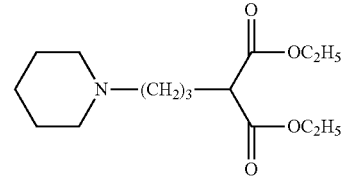

To the mixture of 2-bropropyl-diethyl malonate (113.7 g, 0.4 mol), anhydrous $K_2CO_3$ (55.40 g, 0.4 mol) in acetonitrile (500 ml), piperidine solution (85.0 g, 1.0 mol) was added into mixture which was then heated at 40~60° C. for 2-6 h; insoluble substance is filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (99.3 g) was obtained; the oil was purified by column chromatography to afford the title compound (35.57 g) and the yield was 31.2%.

Step 3: 2-(3-(1-piperidyl)-propyl)-diethyl malonate disodium salt

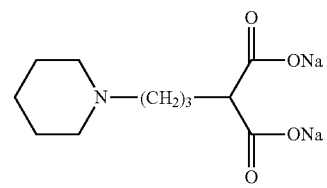

2M NaOH solution (2.5 mL) was added to 2-(3-(1-piperidyl)-propyl)-diethyl malonate (572 mg, 2 mmol) in 20 mL flasks; and the mixture was stirred at room temperature for 45~60 h, 2-(3-(1-piperidyl)-propyl)-diethyl malonate disodium salt solution was obtained.

Step 4, 5: Same as [Embodiment 1] Step 4, 5

Step 6: [2-(3-(1-piperidyl)-propyl)-malonato].[cis-diamine]platinum (II) phosphate

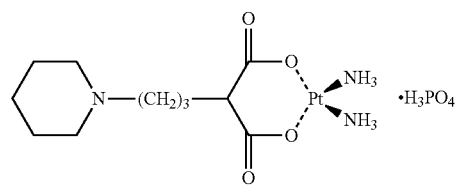

2-(3-(1-piperidyl)-propyl)-malonic acid disodium salt (2 mmol) solution was regulated to the pH 5~7 with H3PO4 (1M) and then aqueous cis-diamine.dihydrate platinum (II) sulphate was poured into reaction mixture; the mixture was heated in water bath to 40~75° C. for 4-6 h, the mixture was concentrated to certain volume and the residue was standstill at room temperature; the title compound (136 mg) was obtained by suction.

The said compound is soluble in water. The solubility is 159 mg/ml. It can be easily converted into other types of organic or inorganic salts through free base. It may be but not limited to sulphate, mesylate, tartrate, succinate, acetate, citrate, tosilate, fumarate, etc. Free base elemental analysis: C28.24% (theoretical 28.79%); H4.93% (theoretical 5.05%); N9.02% (theoretical 9.23%).

$^1$HNMR($D_2O$)(ppm): δ3.62(t,1H), δ2.83(m,4H), δ2.70(m,2H), δ1.85(m,2H), δ1.77(m,4H), δ1.52(m,2H), δ1.37(m,2H).

EXAMPLE 30

2-(3-(1-pyrrolidyl)-propyl)-malonic-cis-diamino platinum (II) phosphate

Step 1: Same as [Embodiment 3] Step 1

Step 2: 2-(3-(1-pyrrolidyl)-propyl)-diethyl malonate

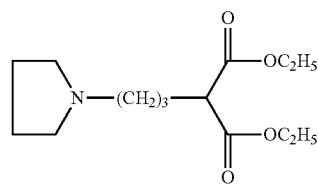

To the mixture of 2-bropropyl-diethyl malonate (113.6 g, 0.4 mol), anhydrous $K_2CO_3$ (55.73 g, 0.4 mol) in acetonitrile (500 ml), pyrrolidine solution (71.1 g, 1.0 mol) was added into mixture which was then heated at 40~60° C. for 2-6 h; insoluble substance was filtered out and the filtrate was concentrated in vacuo; the residues was dissolved with 1000 ml ethyl acetate; organic phase was washed with saturate NaCl aqueous solution (250 ml×3 times) and dried over anhydrous MgSO4 overnight; after removal of solvent in vacuo, light yellow oil (95.9 g) was obtained; the oil was purified by column chromatography to afford the title compound (31.87 g) and the yield was 29.4%.

Step 3: 2-(3-(1-pyrrolidyl)-propyl)-diethyl malonate disodium salt

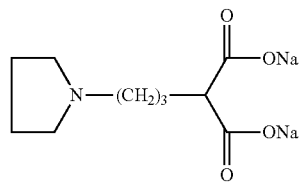

2M NaOH solution (2.5 mL) was added to 2-(3-(1-pyrrolidyl)-propyl)-diethyl malonate (545 mg, 2 mmol) in 20 mL flasks; and the mixture was stirred at room temperature for 45~60 h, 2-(3-(1-pyrrolidyl)-propyl)-malonic acid disodium salt solution was obtained.

Step 4, 5: Same as [Embodiment 1] Step 4, 5

Step 6: [2-(3-(1-pyrrolidyl)-propyl)-malonato].[cis-diamine] platinum (II) phosphate

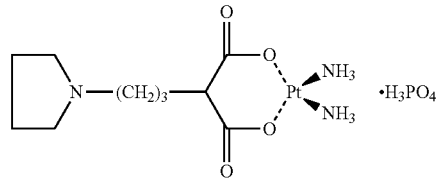

2-(3-(1-pyrrolidyl)-propyl)-malonic acid disodium salt (2 mmol) solution was regulated to the pH 5~7 with H3PO4 (1M) and then aqueous cis-diamine.dihydrate platinum (II) sulphate was poured into reaction mixture; the mixture was heated in water bath to 40~75° C. for 4-6 h, the mixture was concentrated to certain volume and the residue was standstill at room temperature; the title compound (123 mg) was obtained by suction.

The said compound is soluble in water. The solubility is 160 mg/ml. It can be easily converted into other types of organic or inorganic salts through ionization. It may be but not limited to sulphate, mesylate, tartrate, succinate, acetate, citrate, tosilate, fumarate, etc. Free base elemental analysis: C26.73% (theoretical 26.98%); H4.96% (theoretical 4.76%); N9.38% (theoretical 9.52%). $^1$HNMR(D$_2$O)(ppm): $\delta$3.61(t, 1H), $\delta$2.85(m,4H), $\delta$2.71(m,2H), $\delta$1.85(m,2H), $\delta$1.79(m 4H), $\delta$1.51(m,2H).

Test 1: Acute Toxic Effect of Platinum Complex on Normal Mice

Kunming mice at 4~6 weeks old and at the weight of 18~22 g were taken, 50% male and 50% female. Embodiment platinum compound was dissolved with 5% glucose solution. Single intravenous administration (control: carboplatin and cisplatin) was made at different doses. Mortality and toxicity were observed after administration. Totally observing 14 days, LD$_{50}$ value was calculated with Bliss method according to mortality. the results are shown in Table 1:

TABLE 1

Results of Intravenous Injection of Cisplatin, Carboplatin and Embodiment Platinum Compounds to Rat LD$_{50}$:

| Control and Embodiment compound | LD$_{50}$ value (mmol/kg) |
|---|---|
| cisplatin | 0.044 |
| Carboplatin | 0.336 |
| compound 1 | 0.722 |
| compound 2 | 0.791 |
| compound 3 | 0.824 |
| compound 4 | 0.802 |
| compound 5 | 0.853 |
| compound 6 | 0.749 |
| compound 7 | 0.791 |
| compound 8 | 0.806 |
| compound 9 | 0.724 |
| compound 10 | 0.593 |
| compound 11 | 0.509 |
| compound 12 | 0.609 |
| compound 13 | 0.908 |
| compound 14 | 0.902 |
| Embodiment compound | |
| compound 15 | 0.469 |
| compound 16 | 0.524 |
| compound 17 | 0.616 |
| compound 18 | 0.784 |
| compound 19 | 0.802 |
| compound 20 | 0.753 |
| compound 21 | 0.716 |
| compound 22 | 0.882 |
| compound 23 | 0.702 |
| compound 24 | 0.509 |
| compound 25 | 0.520 |
| compound 26 | 0.758 |
| compound 27 | 0.729 |
| compound 28 | 0.767 |
| compound 29 | 0.784 |
| compound 30 | 0.802 |

Conclusion: The and acute toxicity of the compounds at the same molar concentration in the Embodiment are much smaller than cisplatin and Carboplatin.

Test 2: Cytotoxcity Effects of the Embodiment Platinum Containing Compounds on Tumor Cell The toxic action of Embodiment platinum containing compounds was observed on tumor cells by MTT colorimetric method. Several kinds of tumor cells in exponential growth phase were prepared into single cell suspension, inoculated on 96 pore plat at the density of 4×10$^4$/hole, cultivated for 24 hours to enable to adhere to wall with 1640 culture medium containing 10% fetal calf serum (complete medium) at 37° C.; the final culture volume was 100 μl. Cell morphology was observed after culture for 24 hours. For the dosage of platinum compounds, since IC$_{50}$ values of cells are different, the following concentrations are determined through pretest: appropriate adjustment on 200, 60, 20, 6, 2, 0.6 μg/ml cisplatin, 200, 60, 20, 6, 2, 0.6 μg/ml carboplatin, and Embodiment platinum containing compounds depending on the sensitivity to each cell. The results are shown in Table 2-7 below:

TABLE 2

The cytotoxicity (IC$_{50}$) of different test platinum compounds to different cell lines
The IC$_{50}$ (n = 6) of chemotherapeutic drugs to different cell lines

| | IC$_{50}$(mM) | | | | |
|---|---|---|---|---|---|
| cell lines | carboplatin | cisplatin | compound 1 | compound 2 | compound 3 |
| breast cancer MCF-7 | 0.103 | 0.012 | 0.057 | 0.11 | 0.202 |
| breast cancer MCF-7 Cisplatin resistance strain | 0.255 | 0.015 | 0.168 | 0.245 | 0.023 |
| lung cancer A549 | 0.232 | 0.016 | 0.087 | 0.132 | 0.152 |
| lung cancer H292 | 0.055 | 0.0053 | 0.103 | 0.021 | 0.0098 |

TABLE 3

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | |
|---|---|---|---|---|---|---|---|
| cell lines | carboplatin | cisplatin | compound 4 | compound 5 | compound 6 | compound 7 | compound 8 |
| Pulmonary epithelial cell BEAS-2B | 0.037 | 0.0033 | 0.042 | 0.13 | 0.161 | 0.075 | 0.049 |
| lung cancer Lewis | 0.038 | 0.045 | 0.068 | 0.041 | 0.224 | 0.128 | 0.057 |
| colon cancer SW480 | 0.087 | 0.015 | 0.387 | 0.032 | 0.652 | 0.051 | 0.020 |

TABLE 3-continued

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | |
|---|---|---|---|---|---|---|---|
| cell lines | carboplatin | cisplatin | compound 4 | compound 5 | compound 6 | compound 7 | compound 8 |
| lung cancer H292 | 0.055 | 0.0053 | 0.196 | 0.041 | 0.036 | 0.124 | 0.201 |

TABLE 4

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | |
|---|---|---|---|---|---|---|---|
| cell lines | carboplatin | cisplatin | compound 9 | compound 10 | compound 11 | compound 12 | compound 13 |
| Pulmonary epithelial cell BEAS-2B | 0.037 | 0.0033 | 0.057 | 0.22 | 0.168 | 0.015 | 0.145 |
| lung cancer Lewis | 0.038 | 0.045 | 0.069 | 0.143 | 0.213 | 0.057 | 0.036 |
| colon cancer SW480 | 0.087 | 0.015 | 0.071 | 0.094 | 0.057 | 0.203 | 0.080 |
| lung cancer H292 | 0.055 | 0.0053 | 0.063 | 0.054 | 0.006 | 0.241 | 0.316 |

TABLE 5

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | |
|---|---|---|---|---|---|---|---|
| cell lines | carboplatin | cisplatin | compound 14 | compound 15 | compound 16 | compound 17 | compound 18 |
| testis cell ST | 0.195 | 0.00899 | 0.251 | 0.012 | 0.016 | 0.302 | 0.147 |
| gastric cancer MGC803 | 0.625 | 0.0025 | 0.213 | 0.149 | 0.216 | 0.556 | 0.367 |
| colon cancer SW480 | 0.087 | 0.015 | 0.078 | 0.092 | 0.077 | 0.205 | 0.281 |
| lung cancer H292 | 0.055 | 0.0053 | 0.161 | 0.651 | 0.402 | 0.249 | 0.224 |

TABLE 6

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | |
|---|---|---|---|---|---|---|---|
| cell lines | carboplatin | cisplatin | compound 19 | compound 20 | compound 21 | compound 22 | compound 23 |
| testis cell ST | 0.195 | 0.00899 | 0.251 | 0.012 | 0.016 | 0.302 | 0.147 |
| gastric cancer MGC803 | 0.625 | 0.0025 | 0.213 | 0.149 | 0.216 | 0.556 | 0.367 |
| esophagus cancer ECA109 | 0.052 | 0.073 | 0.088 | 0.193 | 0.174 | 0.215 | 0.212 |
| lung cancer H292 | 0.055 | 0.0053 | 0.062 | 0.351 | 0.205 | 0.102 | 0.084 |

TABLE 7

The cytotoxicity (IC$_{50}$) of different test platinum compounds to different cell lines
The IC$_{50}$ (n = 6) of chemotherapeutic drugs to different cell lines

| | IC$_{50}$ (mM) | | | | | | | |
|---|---|---|---|---|---|---|---|---|
| cell lines | carboplatin | compound 24 | compound 25 | compound 26 | compound 27 | compound 28 | compound 29 | compound 30 |
| testis cell ST | 0.195 | 0.153 | 0.114 | 0.312 | 0.360 | 0.138 | 0.127 | 0.114 |
| gastric cancer MGC803 | 0.625 | 0.217 | 0.341 | 0.234 | 0.453 | 0.162 | 0.201 | 0.313 |
| esophagus cancer ECA109 | 0.052 | 0.125 | 0.196 | 0.163 | 0.350 | 0.256 | 0.263 | 0.147 |
| lung cancer H292 | 0.055 | 0.065 | 0.053 | 0.136 | 0.158 | 0.099 | 0.074 | 0.076 |

It is observed from Tables 2-7 show that embodiment compounds 1-30 have equivalent or stronger cytotoxic effects in vitro than carboplatin.

Test 3: In Vivo Antitumor Activity Research of Platinum Containing Compounds (1) Male nude mice 4~6 weeks old at the weight of 17~20 g was inoculated in armpit of the right forearm with 0.2 ml colon cancer SW480 cell line single-cell suspension, the inoculation concentration 1×10$^7$/ml, randomly grouped 24 hours after inoculation, 10 mice a group; each group was intravenously administered with 4 mg/kg (positive control group), isometric normal saline (negative control group), and Embodiment 1-8 compound group respectively, administered continuously, delivered drug every other day, totally 4 times, and all intraperitoneal injection; subcutaneous tumor is taken out for weighing after 10 days and tumor inhibition rate is calculated (see Table 8). The calculation formula of tumor inhabitation rate is:

$$\text{tumor inhibition rate \%} = \frac{\text{average tumor weight of control group} - \text{average tumor weight of medicated group}}{\text{average tumor weight of control group}} \times 100$$

TABLE 8

Results of research on anti-colon cancer
SW480 activity of target compounds

| compounds | size of animal (set) | dose (mg/kg) | tumor inhibition rate (%) (x ±SD) |
|---|---|---|---|
| carboplatin | 10 | 4 | 20.5 ± 3.27 |
| compound 1 | 10 | 4 | 33.8 ± 11.58* |
| compound 2 | 10 | 4 | 30.2 ± 10.33* |
| compound 3 | 10 | 4 | 24.7 ± 9.56 |
| compound 4 | 10 | 4 | 25.3 ± 10.34 |
| compound 5 | 10 | 4 | 21.9 ± 7.52 |
| compound 6 | 10 | 4 | 24.9 ± 9.01 |
| compound 7 | 10 | 4 | 28.5 ± 7.65* |
| compound 8 | 10 | 4 | 29.7 ± 8.81* |

*Compare with carboplatin 4 mg group, p < 0.05

(2) Male nude mice 4~6 weeks old at the weight of 17~20 g were inoculated with 50 µl colon cancer SW480 cell line single-cell suspension at the inoculation concentration of $1 \times 10^7$/ml at subcutaneous position of left forelimb, randomly grouped 5 days later, 10 mice a group; each group is intravenously administered with 3, 5 mg/kg of cisplatin (positive control group), isometric normal saline (negative control group), 3, 5, 10, 15 mg/kg of Embodiment 1 compound group, and 3, 5, 10, mg/kg of Embodiment 8 compound group respectively, continuously administered for 3 days, and all intraperitoneal injection; subcutaneous tumor is taken out for weighing 24 hours after drug discontinuance and tumor inhibition rate is calculated (see Table 9).

TABLE 9

Results of research on anti-colon cancer
SW480 activity of target compounds

| compounds | size of animal (set) | dose (mg/kg) | tumor inhibition rate (%) (x ±SD) |
|---|---|---|---|
| cisplatin | 10 | 3 | 62.9 ± 9.01 |
| cisplatin | 10 | 5 | 71.1 ± 10.76 |
| compound 1 | 10 | 3 | 43.9 ± 10.51 ▲ |
| compound 1 | 10 | 5 | 46.8 ± 8.89 ▲ |
| compound 1 | 10 | 10 | 79.9 ± 9.30* |
| compound 1 | 10 | 15 | 86.8 ± 11.21* |
| compound 8 | 10 | 3 | 40.4 ± 5.02 ▲ |
| compound 8 | 10 | 5 | 73.6 ± 9.18 |
| compound 8 | 10 | 10 | 74.4 ± 12.25 |
| compound 8 | 10 | 15 | 82.8 ± 10.07* |

*Compare with cisplatin 5 mg group, p < 0.05
▲ Compare with cisplatin 3 mg group, the action is weak.

(3) Male nude mice 4~6 weeks old at the weight of 17~20 g were inoculated with 0.2 ml lung cancer H292 cell line cell line single-cell suspension at the inoculation concentration of $1 \times 10^7$/ml at subcutaneous position of back close to armpit, randomly grouped after 2 weeks, 10 mice a group; each group is intravenously administered with 15 mg/kg carboplatin (positive control group), isometric normal saline (negative control group), and 15 mg/kg Embodiment 9-16 compound group respectively; administered every 2 days, totally 4 times, and all intraperitoneal injection; the test ends 30 days after inoculation; subcutaneous tumor is taken out for weighing and tumor inhibition rate is calculated (see Table 10).

TABLE 10

Results of research on anti-lung H292 activity of target compounds

| compounds | size of animal (set) | dose (mg/kg) | tumor inhibition rate (%) |
|---|---|---|---|
| carboplatin | 10 | 15 | 55.2 ± 12.89 |
| compound 9 | 10 | 15 | 79.2 ± 14.99** |
| compound 10 | 10 | 15 | 55.3 ± 11.21 |
| compound 11 | 10 | 15 | 35.9 ± 7.13 ▲ |
| compound 12 | 10 | 15 | 76.3 ± 20.67* |
| compound 13 | 10 | 15 | 56.1 ± 9.81 |
| compound 14 | 10 | 15 | 39.8 ± 8.51 ▲ |
| compound 15 | 10 | 15 | 59.0 ± 11.02 |
| compound 16 | 10 | 15 | 35.2 ± 6.43 ▲ |

*Compare with carboplatin 15 mg group, p < 0.05
**Compare with carboplatin 15 mg group, p < 0.01
▲ Compare with carboplatin 15 mg group, the action is weak.

(4) Male nude mice 4~6 weeks old at the weight of 17~20 g were inoculated with 0.2 ml breast cancer MCF-7 tumor cell line single-cell suspension at the concentration of $1 \times 10^8$/ml at subcutaneous position of back close to armpit, randomly grouped after 2 weeks, 10 mice a group; each group is intravenously administered with 15 mg/kg carboplatin (positive control group), isometric normal saline (negative control group), and 15 mg/kg Embodiment 17-24 compound group respectively; administered every 2 days, totally 4 times, and all intraperitoneal injection; the test ends 30 days after inoculation; subcutaneous tumor is taken out for weighing and tumor inhibition rate is calculated (see Table 11).

TABLE 11

Results of research on anti-breast cancer
MCF-7 activity of target compounds

| compounds | size of animal (set) | dose (mg/kg) | tumor inhibition rate (%) |
|---|---|---|---|
| carboplatin | 10 | 15 | 40.1 ± 10.34 |
| compound 17 | 10 | 15 | 39.8 ± 12.12 |
| compound 18 | 10 | 15 | 45.0 ± 9.87 |
| compound 19 | 10 | 15 | 52.6 ± 10.5* |
| compound 20 | 10 | 15 | 54.52 ± 10.25* |
| compound 21 | 10 | 15 | 40.3 ± 9.65 |
| compound 22 | 10 | 15 | 40.9 ± 8.97 |
| compound 23 | 10 | 15 | 44.1 ± 15.12 |
| compound 24 | 10 | 15 | 44.8 ± 11.31 |

*Compare with carboplatin 15 mg group, p < 0.05

(5) Male nude mice 4~6 weeks old at the weight of 17~20 g were inoculated with 0.2 ml lung cancer Lewis cell line single-cell suspension at the inoculation concentration of $1 \times 10^7$/ml at subcutaneous position of back close to armpit, randomly grouped after 2 weeks, 10 mice a group; each group is intravenously administered with 15 mg/kg carboplatin (positive control group), isometric normal saline (negative control group), 15 mg/kg Embodiment 25-37 compound group respectively; administered every 2 days, totally 4 times, and all intraperitoneal injection; the test ends 30 days after inoculation; subcutaneous tumor is taken out for weighing and tumor inhibition rate is calculated (see Table 12).

TABLE 12

Results of research on Lewis Activity of Anti-lung Cancer of Target Compound

| compounds | size of animal (set) | dose (mg/kg) | tumor inhibition rate (%) |
|---|---|---|---|
| carboplatin | 10 | 15 | 70.2 ± 10.09 |
| compound 25 | 10 | 15 | 80.1 ± 9.65* |
| compound 26 | 10 | 15 | 72.4 ± 16.78 |
| compound 27 | 10 | 15 | 71.3 ± 10.54 |
| compound 28 | 10 | 15 | 73.3 ± 17.92 |

*Compare with carboplatin 15 mg group, p < 0.05

PREPARATION EXAMPLE 1

Preparation of Injection

Prescription 1

| phosphate of compound in example 5 | 10 g |
|---|---|
| glucose | 50 g |
| Add water for injection to to produce into 1000 | 1000 ml |

Process: 10 g phosphate and 50 g glucose of the compound in Embodiment 5 was dissolved in 1000 ml injection water at normal temperature in 2000 ml glassware, after filtration with 0.22 µm microporous membrane, the filtration was charged into 1 ml ampoule to obtain the product at the specification of 10 mg/ml.

Prescription 2

| mesylate of compound in example 8 | 10 g |
|---|---|
| glucose | 50 g |
| Add water for injection to to produce into 1000 | 1000 ml |

Process: 10 g mesylate and 50 g glucose of the compound in Embodiment 8 was dissolved into 1000 ml injection water at normal temperature in 1000 ml glassware, after filtration with 0.22 µm microporous membrane, the filtration was charged into 2 ml penicillin bottle to afford the product at the specification of 10 mg/bottle.

PREPARATION EXAMPLE 2

Preparation of Refrigerated Powder for Injection

Prescription 1

| mesylate of compound in example 8 | 10 g |
|---|---|
| Mannitol | 50 g |
| Add water for injection to to produce into 1000 | 1000 ml |

Process: 10 g compound and 50 g Mannitol in Embodiment 8 were dissolved into 1000 ml injection water at normal temperature in 1000 ml glassware, after filtration with 0.22 am microporous membrane, the filtration was charged into 2 ml penicillin bottle, 1 ml solution in each bottle, and then refrigerated to obtain the product at the specification of 10 mg/bottle.

Prescription 2

| phosphate of compound in examole 15 | 20 g |
|---|---|
| Mannitol | 50 g |
| Add water for injection to to produce into 1000 | 1000 ml |

Process: 20 g phosphate and 50 g Mannitol of the compound in Embodiment 15 was dissolved into 1000 ml injection water at normal temperature in 1000 ml glassware, after filtration with 0.22 µm microporous membrane, the filtration was charged into 2 ml penicillin bottle, 1 ml solution in each bottle, and then refrigerated to obtain the product at the specification of 20 mg/bottle.

Prescription 3

| tosilate of compound in example 20 | 50 g |
|---|---|
| Add water for injection to to produce into 1000 | 1000 ml |

Process: 50 g tosilate of the compound in Embodiment 20 was dissolved into 1000 ml injection water at normal temperature in 1000 ml glassware, after filtration with 0.22 µm microporous membrane, the filtration was charged into 2 ml penicillin bottle, 1 ml solution in each bottle, and then refrigerated to obtain the product at the specification of 50 mg/bottle.

The invention claimed is:

1. A compound of formula A, or a pharmaceutically acceptable salt, solvate, isomer, or prodrug thereof,

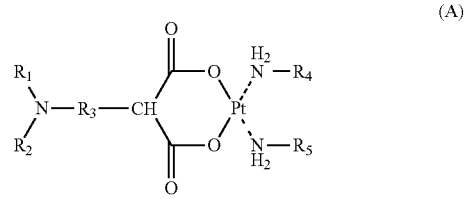
(A)

wherein:
 $R_1$ and $R_2$ are the same or different, selected from hydrogen, alkyl, naphthenic base, alkoxy alkyl, alkyl amino alkyl, heterocycle, alkenyl, alkynyl; wherein hydrocarbyl, alkoxy alkyl, alkyl amino alkyl and heterocycle are unsubstituted or optionally substituted, provided that $R_1$ and $R_2$ do not contain an unsaturated bond, or $R_1$ and/or $R_2$ contains an unsaturated bond, while the atom of the unsaturated bond cannot be directly connected with a nitrogen atom;
 $R_3$ is selected from alkyl, naphthenic base and —$R_{31}$—O—$R_{32}$—; $R_{31}$ and $R_{32}$ are independently selected from bond or alkyl; $R_{31}$ is connected with nitrogen atom; provided that $R_{31}$ does not contain an unsaturated bond, or $R_{31}$ contains an unsaturated bond, while the atom of the unsaturated bond cannot be directly connected with the nitrogen atom; wherein the alkyl and naphthenic base are unsubstituted or optionally substituted;
 $R_4$ and $R_5$ are the same or different, selected from: hydrogen, hydroxyl, alkyl, naphthenic base, alkoxy, alkoxy alkyl, heterocycle, alkenyl, alkynyl; wherein alkyl, alkenyl, alkynyl, naphthenic base, alkoxy alkyl, alkyl amino alkyl and heterocycle are unsubstituted or optionally substituted;

$R_4$, $R_5$ and the atoms they connected maybe together form a closed ring; the said ring may be quaternary, pentabasic, hexahydric, heptabasic or octatomic ring; said ring is optionally condensed with other rings and optionally substituted.

2. A compound according to claim 1, wherein said compound is as shown in formula B,

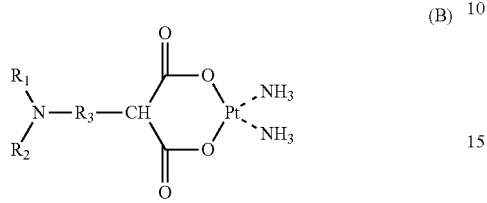

wherein:
$R_1$, $R_2$ and $R_3$ are as described in claim 1.

3. A compound according to claim 1, wherein $R_1$ and $R_2$ are independently selected from hydrogen, methyl, ethyl or propyl; $R_3$ is ethyl or propyl; $R_4$ and $R_5$ are hydrogen.

4. A compound according to claim 1, wherein said compound is as shown in formula C,

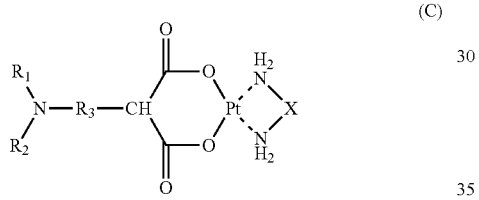

wherein,

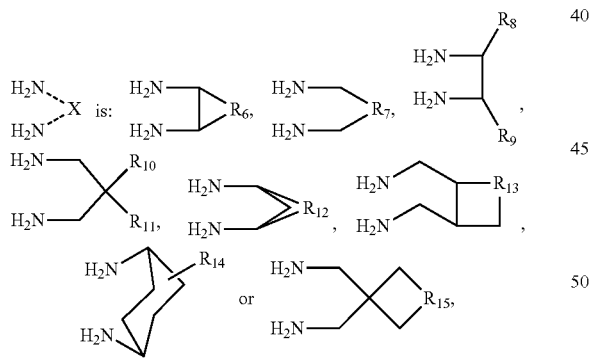

which may be optionally substituted;

$R_1$ and $R_2$ are the same or different, selected from hydrogen, alkyl, naphthenic base, alkoxy alkyl, alkyl amino alkyl, heterocycle, alkenyl, alkynyl; wherein alkyl, alkoxy alkyl, alkyl amino alkyl and heterocycle may be unsubstituted or optionally substituted, provided that $R_1$ and $R_2$ do not contain unsaturated bonds, or $R_1$ and/or $R_2$ contains an unsaturated bond, while the atom of the unsaturated bond cannot be directly connected with a nitrogen atom;

$R_3$ is selected from alkyl, naphthenic base and $-R_{31}-$ $O-R_{32}-$; $R_{31}$ and $R_{32}$ are independently selected from bond or alkyl; $R_{31}$ is connected with a nitrogen atom, provided that $R_{31}$ does not contain an unsaturated bond, or $R_{31}$ contains an unsaturated bond, while the atom of the unsaturated bond cannot be directly connected with the nitrogen atom; wherein the alkyl or naphthenic base described are unsubstituted or optionally substituted;

$R_6$ is selected from $(CH_2)_n$, wherein n=1-6, wherein some $-CH_2-$ may be substituted by $-O-$; wherein one or more hydrogens of $(CH_2)_n$ are optionally substituted by fluorine, alkyl, hydroxyl or alkoxy, heterocycle; the compound is selected from (±)trans-1, 2-cyclohexanediamine platinum (II), trans-1, 2-cyclopentamethylenediamine platinum (II), trans-1, 2-cyclobutanediamine platinum (II) and trans-1, 2-cyclopropane diamine platinum (II);

$R_7$ is selected from $(CH_2)_n$, wherein n=0-3; wherein some $-CH_2-$ may be substituted by $-O-$; wherein one or more hydrogens of $(CH_2)_n$ are optionally substituted by halogen, alkyl, hydroxyl, hydroxyalkyl, alkoxy, heterocycle;

$R_8$ and $R_9$ are selected from hydrogen, halogen, hydroxyl, hydroxyalkyl, alkyl, alkoxy and heterocycle; $R_8$ and $R_9$ may be the same or different;

$R_{10}$ and $R_{11}$ are selected from hydrogen, halogen, hydroxyalkyl, alkyl, alkoxy and heterocycle; $R_{10}$ and $R_{11}$ may be the same or different;

$R_{12}$ is selected from $(CH_2)_n$, wherein n=2-4, wherein some $-CH_2-$ may be substituted by $-O-$; one or more hydrogens of $(CH_2)_n$ are optionally substituted by halogen, alkyl, hydroxyl, alkoxy or heterocycle;

$R_{13}$ is $-CH_2-$ or $-O-$;

$R_{14}$ is hydrogen, halogen, alkyl, alkoxy, heterocycle, hydroxyalkyl or hydroxyl;

$R_{15}$ is but not limited to $(CH_2)_n$, wherein n=1-3, $-CH_2-$ $O-$ or $-O-$; wherein one or more hydrogens of $(CH_2)_n$ are optionally substituted by alkyl, alkoxy, heterocycle, hydroxyl, or hydroxyalkyl.

5. A compound according to claim 4, wherein said compound is of formula below:

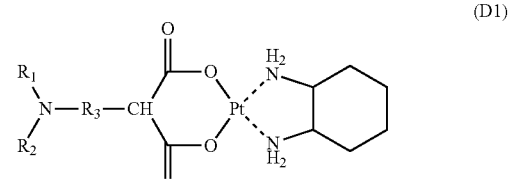

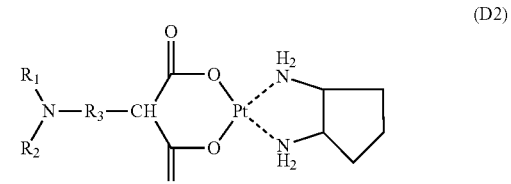

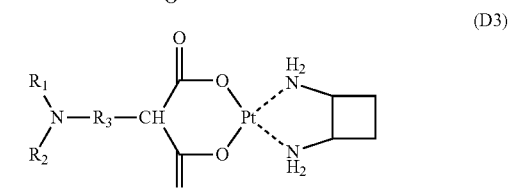

-continued (D4) 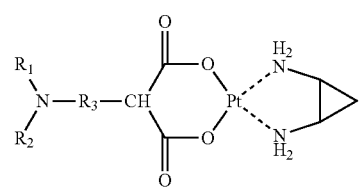

(E1) 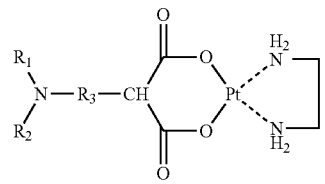

(E2) 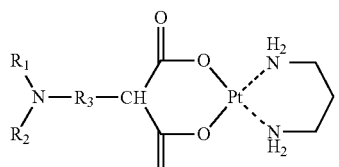

(E3) 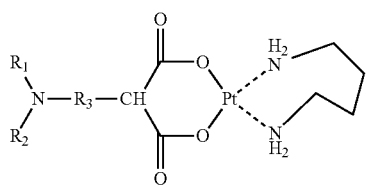

(F) 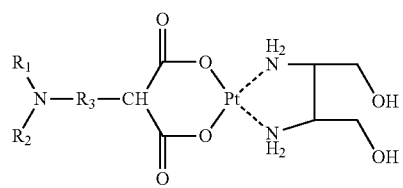

(G) 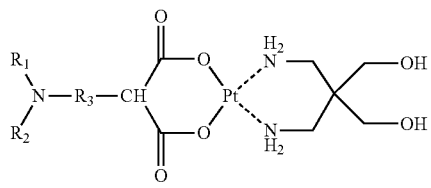

(H) 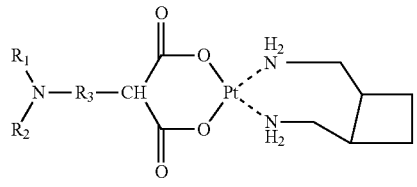

(I) 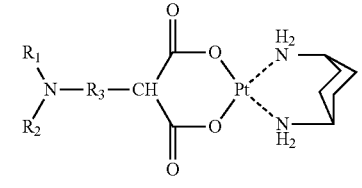

-continued (J) 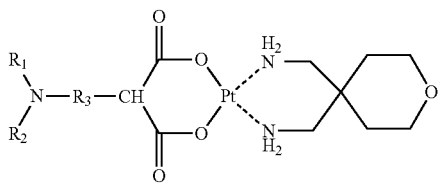

wherein $R_1$ and $R_2$ are as described in claim 4.

6. A compound or pharmaceutical acceptable salt, solvate, isomers or prodrug thereof according to claim 1, wherein said compounds is selected from the group consisting of:

compound 1:[2-(2-methylamino ethyl)-malonato].[cis-diamine] platinum (II);
compound 2:[2-(2-dimethylamino ethyl)-malonato].[cis-diamine] platinum (II);
compound3:[2-(3-dimethylamino propyl)-malonato].[cis-diamine] platinum (II);
compound4:[2-(3-amino propyl)-malonato].[cis-diamine] platinum (II);
compound 5:[2-(2-diethylamino ethyl)-malonato].[cis-diamine] platinum (II);
compound 6:[2-(3-diethylamino propyl)-malonato].[cis-diamine] platinum (II);
compound 7: [2-(2-di-n-propylamino ethyl)-malonato].[cis-diamine] platinum (II);
compound8:[2-(3-di-n-propylamino propyl)-malonato].[cis-diamine] platinum (II);
compound 9: [2-(2-amino ethyl)-malonato].[cis-(1,2-trans-cyclohexane diamine)] platinum (II);
compound 10: [2-(2-dimethylamino ethyl)-malonnato].[cis-(1,2-trans-cyclohexane diamine)] platinum (II);
compound 11: [2-(3-dimethylamino propyl)-malonato].[cis-(1,2-trans-cyclohexane diamine)] platinum (II);
compound 12: [2-(2-ethylamino ethyl)-malonato].[cis-(1,2-trans-cyclohexane diamine)] platinum (II);
compound 13: [2-(2-diethylamino ethyl)-malonato].[cis-(1,2-trans-cyclohexane diamine)] platinum (II);
compound 14: [2-(3-diethylamino propyl)-malonato].[cis-(1,2-trans-cyclohexane diamine)] platinum (II);
compound 15: [2-(2-di-n-propylamino ethyl)-malonato].[cis-(1,2-trans-cyclohexane diamine)] platinum (II);
compound 16: [2-(3-di-n-propylamino propyl)-malonato].[cis-(1,2-trans-cyclohexane diamine)] platinum (II);
compound 17: [2-(3-diethylamino propyl)-malonato].[cis-(1, 2-trans-cyclopentyl diamine)] platinum (II);
compound 18: [2-(3-diethylamino propyl)-malonato].[cis-(1,2-trans-cyclobutyl diamine)] platinum (II);
compound 19: [2-(3-diethylamino propyl)-malonato].[cis-(1,2-trans-cyclopropyl diamine)] platinum (II);
compound 20: [2-(2-dimethylamino ethyl)-malonato].[cis-1, 2-ethyldiamine] platinum (II);
compound 21: [2-(2-diethylamino ethyl)-malonato].[cis-1, 3-propyl diamine] platinum (II);
compound 22: [2-(2-di-n-propylamino ethyl)-malonato].[cis-1, 4-butyldiamine] platinum (II);
compound 23: [2-(2-diethylamino ethyl)-malonato].[cis-1,2-(1,2-dihydroxymethyl)-ethyl diamine] platinum (II);
compound 24: [2-(2-dimethylamino ethyl)-malonato].[cis-1,3-(2,2-hydroxymethyl)-propyl diamine] platinum (II);
compound 25: [2-(2-dimethylamino ethyl)-malonato].[cis-1,4-(trans-2,3-cyclobutyl)-butane diamine] platinum (II);

compound 26: [2-(2-diethylamino ethyl)-malonic].[cis-1,4-(trans-2,3-cyclobutyl)-butane diamine] platinum (II);

compound 27: [2-(2-diethylamino ethyl)-malonato].[cis-1,4-cyclohexane diamine] platinum (II);

compound 28: [2-(2-diethylamino ethyl)-malonato].[cis-1,3-(2,2-(4-oxacyclohexyl))-propyl diamine] platinum (II);

compound 29: [2-(3-(1-piperidyl)-propyl)-malonato].[cis-diamine] platinum (II);

compound 30: [2-(3-(1-pyrrolidyl)-propyl)-malonato].[cis-diamine] platinum (II).

7. A compound according to claim 1, wherein the said compound is in the form of pharmaceutically acceptable salt; the pharmaceutically acceptable salt is selected from nitrate, carbonate, sulphate, phosphate, mesylate, trifluoromethane-sulfonic salt, tosilate, benzene sulfonate, acetate, fumarate, tartrate, oxalate, maleate, malate, succinate, lactate, citrate, glutamate, or aspartate.

8. A pharmaceutical composition, containing the compound in claim 1 and pharmaceutically acceptable carrier; wherein the said composition is in any appropriate dosage form; and it may or may not contain one or more of other drugs suitable for the treatment of cancer.

9. The preparation method for the compound in claim 1, including the following steps:

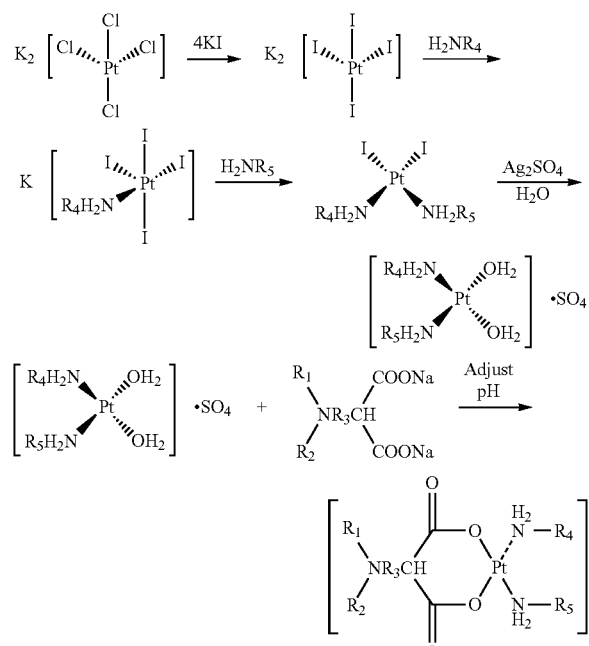

or including the following steps:

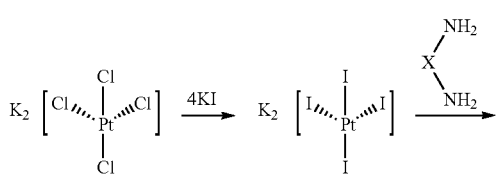

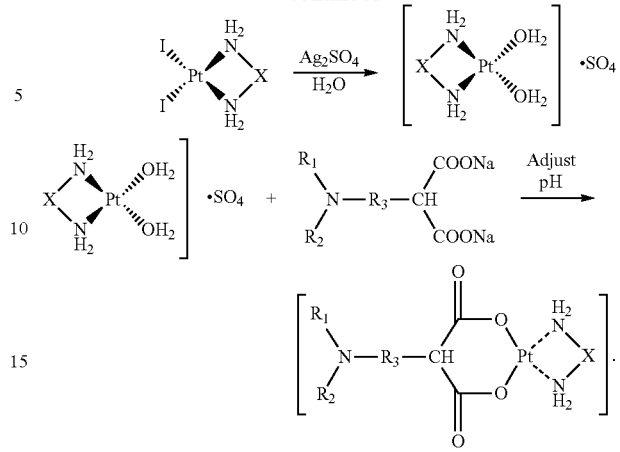

10. A method of treating a cell proliferation disease, comprising administering a composition comprising the compound of claim 1, its pharmaceutically acceptable salt, its solvate, its isomers or its prodrug of claim 1.

11. The method of treating a cell proliferation disease in a subject of claim 10, comprising administering the compound, its pharmaceutically acceptable salt, its solvate, its isomers, or its prodrug.

12. A kit, including the pharmaceutical composition in claim 8 and instructions, wherein said kit may comprise one or more other drugs for the treatment of cancer.

13. A compound according to claim 4, wherein $R_6$ is selected from $(CH_2)_n$, wherein n=3-5.

14. A compound according to claim 1, wherein $R_1$ and $R_2$ are the same or different, selected from hydrogen, alkyl, naphthenic base, alkoxy alkyl, alkyl amino alkyl, heterocycle, alkenyl, alkynyl; wherein said hydrocarbyl, alkoxy alkyl, alkyl amino alkyl and heterocycle are substituted by halogen, hydroxyl, alkoxy, alkyl, alkoxy alkyl, naphthenic base, heterocycle.

15. A compound according to claim 1, wherein $R_3$ is selected from alkyl, naphthenic base and $-R_{31}-O-R_{32}-$; $R_{31}$ and $R_{32}$ are independently selected from bond or alkyl; $R_{31}$ is connected with nitrogen atom; provided that $R_{31}$ does not contain an unsaturated bond, or $R_{31}$ contains unsaturated bond, while the atom of the unsaturated bond cannot be directly connected with the nitrogen atom; wherein the alkyl and naphthenic base are substituted by halogen, hydroxyl, alkoxy, alkyl, alkoxy alkyl, naphthenic base, or heterocycle.

16. A compound according to claim 1, wherein $R_4$ and $R_5$ are the same or different, selected from: hydrogen, hydroxyl, alkyl, naphthenic base, alkoxy, alkoxy alkyl, heterocycle, alkenyl, alkynyl; wherein alkyl, alkenyl, alkynyl, naphthenic base, alkoxy alkyl, alkyl amino alkyl and heterocycle may be substituted by halogen, hydroxyl, alkoxy, straight chain or branched-chain alkyl, alkoxy alkyl, naphthenic base and heterocycle.

17. A compound according to claim 1, wherein $R_4$, $R_5$ and the atoms they connected maybe together form a closed ring; the said ring may be quaternary, pentabasic, hexahydric, heptabasic or octatomic ring; said ring may be substituted by halogen, hydroxyl, alkoxy, straight chain or branched-chain alkyl, alkoxy alkyl, naphthenic base and heterocycle.

18. A compound according to claim 4, wherein $R_1$ and $R_2$ are the same or different, selected from hydrogen, alkyl, naphthenic base, alkoxy alkyl, alkyl amino alkyl, heterocycle, alkenyl, alkynyl; wherein alkyl, alkoxy alkyl, alkyl amino alkyl and heterocycle may be substituted by halogen, hydroxyl, alkoxy, alkyl, alkoxy alkyl, naphthenic base, heterocycle.

19. A compound according to claim 4, wherein $R_3$ is selected from alkyl, naphthenic base and —$R_{31}$—O—$R_{32}$—; $R_{31}$ and $R_{32}$ are independently selected from bond or alkyl; $R_{31}$ is connected with a nitrogen atom, provided that $R_{31}$ does not contain an unsaturated bond, or $R_{31}$ contains an unsaturated bond, while the atom of the unsaturated bond cannot be directly connected with the nitrogen atom; wherein the alkyl or naphthenic base described are substituted by halogen, hydroxyl, alkoxy, alkyl, alkoxy alkyl, naphthenic base or heterocycle.

20. A method for the treatment of cell proliferation diseases, comprising administering the pharmaceutical composition of claim 13 to patients.

21. A compound according to claim 4, wherein $R_6$ is selected from $(CH_2)_n$, wherein n=4.

22. A compound according to claim 4, wherein $R_7$ is selected from $(CH_2)_n$, wherein n=0-2.

23. A compound according to claim 4, wherein $R_8$ and $R_9$ are hydroxymethyl (formula F).

24. A compound according to claim 4, wherein $R_{10}$ and $R_{11}$ are hydroxymethyl.

25. A compound according to claim 4, wherein $R_{13}$ is —$CH_2$—.

26. A compound according to claim 4, wherein $R_{14}$ is hydrogen.

27. A compound according to claim 4, wherein $R_{15}$ is but not limited to $(CH_2)_n$, wherein n=1-3, —$CH_2$—O— or —O—; wherein one or more hydrogens of $(CH_2)_n$ are substituted by —$CH_2$—O—$CH_2$—.

28. A pharmaceutical composition according to claim 8, wherein the said composition is in the form of injection.

29. A method according to claim 10, wherein the cell proliferation diseases are cancers.

30. A method according to claim 29, wherein the cancer is breast cancer, lung cancer, colon cancer, gastric cancer, esophagus cancer, ovarian cancer, osteosarcoma, cervical cancer, bladder cancer, liver cancer, cerebroma, prostate cancer, or melanoma.

31. A method according to claim 11, wherein the cell proliferation diseases are cancers.

32. A method according to claim 31, wherein the cancer is breast cancer, lung cancer, colon cancer, gastric cancer, esophagus cancer, ovarian cancer, osteosarcoma, cervical cancer, bladder cancer, liver cancer, cerebroma, prostate cancer, or melanoma.

33. A method according to claim 20, wherein the cell proliferation diseases are cancers.

* * * * *